(12) United States Patent
Robichaud et al.

(10) Patent No.: US 11,884,697 B2
(45) Date of Patent: Jan. 30, 2024

(54) OXYSTEROLS AND METHODS OF USE THEREOF

(71) Applicant: Sage Therapeutics, Inc., Cambridge, MA (US)

(72) Inventors: Albert Jean Robichaud, Boston, MA (US); Francesco G. Salituro, Marlborough, MA (US); Gabriel Martinez Botella, Wayland, MA (US); Boyd L. Harrison, Princeton Junction, NJ (US); John Gregory Reid, Wellington, FL (US)

(73) Assignee: Sage Therapeutics, Inc., Cambridge, MA (US)

( * ) Notice: Subject to any disclaimer, the term of this patent is extended or adjusted under 35 U.S.C. 154(b) by 90 days.

(21) Appl. No.: 17/242,860

(22) Filed: Apr. 28, 2021

(65) Prior Publication Data
US 2021/0261598 A1   Aug. 26, 2021

Related U.S. Application Data

(63) Continuation of application No. 16/089,896, filed as application No. PCT/US2017/025535 on Mar. 31, 2017, now abandoned.

(60) Provisional application No. 62/317,002, filed on Apr. 1, 2016.

(51) Int. Cl.
| | | |
|---|---|---|
| A61K 31/57 | (2006.01) | |
| C07J 9/00 | (2006.01) | |
| C07J 17/00 | (2006.01) | |
| C07J 43/00 | (2006.01) | |

(52) U.S. Cl.
CPC ............ C07J 9/00 (2013.01); A61K 31/57 (2013.01); C07J 17/00 (2013.01); C07J 43/003 (2013.01)

(58) Field of Classification Search
CPC .. C07J 9/00; C07J 17/00; C07J 43/003; A61P 1/00; A61P 3/065; A61P 3/10; A61P 25/00; A61P 25/20; A61P 35/00; A61K 31/57; A61K 31/58
USPC .................................. 514/176, 181
See application file for complete search history.

(56) References Cited

U.S. PATENT DOCUMENTS

| | | |
|---|---|---|
| 2,259,698 A | 10/1941 | Johannessohn et al. |
| 2,594,323 A | 4/1952 | Levin et al. |
| 3,079,385 A | 2/1963 | Bertin et al. |
| 3,206,459 A | 9/1965 | Cross |
| 4,071,625 A | 1/1978 | Grunwell et al. |
| 5,232,917 A | 8/1993 | Bolger et al. |
| 5,376,645 A | 12/1994 | Stella et al. |
| 5,512,570 A | 4/1996 | Dorn et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 6,933,312 B2 | 8/2005 | Price et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,201,550 B2 | 2/2019 | Salituro et al. |
| 10,227,375 B2 | 3/2019 | Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 10,759,828 B2 | 9/2020 | Upasani et al. |
| 11,104,701 B2 | 8/2021 | Botella et al. |
| 11,111,266 B2 | 9/2021 | Salituro et al. |
| 11,149,054 B2 | 10/2021 | Salituro et al. |
| 2004/0048838 A1 | 3/2004 | Gronvald et al. |

(Continued)

FOREIGN PATENT DOCUMENTS

| | | |
|---|---|---|
| AU | 728843 | 1/2001 |
| CN | 1254716 | 5/2008 |

(Continued)

OTHER PUBLICATIONS

Berge et al., "Pharmaceutical salts," Journal of Pharmaceutical Sciences, 66(1):1-19 (1977).

(Continued)

*Primary Examiner* — Taylor V Oh
(74) *Attorney, Agent, or Firm* — HALEY GUILIANO LLP; Karen Mangasarian; Jacob E. Dander

(57) ABSTRACT

Compounds are provided according to Formula (I), and pharmaceutically acceptable salts thereof, and pharmaceutical compositions thereof; wherein A, $R^1$, and $R^5$ are as defined herein. Compounds of the present invention are contemplated useful for the prevention and treatment of a variety of conditions.

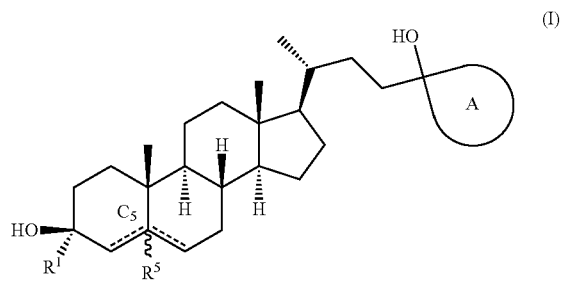

27 Claims, No Drawings

(56) References Cited

U.S. PATENT DOCUMENTS

| | | |
|---|---|---|
| 2005/0101573 A1 | 5/2005 | Faarup et al. |
| 2006/0142241 A1 | 6/2006 | Yoo |
| 2006/0199790 A1 | 9/2006 | Baulieu et al. |
| 2007/0032464 A1 | 2/2007 | Lia et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0112077 A1 | 5/2011 | Kuduk et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1* | 6/2015 | Upasani .......... A61P 25/08 552/611 |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0233465 A1 | 8/2019 | Robichaud et al. |
| 2019/0248829 A1 | 8/2019 | Salituro et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2020/0123195 A1 | 4/2020 | Salituro et al. |
| 2021/0040138 A1 | 2/2021 | Harrison et al. |
| 2021/0101925 A1 | 4/2021 | Salituro et al. |
| 2021/0145848 A1 | 5/2021 | Salituro et al. |
| 2021/0147468 A1 | 5/2021 | Salituro et al. |
| 2021/0147470 A1 | 5/2021 | Upasani et al. |
| 2021/0171567 A1 | 6/2021 | Martinez et al. |
| 2021/0380631 A1 | 12/2021 | Salituro et al. |
| 2022/0081465 A1 | 3/2022 | Salituro et al. |

FOREIGN PATENT DOCUMENTS

| | | |
|---|---|---|
| FR | 2850023 | 7/2004 |
| GB | 1564806 | 4/1980 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 | 8/1999 |
| JP | 2005508368 | 3/2005 |
| JP | 2009545535 | 12/2009 |
| RU | 2194712 | 12/2002 |
| RU | 2458065 C2 | 8/2012 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996016076 | 5/1996 |
| WO | WO1996040043 | 12/1996 |
| WO | WO1996040151 | 12/1996 |
| WO | WO1997000884 | 1/1997 |
| WO | WO1997003677 | 2/1997 |
| WO | WO1998005337 | 2/1998 |
| WO | WO1998007740 | 2/1998 |
| WO | WO1999058497 | 11/1999 |
| WO | WO2000063228 | 10/2000 |
| WO | WO2000067755 | 11/2000 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2003039480 | 5/2003 |
| WO | WO2003049685 | 6/2003 |
| WO | WO2003082893 | 10/2003 |
| WO | WO2004007440 | 1/2004 |
| WO | WO2004048364 | 6/2004 |
| WO | WO2004055201 | 7/2004 |
| WO | WO2005079810 | 9/2005 |
| WO | WO2009073186 | 6/2006 |
| WO | WO2008041003 | 4/2008 |
| WO | WO2008063128 | 5/2008 |
| WO | WO2009001097 | 12/2008 |
| WO | WO2009059961 | 5/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2011092127 | 8/2011 |
| WO | WO2011141568 | 11/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013054822 | 4/2013 |
| WO | WO2013056181 | 4/2013 |
| WO | WO2013163455 | 10/2013 |
| WO | WO2014025942 | 2/2014 |
| WO | WO2014115167 | 7/2014 |
| WO | WO2014120786 | 8/2014 |
| WO | WO2014160441 | 10/2014 |
| WO | WO2014160480 | 10/2014 |
| WO | WO2015048316 | 4/2015 |
| WO | WO2015195967 | 12/2015 |
| WO | WO2016007762 | 1/2016 |
| WO | WO2016057713 | 4/2016 |
| WO | WO2017007832 | 1/2017 |
| WO | WO2017007836 | 1/2017 |
| WO | WO2017007840 | 1/2017 |
| WO | WO2017037465 | 3/2017 |
| WO | WO2017173358 | 10/2017 |
| WO | WO2018064649 | 4/2018 |
| WO | WO2018075698 | 4/2018 |
| WO | WO2018075699 | 4/2018 |
| WO | WO2018170336 | 9/2018 |
| WO | WO2020243027 | 12/2020 |
| WO | WO2002090375 | 11/2022 |

OTHER PUBLICATIONS

Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).

Bukelis et al., "Smith-Lemli-Opitz syndrome and autism spectrum disorder," American Journal of Psychiatry, 164(11):1655-1661 (2007).

Cais et al., "Temperature dependence of NR1/NR2B NMDA receptor channels," Neuroscience, 151(2):428-438 (2008).

(56) References Cited

OTHER PUBLICATIONS

Cancer [online], [retrieved on Jul. 6, 2007]. Retrieved from the internet, URL http://www.nlm.nih.gov/medlineplus/ cancer.html> (11 pages).
Chen et al., "The chemical biology of clinically tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxysterol agonists of the hedgehog signaling pathway," ACS Medicinal Chemistry Letters, 3(10):828-833 (2012).
Costa et al., "A novel family of negative and positive allosteric modulators of NMDA receptors," Journal of Pharmacology and Experimental Therapeutics, 335(3):614-21 (2010).
Cross et al., "Steroids CCLXXIN[1]. Biologically-active labile ethers IV[2]. The synthesis of 22-oxa-25-azacholesterol and related compounds," Steroids, 5(5):585-598 (1965).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Dayal et al., "Stereospecific synthesis of 3 beta-hydroxylated bile alcohols," Journal of Lipid Research, 25(6):646-650 (1984).
Deng et al., "Fluoro analogs of bioactive oxy-steroids: Synthesis of an $EBI_2$ agonist with enhanced metabolic stability," Bioorganic and Medicinal Chemistry Letters, 26(2):4888-4891 (2016).
Domasio, "Alzheimer's disease and related dementias," Cecil Textbook of Medicine, 20th edition, 2:1992-1996 (1996).
Elbarbry et al., "Cyclosporine-induced changes in drug metabolizing enzymes in hyperlipemic rabbit kidneys could explain its toxicity," Xenobiotica, 40(11):772-781 (2010).
European Search Partial Supplementary Report for European Application No. 14775126.7, dated Sep. 14, 2016 (7 pages).
Extended European Search Report for Application No. 15809462.3, dated Nov. 29, 2017 (8 pages).
Extended European Search Report for Application No. 16821920.2, dated Jan. 31, 2019 (12 pages).
Extended European Search Report for Application No. 16821924.4, dated Jan. 31, 2019 (12 pages).
Extended European Search Report for Application No. 16821926.9, dated Jan. 31, 2019 (10 pages).
Extended European Search Report for European Application No. 14774060.9, dated Aug. 17, 2016 (11 pages).
Extended European Search Report for European Application No. 14775126.7, Dec. 15, 2016 (6 pages).
Extended European Search Report for European Application No. 15849514.3, dated May 23, 2018 (7 pages).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs 16:2033-2052 (2010).
Festa et al., "Exploitation of cholane scaffold for the discovery of potent and selective farnesoid X receptor (FXR) and G-protein coupled bile acid receptor 1 (GP-BAR $_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12:(4)279-287 (1991).
Grynkiewicz et at., "A new generation of Ca2+ indicators with greatly improved fluorescence properties," Journal of Biological Chemistry, 260(6):3440-3345 (1985).
Gunatilaka et al., "Bioactive ergost-5-ene-3 beta, 7 alpha-diol derivatives from *Pseudobersama mossambicensis*," Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Iida et al., "An improved method for the capillary gas chromatographic derivatization of polyhydroxylated steroids having tert-hydroxyl groups," Analytical Sciences, 19(9):1317-1321 (2003).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LSR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical And Pharmaceutical Bulletin, 43(9):1551-1557 (1995).
Lakhan et al., " NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).

(56) References Cited

OTHER PUBLICATIONS

Layzer, "Section five-degenerative diseases of the nervous system," Cecil Textbook of Medicine, 20th edition, 2:2050-2057 (1996).
Leoni et al., "Changes in human plasma levels of the brain specific oxysterol 24S-hydroxycholesterol during progression of multiple sclerosis," Neuroscience Letters, 331(3):163-166 (2002).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Lutjohann et al., "Cholesterol homeostasis in human brain: evidence for an age-dependent flux of 24S-hydroxycholesterol from the brain into the circulation," PNAS, 93(18):9799-804 (1996).
Luu et al., "Oxysterols: Old Tale, New Twists," Annual Review of Pharmacology and Toxicology, 56:447-467 (2016).
Madau et al, Program No. 613.2/B87. 2009 Neuroscience Meeting Planner. Chicago, IL: Society for Neuroscience (2009) (3 pages).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-la,25-dihydroxyvitamin D3 and 24-nor-25-hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Nagasaka et al., "Oxysterol changes along with cholesterol and vitamin D changes in adult phenylketonuric patients diagnosed by newborn mass-screening," Clinica Chimica Acta, 416:54-59 (2013).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890).
Niemann-Pick overview [online] retrieved from the internet on Jul. 17, 2021 (URL:https://www.mayoclinic.org/diseases-conditions/niemann-pick/symptoms-causes/syc-20355887).
Olkkonen et al., "Oxysterols and their cellular effectors," Biomolecules, 2(1):76-103 (2012).
Papassotiropoulos et al., "Plasma 24S-hydroxycholesterol a peripheral indicator of neuronal degeneration and potential state marker for Alzheimer's disease," NeuroReport 11(9): 1959-1962 (2000).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," the Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Aug. 14, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Dec. 11, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Pubchem, CID 65094, 25-Hydroxycholesterol, Nov. 18, 2016 (17 pages).
Pubchem, CID 132021, Ergostan-3,24-diol, Mar. 5, 2018 (15 pages).
Pubchem, CID 54083335, Schemb14961477, Nov. 8, 2016 (13 pages).
Pubchem, CID 54160779, Schemb14961477, Nov. 8, 2016 (13 pages).
Pubchem, CID 58455549, Schemb112198161, Nov. 8, 2016 (13 pages).
Pubchem, CID 66966798, Cholane-3alpha,24,-diol, Nov. 8, 2016 (11 pages).
Pubchem, CID 70604305, Schemb111528874, Nov. 8, 2016 (13 pages).
Pubchem, CID 71508953, Mar. 5, 2018 (13 pages).
Reddy, "Pharmacology of endogenous neuroactive steroids," Critical Reviews in Neurobiology, 15(3-4):197-234 (2013).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113 (2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity,"Journal of Medicinal Chemistry, 54:4590-4599 (2011).
Solomon et al., "Plasma levels of 24S-hydroxycholesterol reflect brain volumes in patients without objective cognitive impairment but not in those with Alzheimer's disease," Neuroscience Letters 462(1): 89-93 (2009).

(56) References Cited

OTHER PUBLICATIONS

Stamp et al., "Plasma levels and therapeutic effect of 25-hydroxycholeciferol in epileptic patients taking anticonvulsant drugs," British Medical Journal, 4(5831):9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zhou et al., "Properties of HERF channels stably expressed in HEK 293 cells studied at physiological temperature," Biophysical Journal, 74(1):230-241 (1998).
Zuliani et al., "Plasma 24S-hydroxycholesterol levels in elderly subjects with late onset Alzheimer's disease or vascular dementia: a case-control study," BMC Neurology, 11(121):1-8 (2011).
Akhapkina et al., "Fundamentals of the modulatatory concept and classification of modulatog drugs," Breast Cancer, 19:93 (2012) (40 pages) (English language translation).
U.S. Appl. No. 17/947,844, filed Sep. 19, 2022, Michael C. Quirk.
U.S. Appl. No. 18/106,073, filed Feb. 6, 2023, Francesco G. Salituro.
U.S. Appl. No. 15/742,425, filed Jan. 5, 2018, Francesco G. Salituro et al.
U.S. Appl. No. 16/902,730, filed Jun. 16, 2020, Boyd L. Harrison et al.
U.S. Appl. No. 15/742,426, filed Jan. 5, 2018, Francesco G. Salituro et al.
U.S. Appl. No. 16/943,649, filed Jul. 30, 2020, Francesco G. Salituro.
U.S. Appl. No. 14/775,401, filed Sep. 11, 2015, Kiran Reddy et al.
U.S. Appl. No. 15/319,504, filed Dec. 16, 2016, Boyd L. Harrison et al.
U.S. Appl. No. 16/028,790, filed Jul. 6, 2018, Boyd L. Harrison et al.
U.S. Appl. No. 16/920,730, filed Jun. 16, 2020, Boyd L. Harrison et al.
U.S. Appl. No. 18/116,557, filed Mar. 2, 2023, Boyd L. Harrison et al.
U.S. Appl. No. 14/343,603, filed Nov. 25, 2014, Ravindra B. Upasani et al.
U.S. Appl. No. 16/114,791, filed Aug. 28, 2018, Ravindra B. Upasani et al.
U.S. Appl. No. 16/942,235, filed Jul. 29, 2020, Ravindra B. Upasani et al.
U.S. Appl. No. 17/707,303, filed Mar. 29, 2022, Ravindra B. Upasani et al.
U.S. Appl. No. 14/775,678, filed Sep. 12, 2015, Gabriel Martinez Botella et al.
U.S. Appl. No. 15/588,305, filed May 5, 2017, Gabriel Martinez Botella et al.
U.S. Appl. No. 15/917,263, filed Mar. 9, 2018, Gabriel Martinez Botella et al.
U.S. Appl. No. 15/917,272, filed Mar. 9, 2018, Gabriel Martinez Botella et al.
U.S. Appl. No. 16/227,013, filed Dec. 20, 2018, Gabriel Martinez Botella et al.
U.S. Appl. No. 17/381,829, filed Jul. 21, 2021, Gabriel Martinez Botella et al.
U.S. Appl. No. 15/517,886, filed Apr. 7, 2017, Michael C. Quirk et al.
U.S. Appl. No. 17/947,844, filed Sep. 19, 2022, Michael C. Quirk et al.
U.S. Appl. No. 15/742,422, filed Jan. 5, 2018, Francesco G. Salituro et al.
U.S. Appl. No. 16/879,460, filed May 20, 2020, Francesco G. Salituro et al.
U.S. Appl. No. 17/749,976, filed May 20, 2022, Francesco G. Salituro et al.
U.S. Appl. No. 15/742,424, filed Jan. 5, 2018, Francesco G. Salituro et al.
U.S. Appl. No. 17/396,034, filed Aug. 6, 2021, Francesco G. Salituro et al.
U.S. Appl. No. 18/216,057, filed Mar. 6, 2023, Francesco G. Salituro et al.
U.S. Appl. No. 16/227,099, filed Dec. 20, 2018, Francesco G. Salituro et al.
U.S. Appl. No. 16/942,245, filed Jul. 29, 2020, Francesco G. Salituro et al.
U.S. Appl. No. 16/315,250, filed Jan. 4, 2019, Francesco G. Salituro et al.
U.S. Appl. No. 16/943,649, filed Jul. 30, 2020, Francesco G. Salituro et al.
U.S. Appl. No. 16/099,122, filed Nov. 5, 2018, Gabriel Martinez Botella et al.
U.S. Appl. No. 16/930,047, filed Jul. 15, 2020, Gabriel Martinez Botella et al.
U.S. Appl. No. 17/860,816, filed Jul. 8, 2022, Gabriel Martinez Botella et al.
U.S. Appl. No. 16/089,896, filed Sep. 28, 2018, Albert Jean Robichaud et al.
U.S. Appl. No. 16/343,235, filed Apr. 18, 2019, Francesco G. Salituro et al.
U.S. Appl. No. 17/395,155, filed Aug. 5, 2021, Francesco G. Salituro et al.
U.S. Appl. No. 16/343,238, filed Apr. 18, 2019, Francesco G. Salituro et al.
U.S. Appl. No. 17/386,364, filed Jul. 27, 2021, Francesco G. Salituro et al.

(56) References Cited

OTHER PUBLICATIONS

U.S. Appl. No. 18/106,073, filed Feb. 6, 2023, Francesco G. Salituro et al.
U.S. Appl. No. 16/338,315, filed Mar. 29, 2019, Francesco G. Salituro et al.
U.S. Appl. No. 17/476,153, filed Sep. 15, 2021, Francesco G. Salituro et al.
U.S. Appl. No. 16/938,348, filed Jul. 24, 2020, James J. Doherty.
U.S. Appl. No. 18/077,031, filed Dec. 7, 2022, James J. Doherty.
Berardelli et al., "EFNS/MDS-ES/ENS [corrected] recommendations for the diagnosis of Parkinson's disease," European Journal of Neurology, 20(1): 16-34 (2013).
Dubois et al., "Research criteria for the diagnosis of Alzheimer's disease: revising the NINCDS-ADRDA criteria," Lancet Neurology, 6(8):734-746 (2007).
Dubois et al., "Revising the definition of Alzheimer's disease: a new lexicon," Lancet Neurology, 9(11):1118-27 (2010).
Jack et al., "Hypothetical model of dynamic biomarkers of the Alzheimer's pathological cascade," Lancet Neurology, 9(1):119-128 (2010).
Jack et al., "Introduction to the recommendations from the National Institute on Aging—Alzheimer's Association workgroups on diagnostic guidelines for Alzheimer's disease," Alzheimer's & Dementia, 7(3):257-62 (2011).
Litvan et al., "MDS Task Force on mild cognitive impairment in Parkinson's disease: critical review of PD-MCI," Movement Disorders, 26(10):1814-1824 (2011).
Litvan et al., "Diagnostic criteria for mild cognitive impairment in Parkinson's disease: Movement Disorder Society Task Force guidelines," Movement Disorders, 27(3):349-56 (2012).
Nasreddine et al., "The Montreal Cognitive Assessment, MoCA: a brief screening tool for mild cognitive impairment," Journal of the American Geriatrics Society, 53(4):695-699 (2005).
Postuma et al., "MDS clinical diagnostic criteria for Parkinson's disease," Movement Disorders, 30(12):1591-601 (2015).

\* cited by examiner

OXYSTEROLS AND METHODS OF USE THEREOF

CROSS REFERENCE TO RELATED APPLICATIONS

This application is a continuation of U.S. patent application Ser. No. 16/089,896, filed Sep. 28, 2018, which is a U.S. National Phase Application under 35 U.S.C. § 371 of International Application PCT/US2017/025535, filed Mar. 31, 2017, which claims the benefit of and priority under 35 U.S.C. § 119(e) from U.S. Provisional Patent Application 62/317,002, filed Apr. 1, 2016. The disclosures of each of the foregoing applications are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators of these receptors may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators of these receptors may be useful as therapeutic agents with potential clinical uses in the treatment of psychiatric disorders in which glutamatergic transmission is pathologically increased (e.g., treatment resistant depression).

Oxysterols are cholesterol analogs that are modulators of NMDA receptor function. There is a need for new oxysterols that modulate the NMDA receptor for the prevention and treatment of conditions associated with NMDA expression and function. Compounds, compositions, and methods described herein are directed toward this end.

SUMMARY OF THE INVENTION

Provided herein are new oxysterols useful for preventing and/or treating a broad range of disorders, including, but not limited to, NMDA-mediated disorders. Further provided are pharmaceutical compositions comprising the compounds of the present invention, and methods of their use and treatment.

In one aspect, provided herein are compounds according to Formula (I-A):

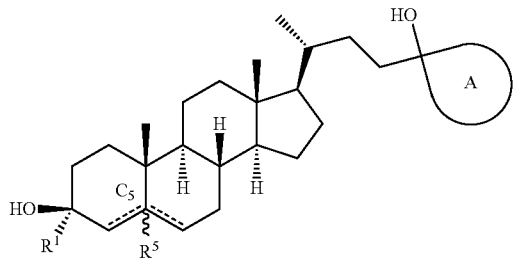

(I-A)

or a pharmaceutically acceptable salt thereof, wherein: A is carbocyclyl or heterocyclyl (e.g., unsubstituted or substituted carbocyclyl or heterocyclyl, e.g., heterocyclyl substituted with at least one heteroatom (e.g., 1, 2, or 3 heteroatoms)); $R^1$ is $C_{1-6}$ alkyl (e.g., $-CH_3$ or $-CH_2CH_3$); $R^5$ is absent or hydrogen; ═ represents a single or double bond, wherein when one ═ is a double bond, then the other ═ is a single bond and $R^5$ is absent.

In one aspect, provided herein are compounds according to Formula (I-B):

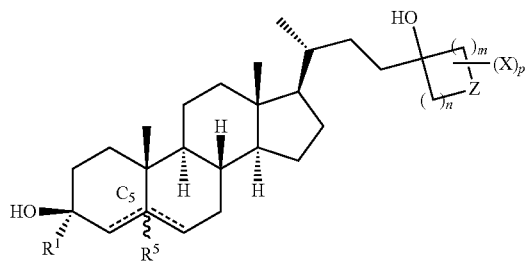

(I-B)

or a pharmaceutically acceptable salt thereof, wherein: $R^1$ is hydrogen or $C_{1-6}$ alkyl (e.g., $-CH_3$ or $-CH_2CH_3$); $R^5$ is absent or hydrogen; Z is $-C(R^A)_2-$, $-NR^B-$, $-O-$, or $-S-$; X is halogen, $C_{1-6}$ alkyl, or $-OR^C$; $R^A$ is hydrogen, halogen, or $C_{1-6}$ alkyl; $R^B$ is hydrogen, $C_{1-6}$ alkyl, $-C(O)R^C$, $-C(O)OR^C$, $-C(O)N(R^D)_2$, or $-S(O)_2R^C$; $R^C$ is hydrogen or $C_{1-6}$ alkyl; each $R^D$ is independently hydrogen, $C_{1-6}$ alkyl, aryl, or heteroaryl; m is an integer selected from 1, 2, and 3; n is an integer selected from 1, 2, and 3; p is an integer selected from 0, 1, 2, 3, 4, and 5; and ═ represents a single or double bond, wherein when one ═ is a double bond, then the other ═ is a single bond and $R^5$ is absent.

In some embodiments, the compound is a compound of Formula (II-A), Formula (II-B), or Formula (II-C):

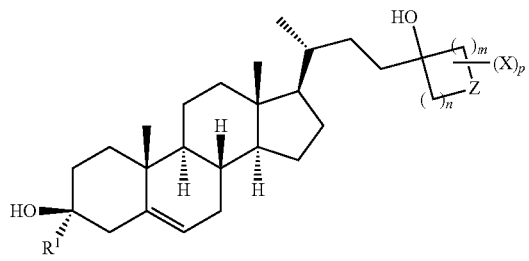

(II-A)

-continued

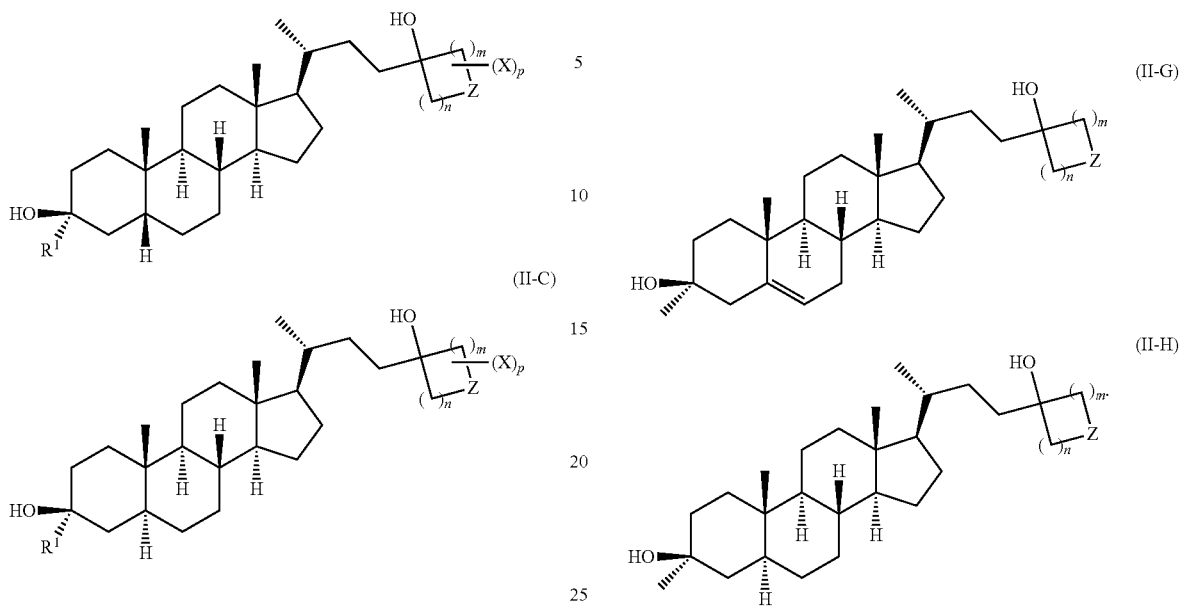

In some embodiments, p is an integer selected from 0, 1, or 2. In some embodiments, p is 0. In some embodiments, p is 1. In some embodiments, p is 1 and X is halogen.

In some embodiments, the compound is of Formula (II-D), Formula (II-E), or Formula (II-F):

In some embodiments, the compound is of Formula (II-G) or Formula (II-H):

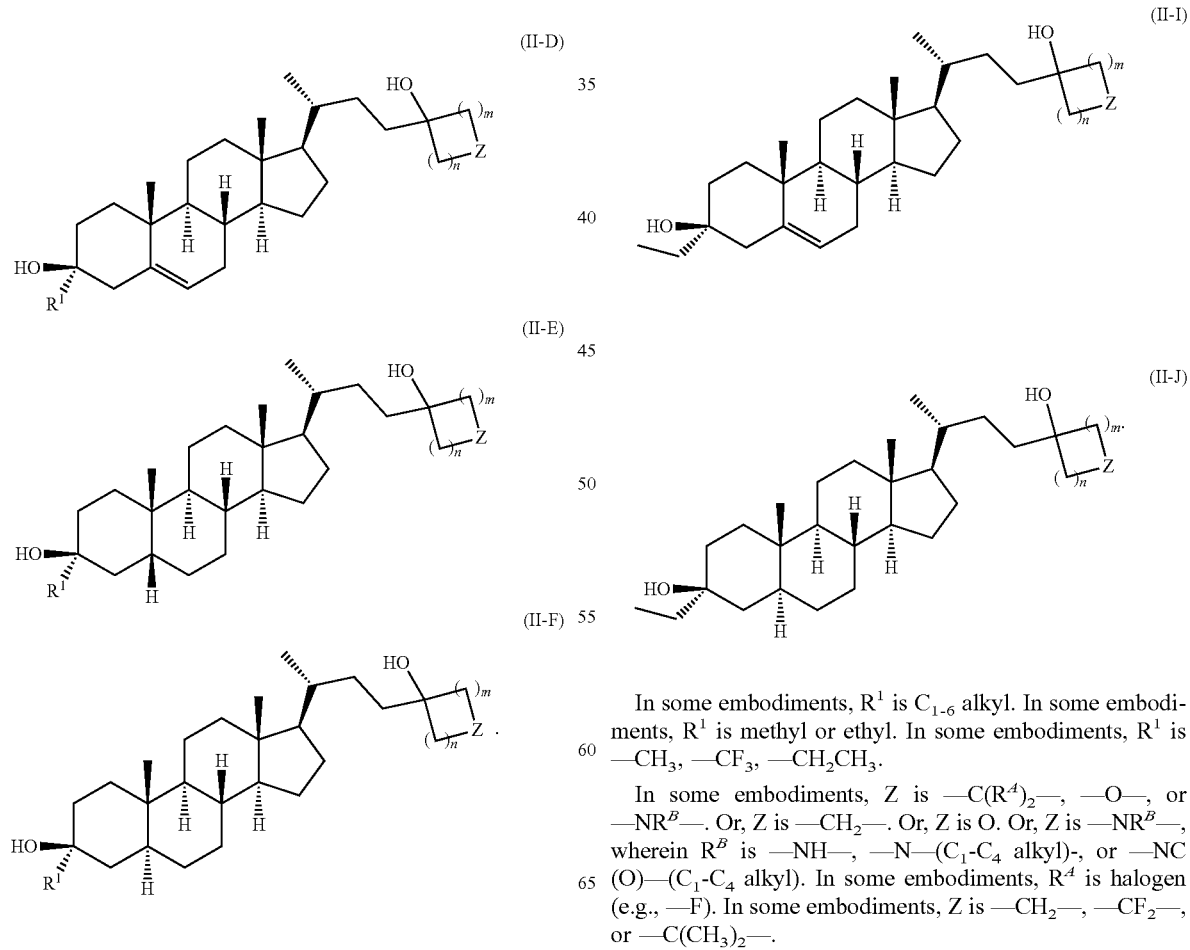

In some embodiments, the compound is of Formula (II-I) or Formula (II-J):

In some embodiments, $R^1$ is $C_{1-6}$ alkyl. In some embodiments, $R^1$ is methyl or ethyl. In some embodiments, $R^1$ is —$CH_3$, —$CF_3$, —$CH_2CH_3$.

In some embodiments, Z is —$C(R^A)_2$—, —O—, or —$NR^B$—. Or, Z is —$CH_2$—. Or, Z is O. Or, Z is —$NR^B$—, wherein $R^B$ is —NH—, —N—($C_1$-$C_4$ alkyl)-, or —NC(O)—($C_1$-$C_4$ alkyl). In some embodiments, $R^A$ is halogen (e.g., —F). In some embodiments, Z is —$CH_2$—, —$CF_2$—, or —$C(CH_3)_2$—.

In some embodiments, the compound is:
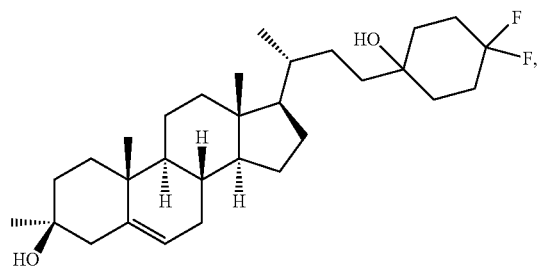
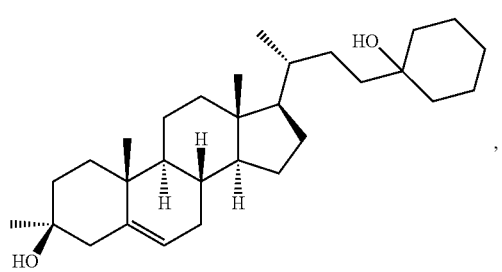
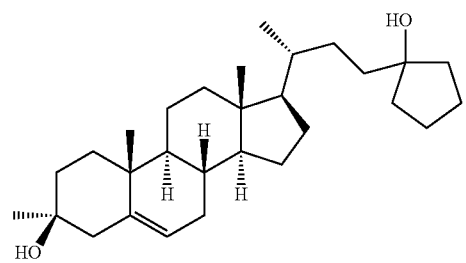
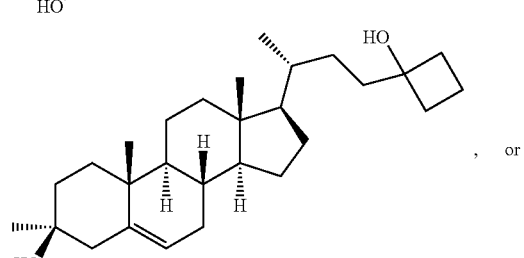
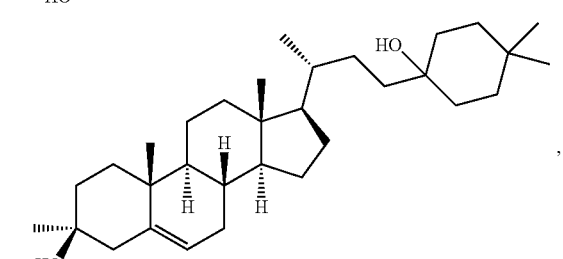,
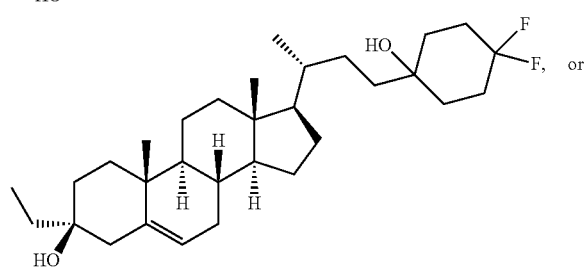, or
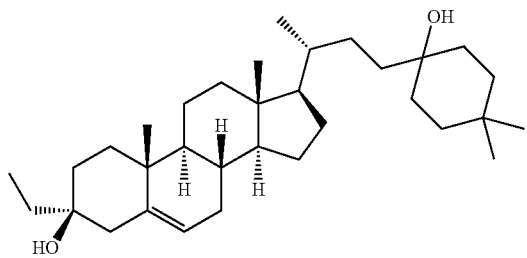.
In some embodiments, the compound is:
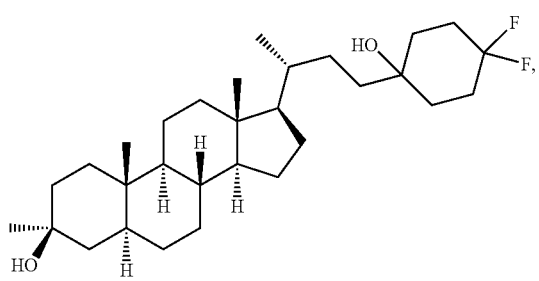,
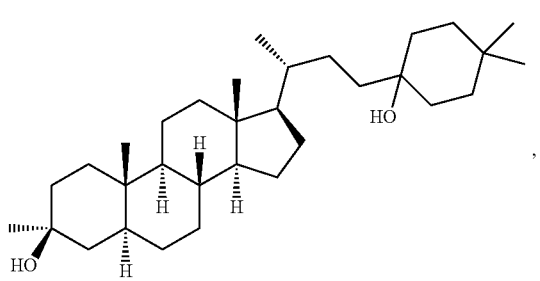,
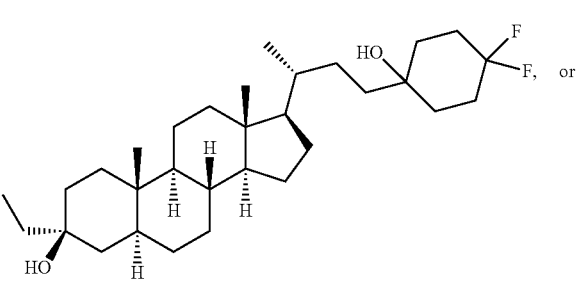, or
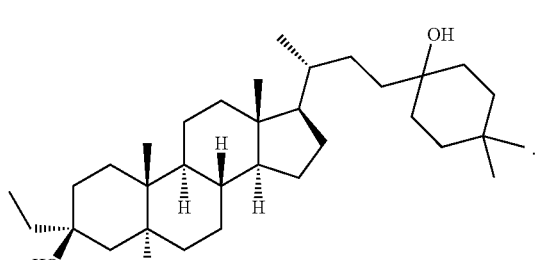.
In some embodiments, Z is —O— or —NR$^B$—.

In some embodiments, the compound is:
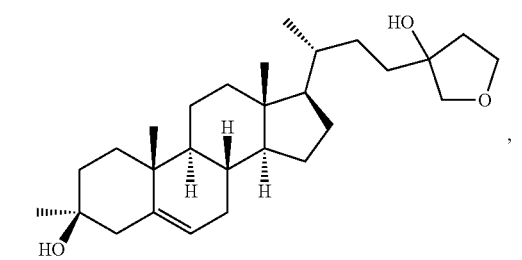
,
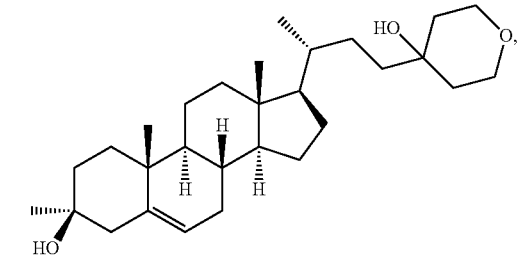
,
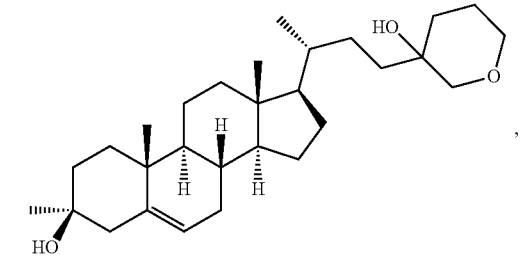
,
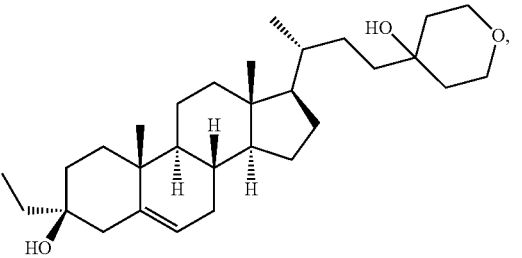
, or
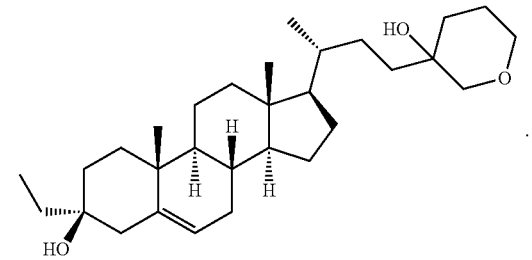
In some embodiments, the compound is:
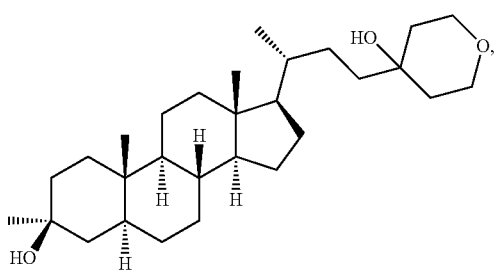
,
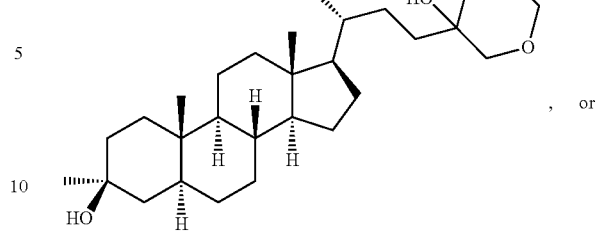
, or
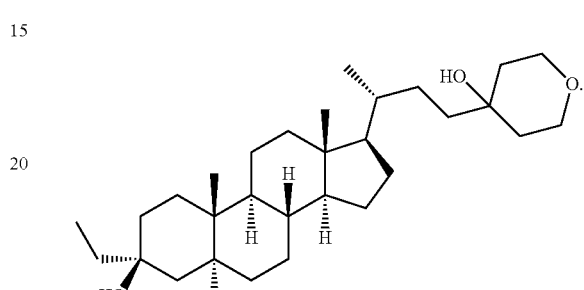
.
In some embodiments, the compound is:
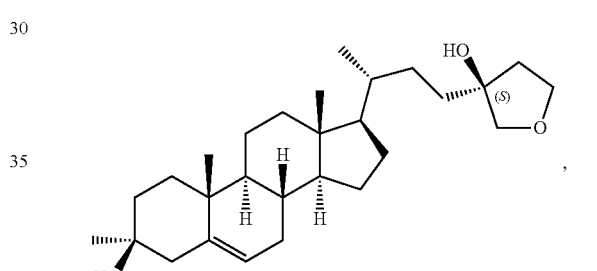
,
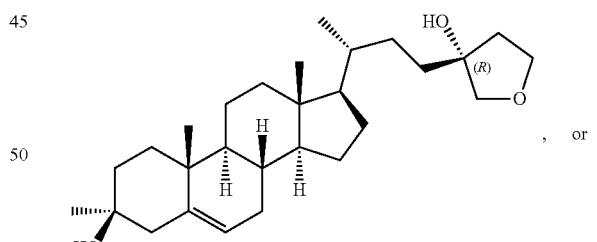
, or
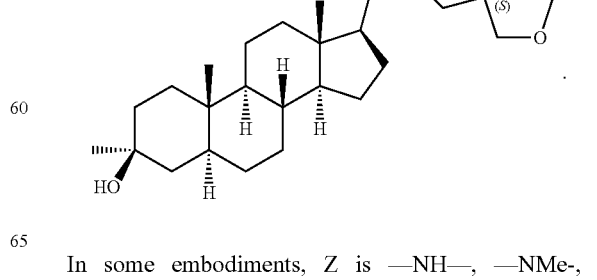
.
In some embodiments, Z is —NH—, —NMe-, or —NAc—.

In some embodiments, the compound is:
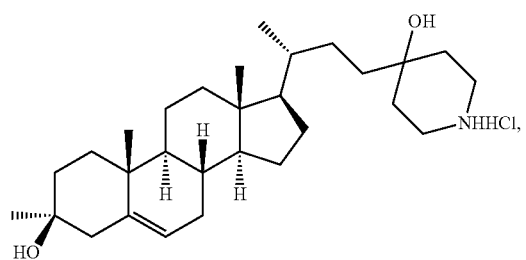
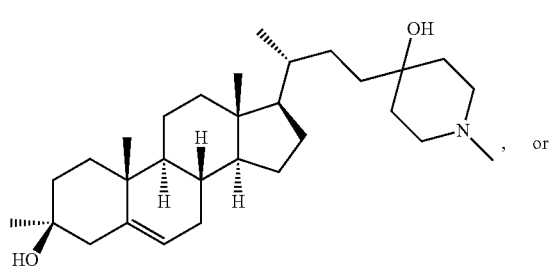
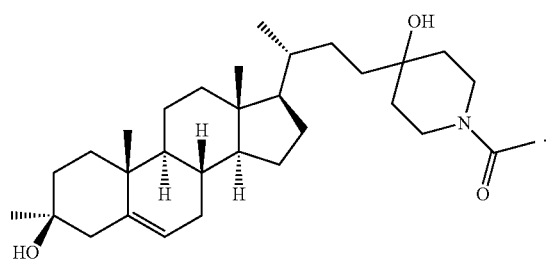
In some embodiments, Z is —CH$_2$—. In some embodiments, Z is —C(CH$_3$)$_2$—. In some embodiments, Z is —CF$_2$—. In some embodiments, m is 1, n is 2, and Z is —O—. In some embodiments, m is 2 and n is 2. In some embodiments, m is 3 and n is 1. In some embodiments, m is 3, n is 1, and Z is —O—. In some embodiments, m is 2, n is 2, and Z is —O— or —NR$^B$—.
In some embodiments, the compound is:
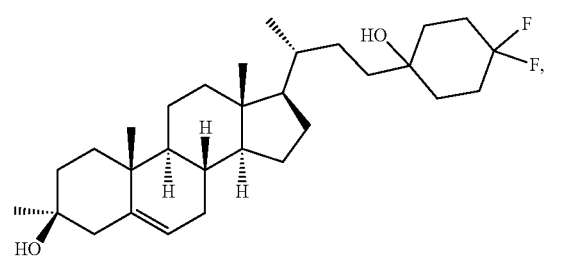
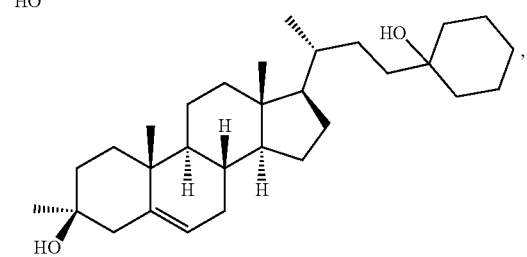
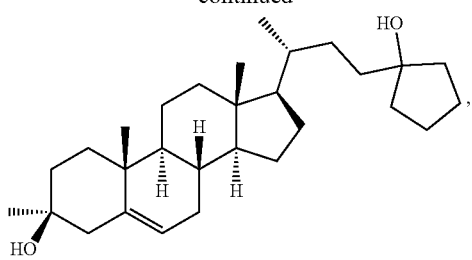
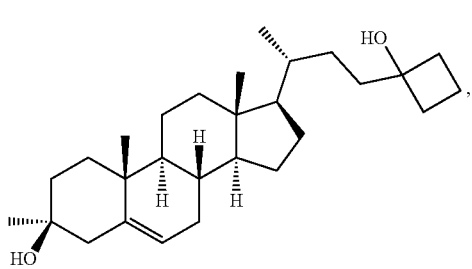
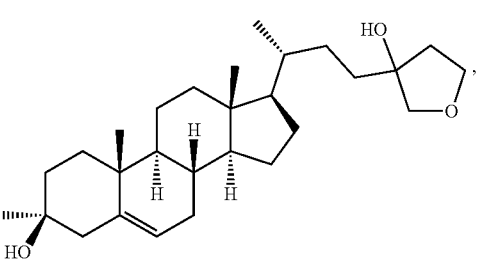
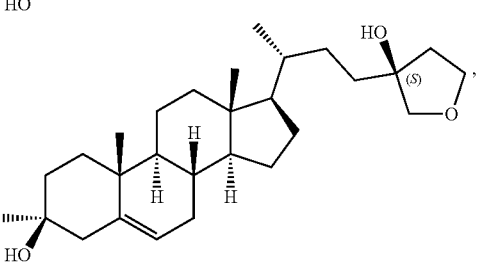
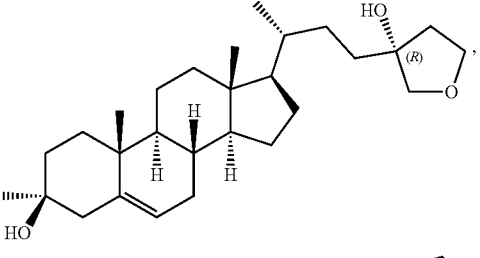
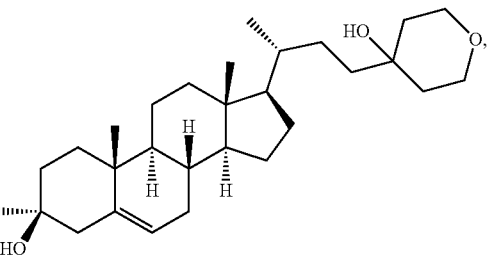

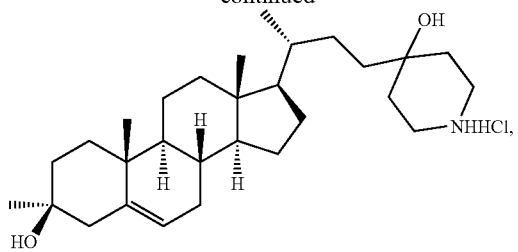
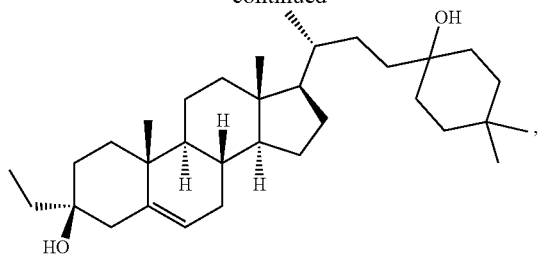
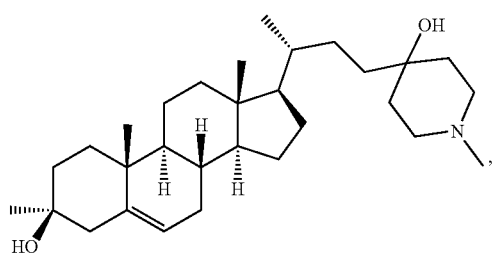
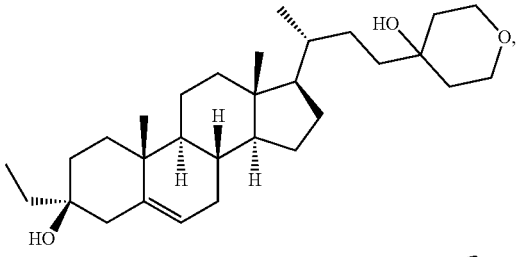
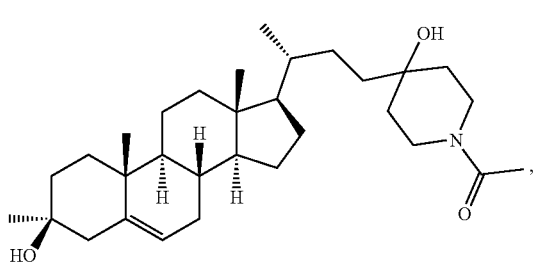
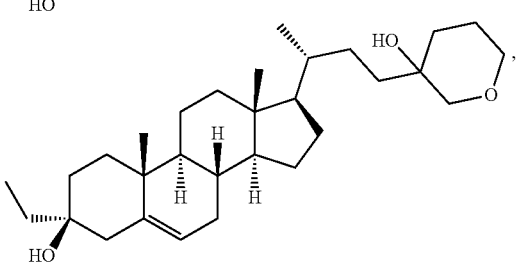
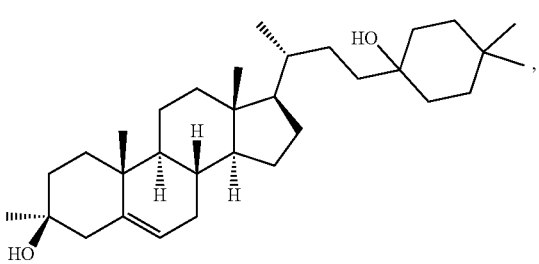
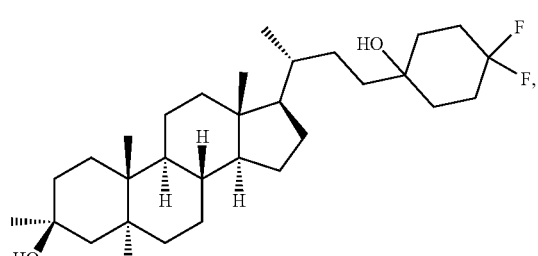
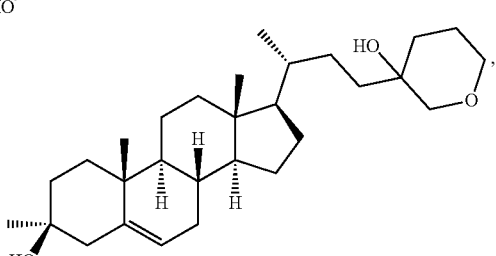
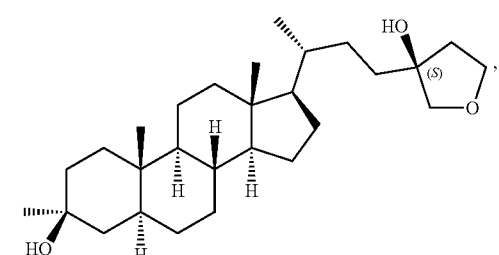
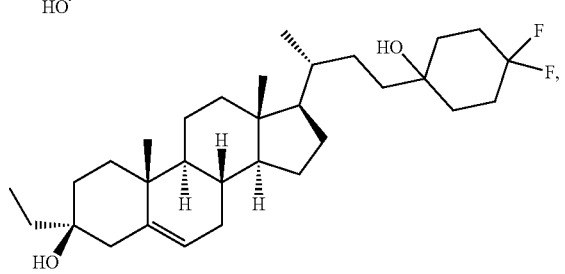
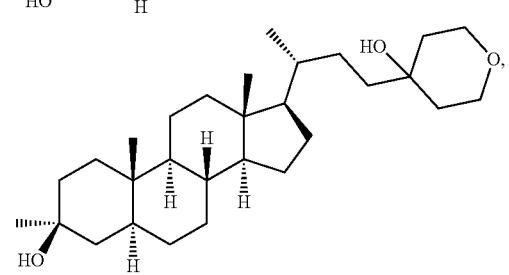

-continued
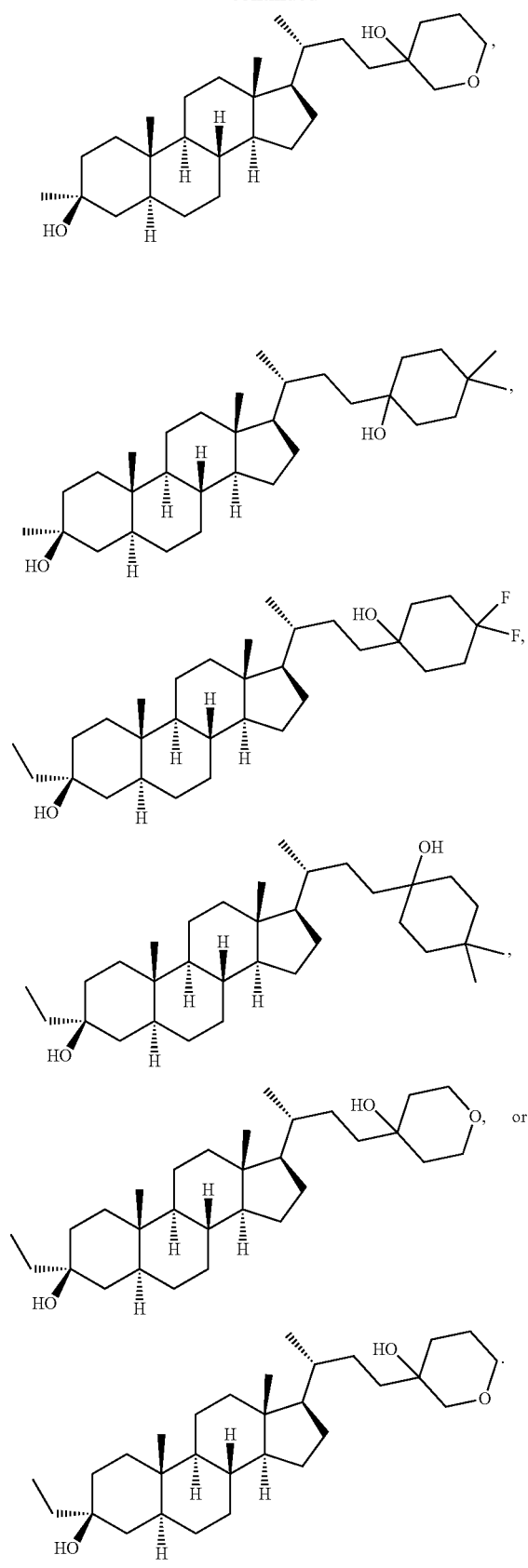
In some embodiments, the compound is a pharmaceutically acceptable salt of:
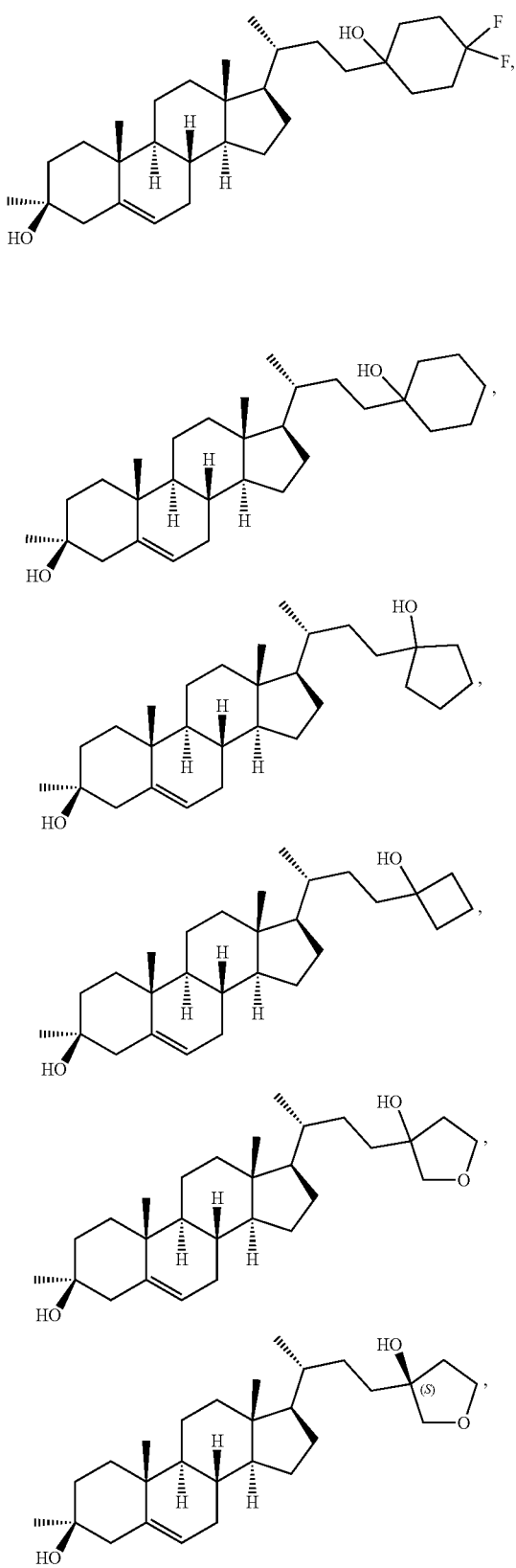

-continued
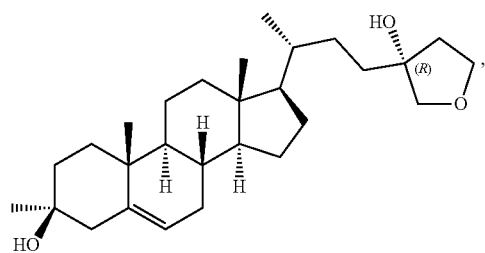
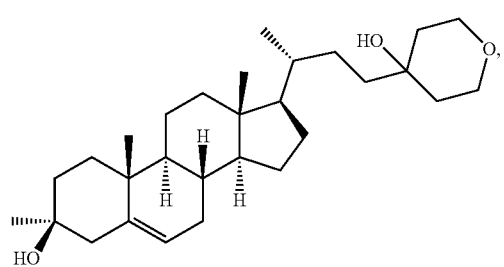
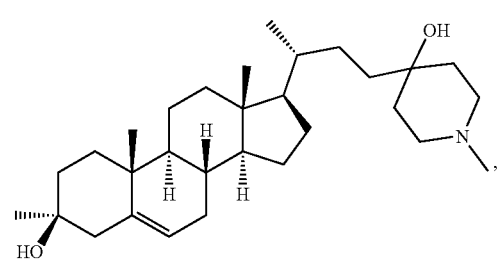
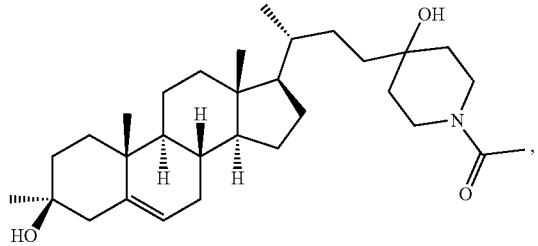
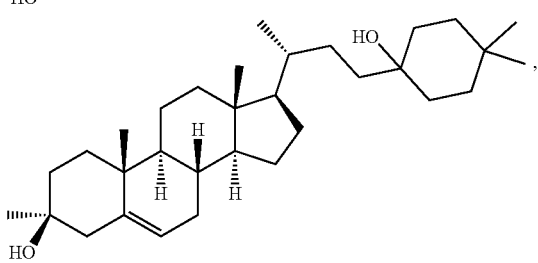
-continued
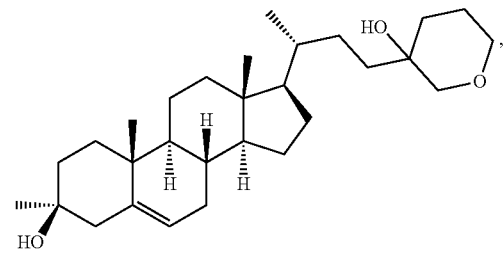
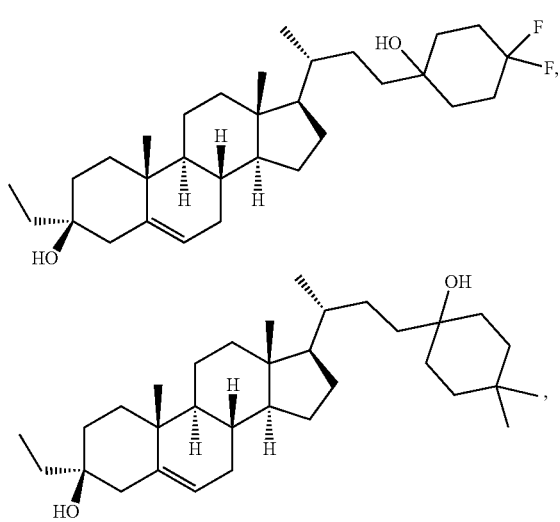
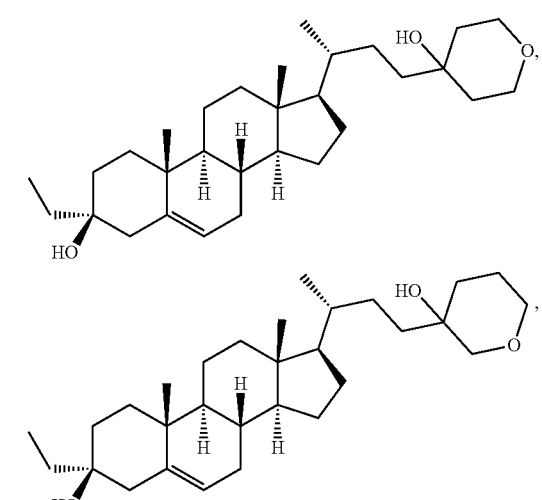
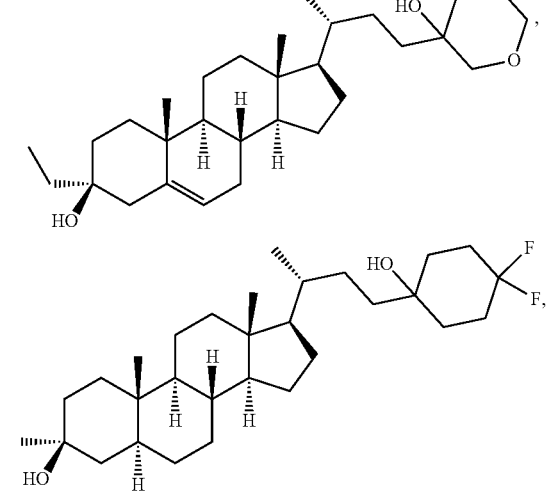

-continued

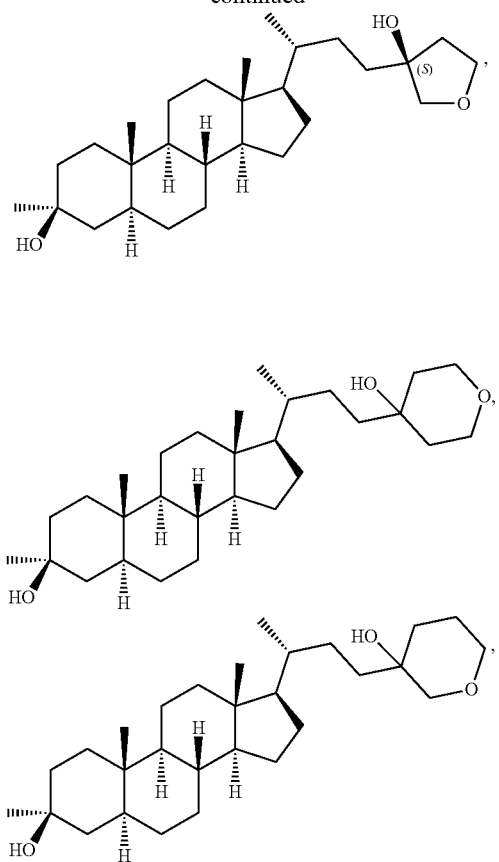

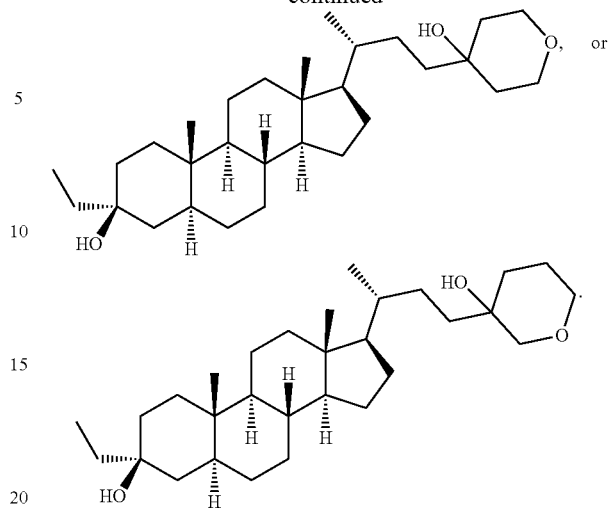

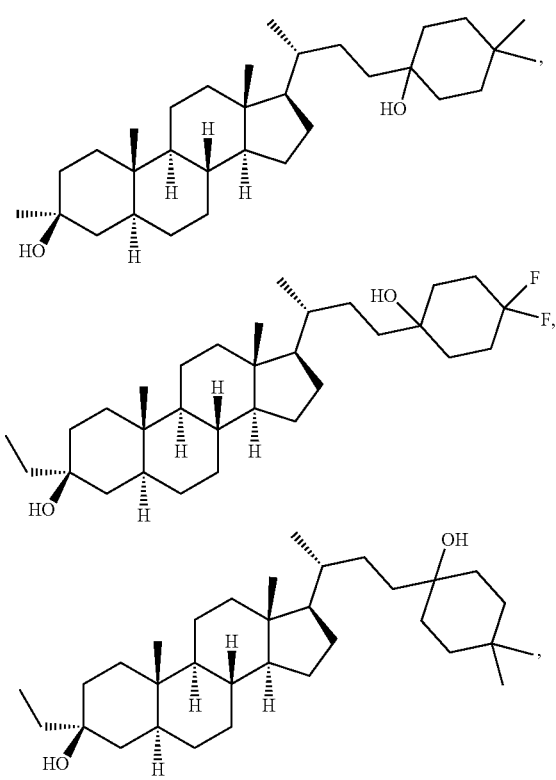

In one aspect, provided herein is a pharmaceutical composition comprising a compound as described herein (e.g., a compound of Formula (I-A) (I-B), (II-A), (II-B), (IT-C), (II-D), (II-E), (II-F), (II-G), (II-H), (II-I), or (II-J)), or pharmaceutically acceptable salt thereof, and a pharmaceutically acceptable carrier.

In another aspect, provided herein is a method of inducing sedation or anesthesia comprising administering to a subject an effective amount of a compound as described herein (e.g., a compound of Formula (I-A) (I-B), (II-A), (II-B), (II-C), (II-D), (II-E), (II-F), (II-G), (II-H), (II-I), or (II-J)), or pharmaceutically acceptable salt thereof, or pharmaceutical composition thereof.

In one aspect, provided herein is a method for treating or preventing a disorder described herein, comprising administering to a subject in need thereof an effective amount of a compound as described herein (e.g., a compound of Formula (I-A) (I-B), (II-A), (II-B), (II-C), (II-D), (II-E), (II-F), (II-G), (II-H), (II-I), or (II-J)), or pharmaceutically acceptable salt thereof, or pharmaceutical composition thereof.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In some embodiments, the disorder is a metabolic disorder.

In one aspect, provided herein is a method for treating or preventing a CNS-related condition comprising administering to a subject in need thereof an effective amount of a compound as described herein (e.g., a compound of Formula (I-A) (I-B), (II-A), (II-B), (II-C), (II-D), (II-E), (II-F), (II-G), (II-H), (II-I), or (II-J)), or pharmaceutically acceptable salt thereof, or pharmaceutical composition thereof.

In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

In some embodiments, the disorder is sterol synthesis disorder.

In one aspect, provided herein is a method for treating or preventing Smith-Lemli-Opitz Syndrome (SLOS), Desmosterolosis, Sitosterolemia, Cerebrotendinous xanthomatosis (CTX), Mevalonate Kinase Deficiency Syndromes (MKD), SC4MOL gene mutation (SMO Deficiency), Niemann-Pick disease, Autism Disorders Associated with Phenylketonuria, comprising administering to a subject in need thereof an effective amount of a compound as described herein (e.g., a compound of Formula (I-A) (I-B), (II-A), (II-B), (II-C), (II-D), (II-E), (II-F), (II-G), (II-H), (II-I), or (II-J)), or a pharmaceutically acceptable salt thereof, or pharmaceutical composition thereof.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein (e.g., a compound of Formula (I-A) (I-B), (II-A), (II-B), (II-C), (II-D), (II-E), (II-F), (II-G), (II-H), (II-I), or (II-J)), or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia), dissociative disorder, eating disorder, mood disorder (including depression (e.g., postpartum depression), bipolar disorder, dysthymic disorder, suicidality, schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

In one embodiment, a stereoisomer described herein is enriched in the stereoisomeric form depicted for that compound. For example, the stereoisomer can have an enantiomeric excess or diastereomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

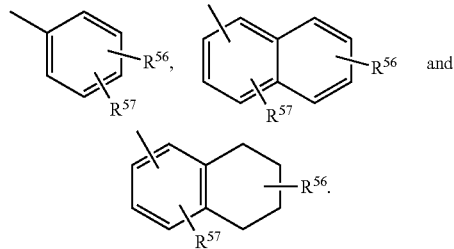

wherein one of $R^{56}$ and $R^{57}$ may be hydrogen and at least one of $R^{56}$ and $R^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SO$_2$alkyl, SO$_2$alkyl, Saryl, SOaryl, SO$_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, C$_1$-C$_8$ alkyl, C$_1$-C$_4$haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

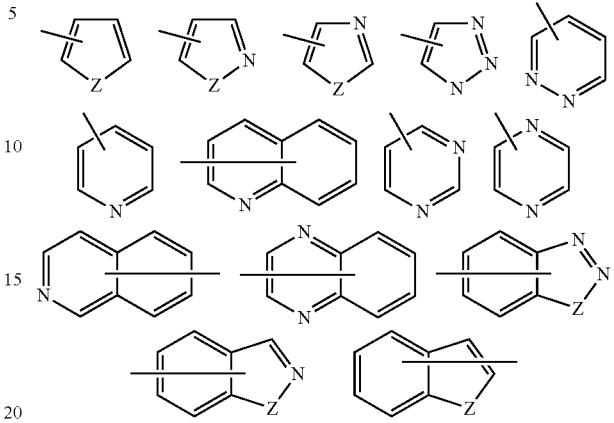

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, $R^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethyl-butoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$—cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both $R^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each $R^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two RU groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{C}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Abbreviations

AcCl: acetyl chloride; 9-BBN: 9-borabicyclo[3.3.1]nonane; BHT: 2,6-di-t-butyl-p-cresol (butylated hydroxytoluene); Boc: t-butoxycarbonyl; DCE: dichloroethane; DCM: dichloromethane; DMF: N,N-dimethylformamide; DMP: Dess-Martin periodinane; DMSO: dimethylsulfoxide; EtOAc: ethylacetate; i-PrMgCP: Isopropylmagnesium chloride; MAD: methyl aluminum bis(2,6-di-t-butyl-4-methylphenoxide); m-CPBA: meta chloroperbenzoic acid; Me$_3$SI: Trimethylsulfonium iodide; MTBE: methyl tert-butyl ether; Na$_2$SO$_4$: sodium sulfate; n-BuLi: n-Butyl lithium; PCC: pyridinium chlorochromate; Pd(t-Bu$_3$P)$_2$: bis(tri-tert-butylphosphine)palladium(0); PE: petroleum ether; py: pyridine; TBAF: tetra-n-butylammonium fluoride; t-BuOK: potassium tert-butoxide; TBSCl: tert-Butyl(chloro)dimethylsilane; TFA: trifluoroacetic acid; THF: tetrahydrofuran; Ts: p-toluenesulfonyl; (i-PrO)$_4$Ti: titanium tetraisopropoxide.

DETAILED DESCRIPTION OF CERTAIN EMBODIMENTS OF THE INVENTION

As generally described herein, the present invention provides new oxysterols useful for preventing and/or treating a broad range of disorders, including, but not limited to, NMDA-mediated disorders.

Compounds

In one aspect, provided herein are compounds according to Formula (I-A):

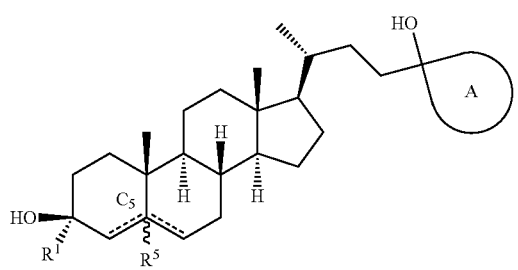

(I-A)

or a pharmaceutically acceptable salt thereof, wherein: A is carbocyclyl or heterocyclyl (e.g., unsubstituted or substituted carbocyclyl or heterocyclyl, e.g., heterocyclyl substituted with at least one heteroatom (e.g., 1, 2, or 3 heteroatoms)); $R^1$ is $C_{1-6}$ alkyl (e.g., —CH$_3$ or —CH$_2$CH$_3$); $R^5$ is absent or hydrogen; ═══ represents a single or double bond, wherein when one ═══ is a double bond, then the other ═══ is a single bond and $R^5$ is absent.

In one aspect, provided herein are compounds according to Formula (I-B):

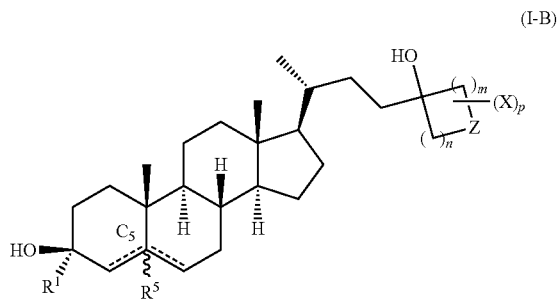

(I-B)

or a pharmaceutically acceptable salt thereof, wherein: $R^1$ is hydrogen or $C_{1-6}$ alkyl (e.g., —CH$_3$ or —CH$_2$CH$_3$); $R^5$ is absent or hydrogen; Z is —C(R$^A$)$_2$—, —NR$^B$—, —O—, or —S—; X is halogen, $C_{1-6}$ alkyl, or —OR$^C$; $R^A$ is hydrogen, halogen, or $C_{1-6}$ alkyl; $R^B$ is hydrogen, $C_{1-6}$ alkyl, —C(O)R$^C$, —C(O)OR$^C$, —C(O)N(R$^D$)$_2$, or —S(O)$_2$R$^C$; $R^C$ is hydrogen or $C_{1-6}$ alkyl; each $R^D$ is independently hydrogen, $C_{1-6}$ alkyl, aryl, or heteroaryl; m is an integer selected from 1, 2, and 3; n is an integer selected from 1, 2, and 3; p is an integer selected from 0, 1, 2, 3, 4, and 5; and ═══ represents a single or double bond, wherein when one ═══ is a double bond, then the other ═══ is a single bond and $R^5$ is absent.

In some embodiments, the compound is a compound of Formula (II-A), Formula (II-B), or Formula (II-C):

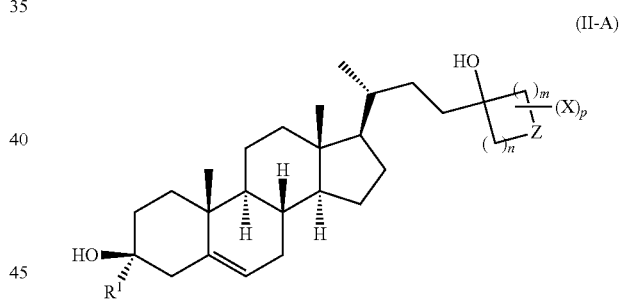

(II-A)

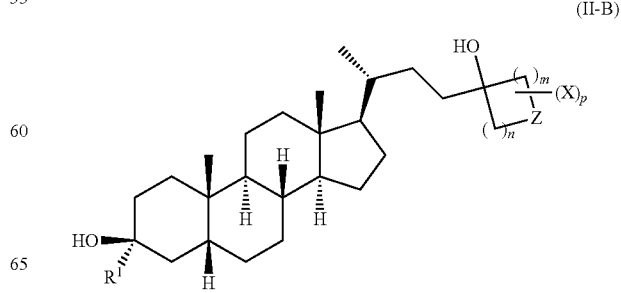

(II-B)

-continued

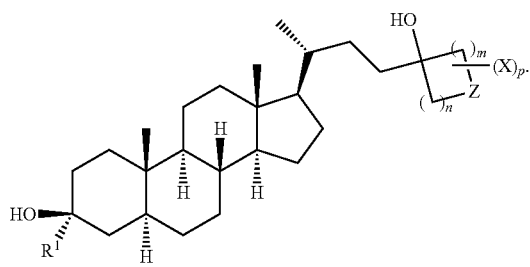
(II-C)

In some embodiments, p is an integer selected from 0, 1, or 2. In some embodiments, p is 0. In some embodiments, p is 1. In some embodiments, p is 1 and X is halogen.

In some embodiments, the compound is of Formula (II-D), Formula (II-E), or Formula (II-F):

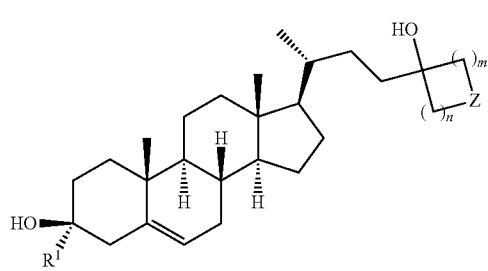
(II-D)

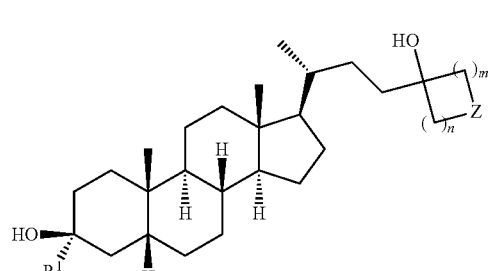
(II-E)

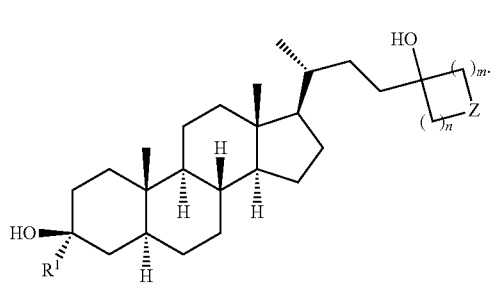
(II-F)

In some embodiments, the compound is of Formula (II-G) or Formula (II-H):

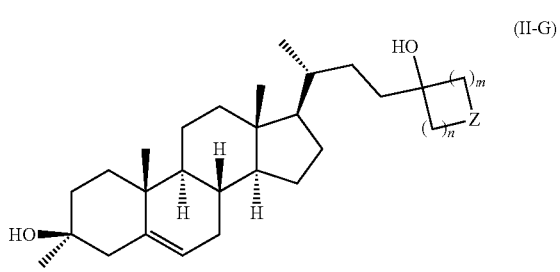
(II-G)

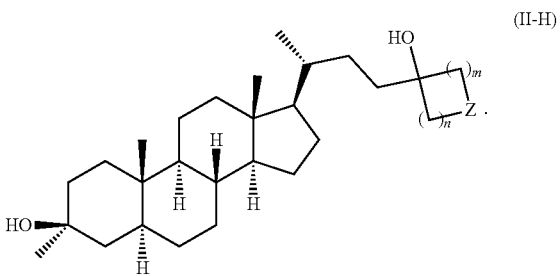
(II-H)

In some embodiments, the compound is of Formula (II-I) or Formula (II-J):

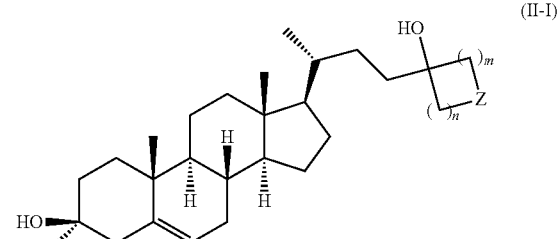
(II-I)

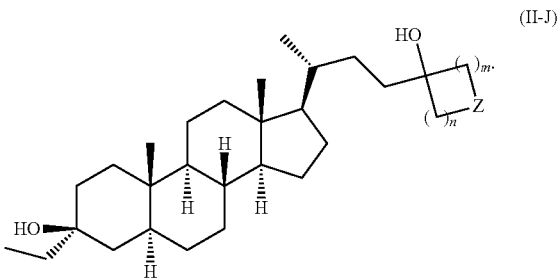
(II-J)

In some embodiments, $R^1$ is $C_{1-6}$ alkyl. In some embodiments, $R^1$ is methyl or ethyl. In some embodiments, R is —$CH_3$, —$CF_3$, —$CH_2CH_3$.

In some embodiments, Z is —$C(R^A)_2$—, —O—, or —$NR^B$—. Or, Z is —$CH_2$—. Or, Z is O. Or, Z is —$NR^B$—, wherein $R^B$ is —NH—, —N—($C_1$-$C_4$ alkyl)-, or —NC(O)—($C_1$-$C_4$ alkyl). In some embodiments, $R^A$ is halogen (e.g., —F). In some embodiments, Z is —$CH_2$—, —$CF_2$—, or —$C(CH_3)_2$—.

In some embodiments, the compound is:
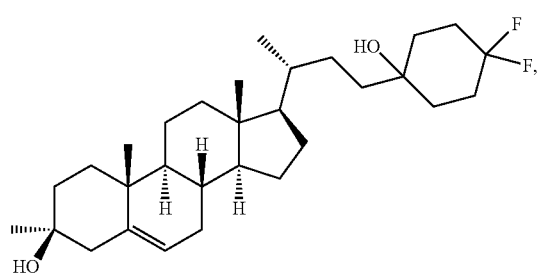
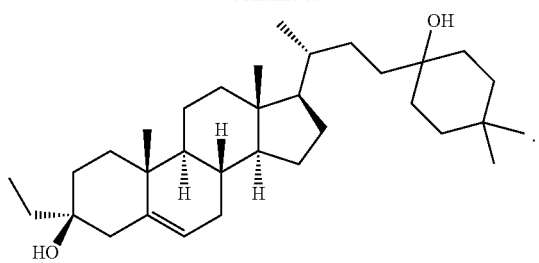
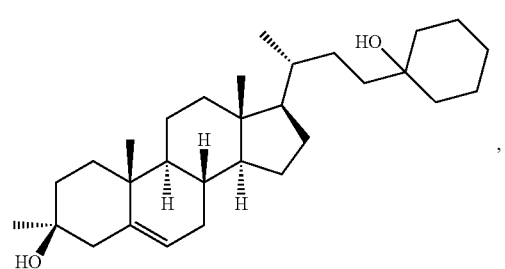
In some embodiments, the compound is:
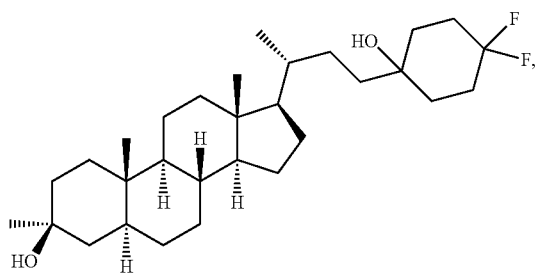
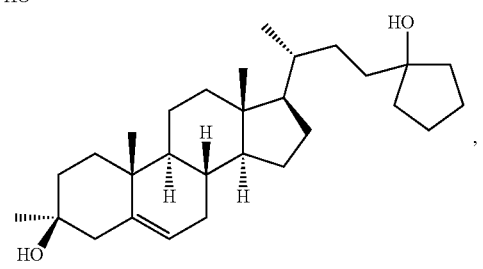
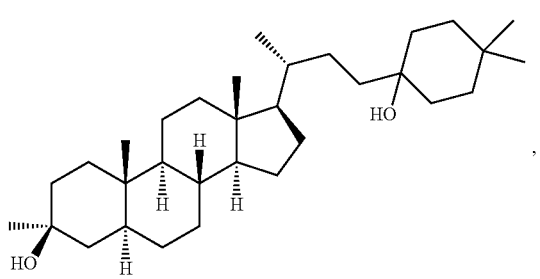
, or
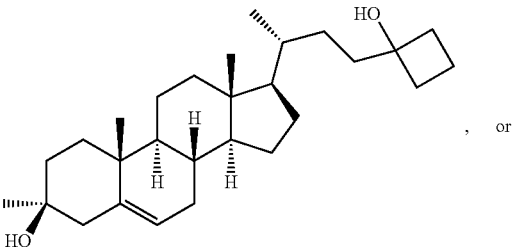
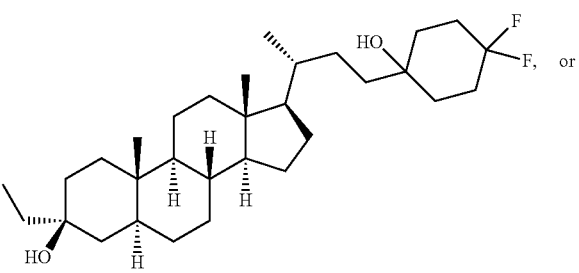
,
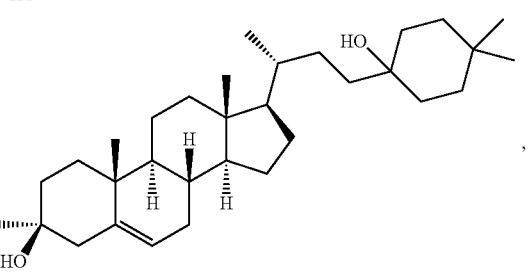
, or
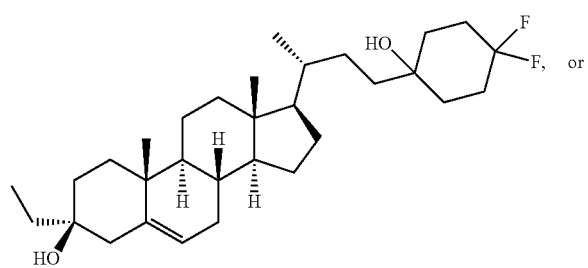
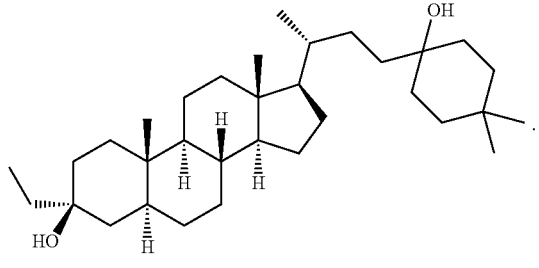
.
In some embodiments, Z is —O— or —NR$^B$—.

In some embodiments, the compound is:
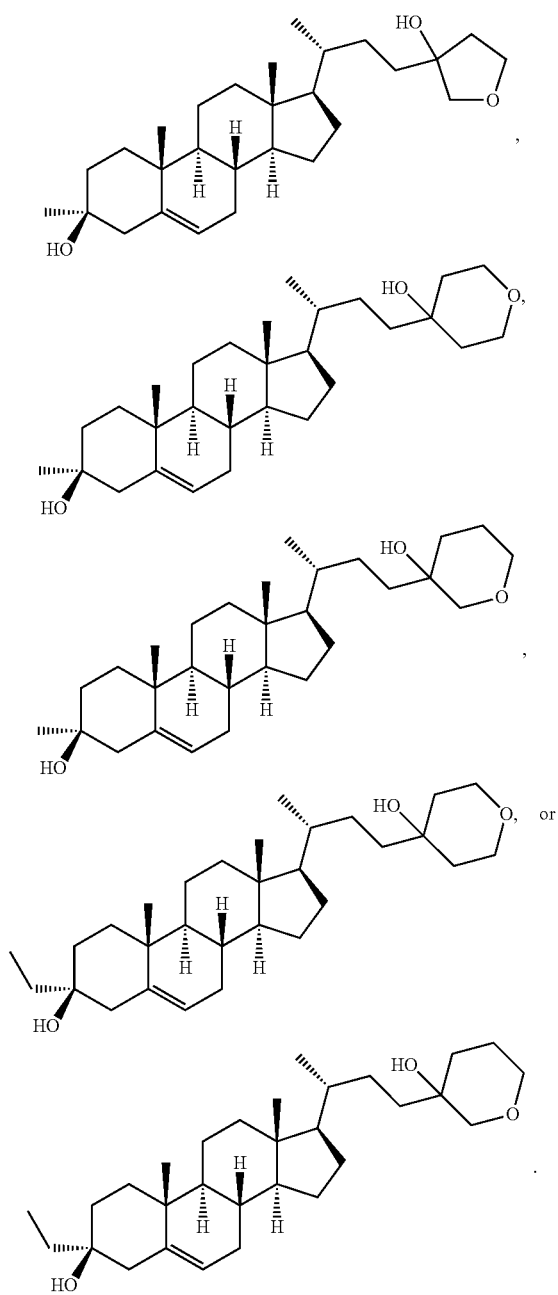
In some embodiments, the compound is:
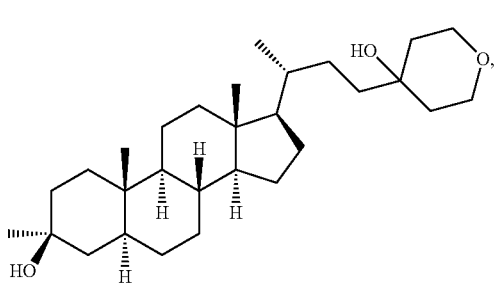
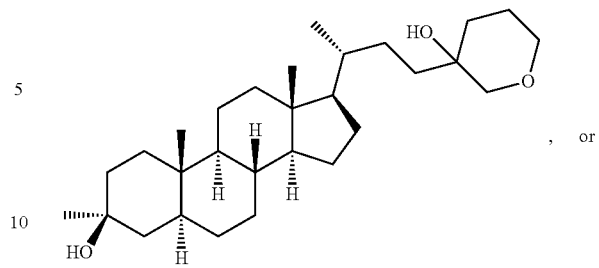
, or
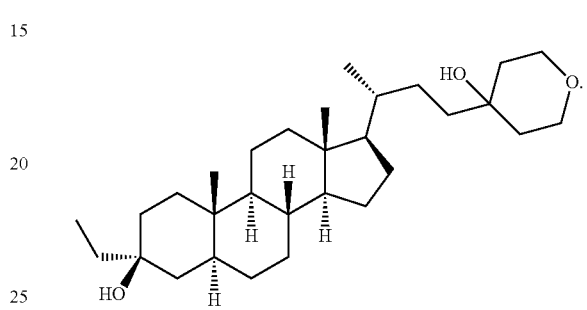
In some embodiments, the compound is:
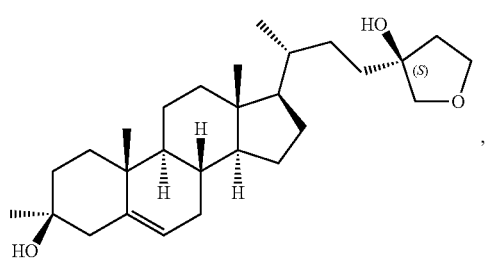
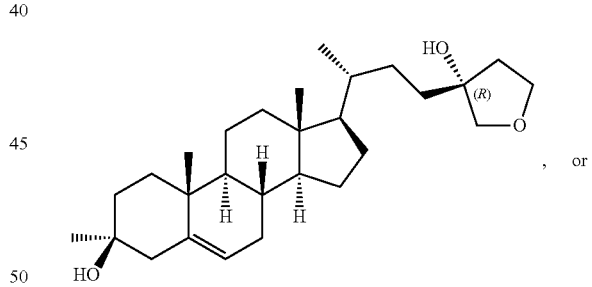
, or
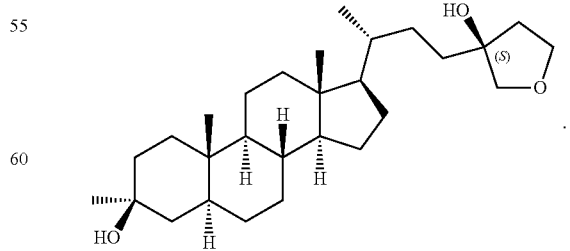
In some embodiments, Z is —NH—, —NMe-, or —NAc—.

In some embodiments, the compound is:
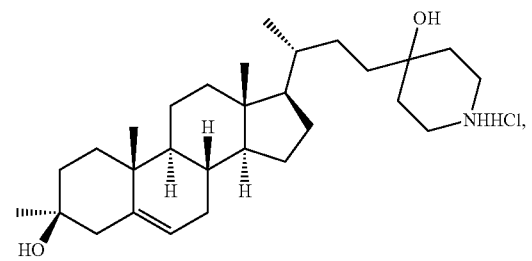
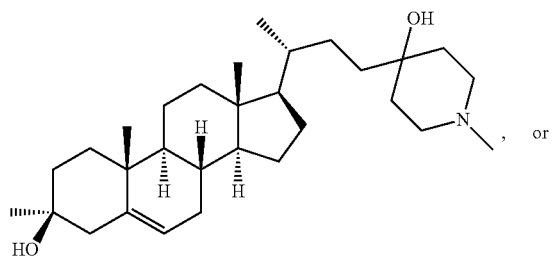, or
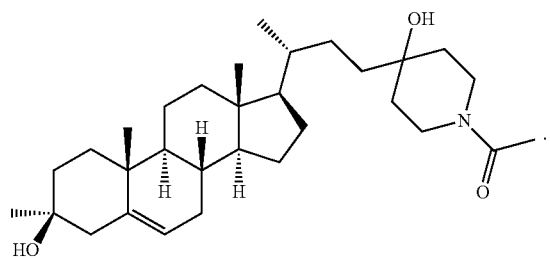.
In some embodiments, Z is —CH$_2$—. In some embodiments, Z is —C(CH$_3$)$_2$—. In some embodiments, Z is —CF$_2$—. In some embodiments, m is 1, n is 2, and Z is —O—. In some embodiments, m is 2 and n is 2. In some embodiments, m is 3 and n is 1. In some embodiments, m is 3, n is 1, and Z is —O—. In some embodiments, m is 2, n is 2, and Z is —O— or —NR$^B$—.
In some embodiments, the compound is:
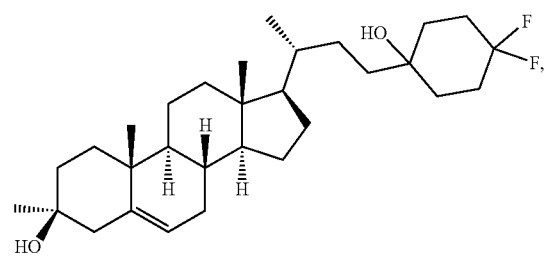,
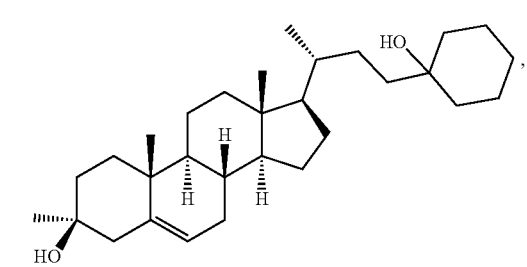,
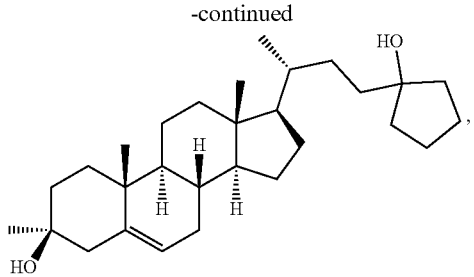,
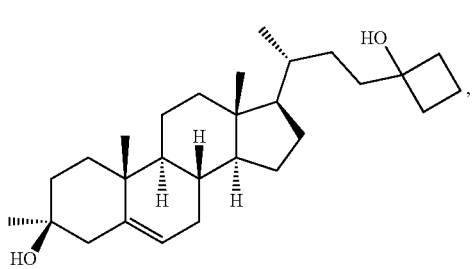,
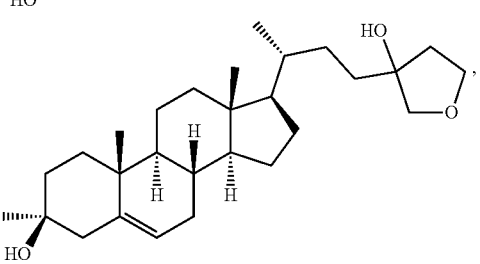,
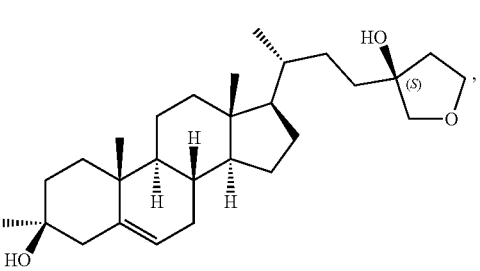,
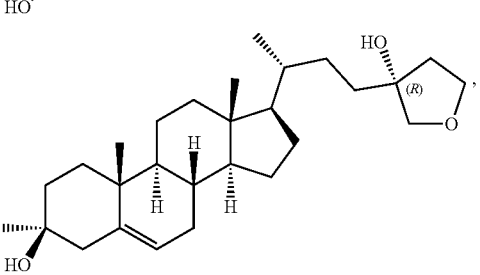,
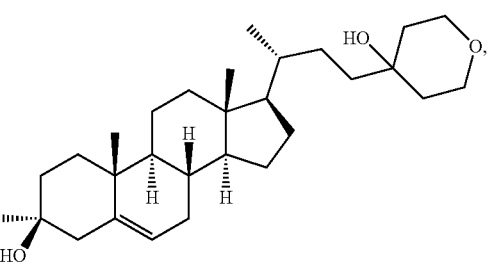, -continued
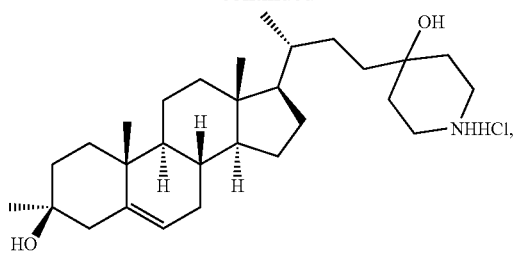
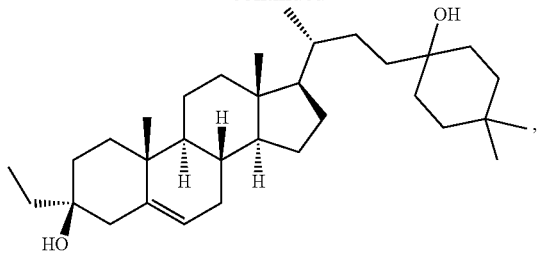
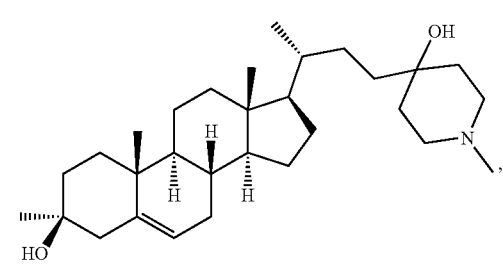
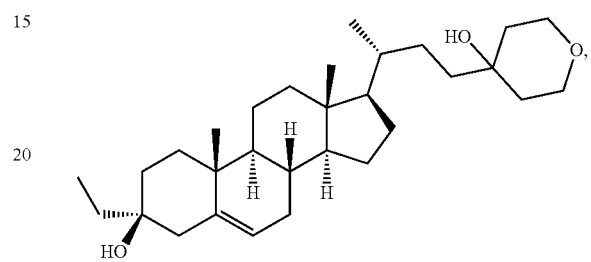
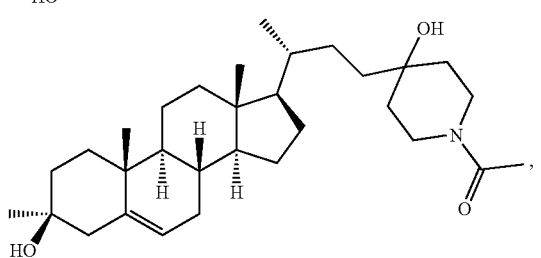
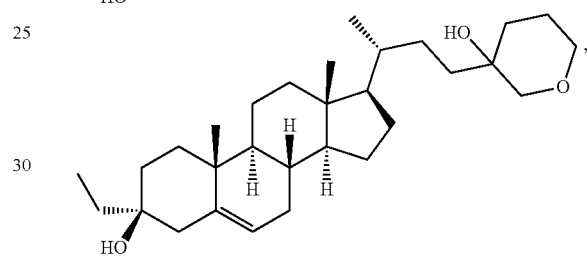
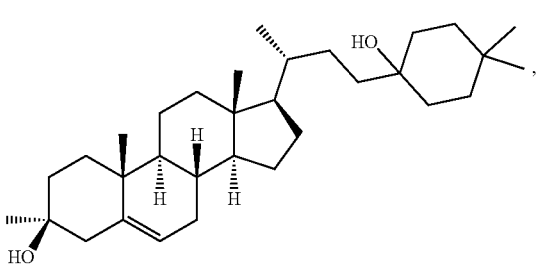
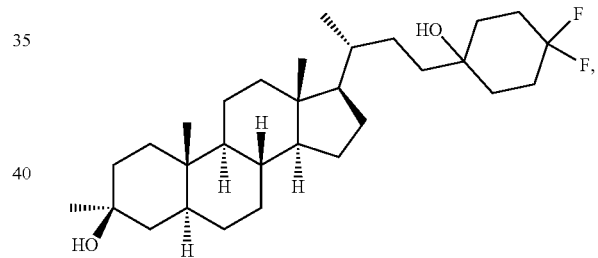
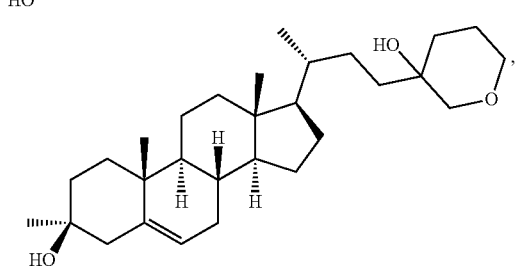
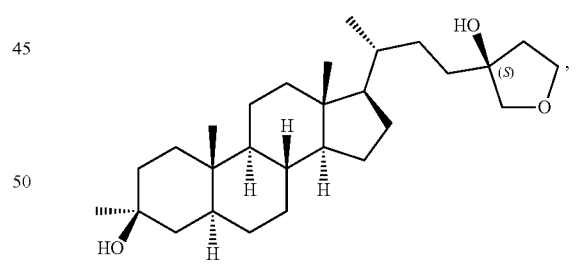
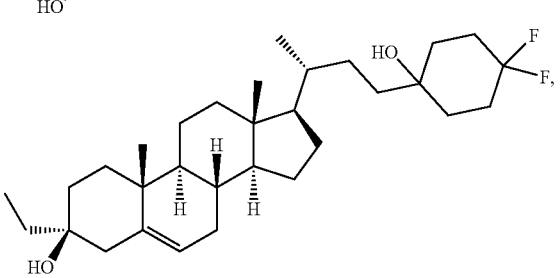
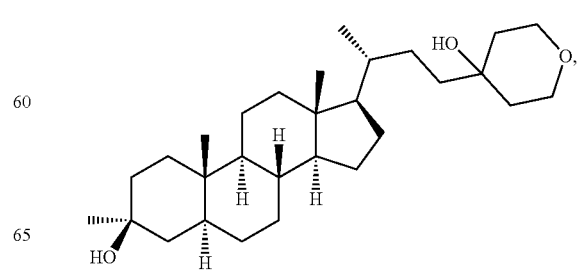

-continued
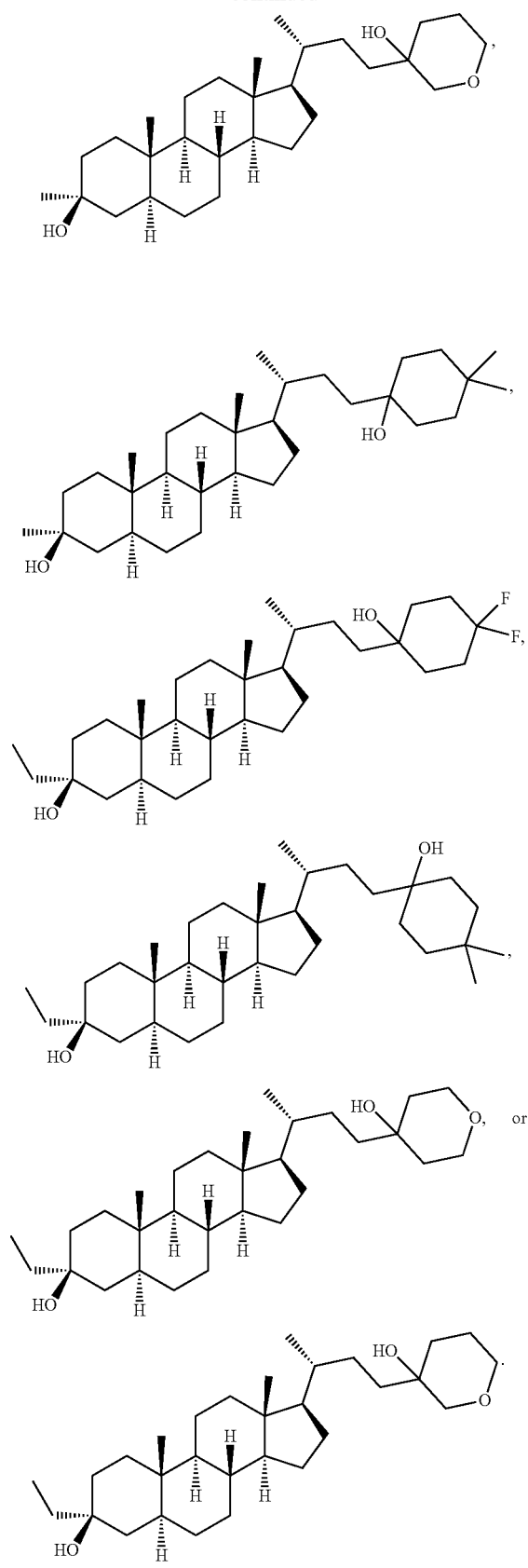
In some embodiments, the compound is a pharmaceutically acceptable salt of:
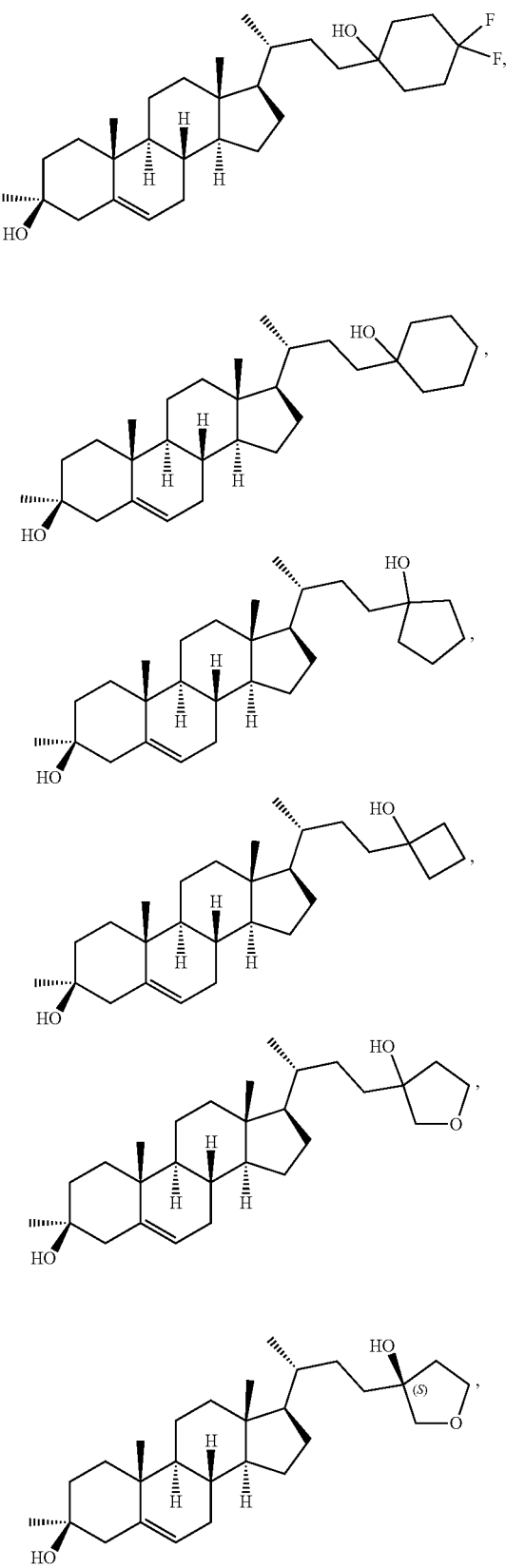

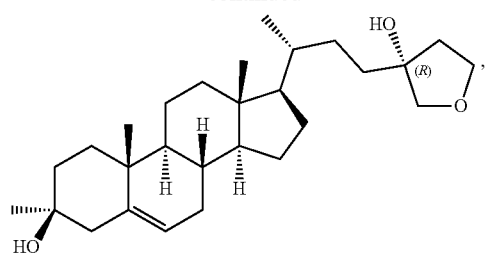
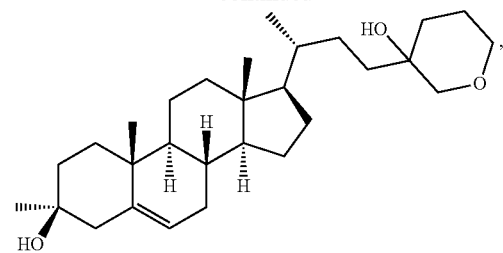
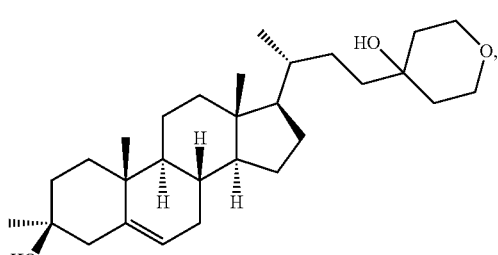
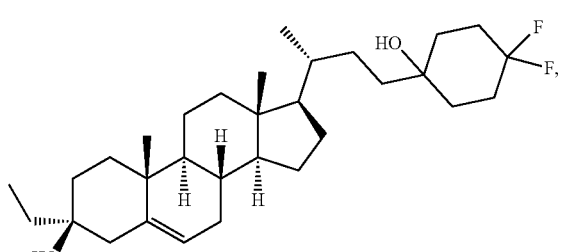
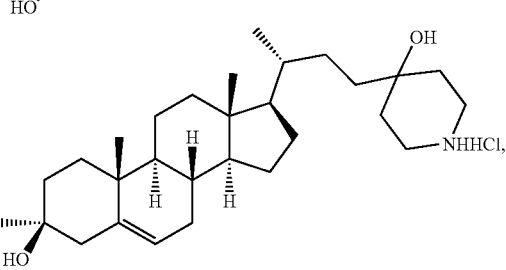
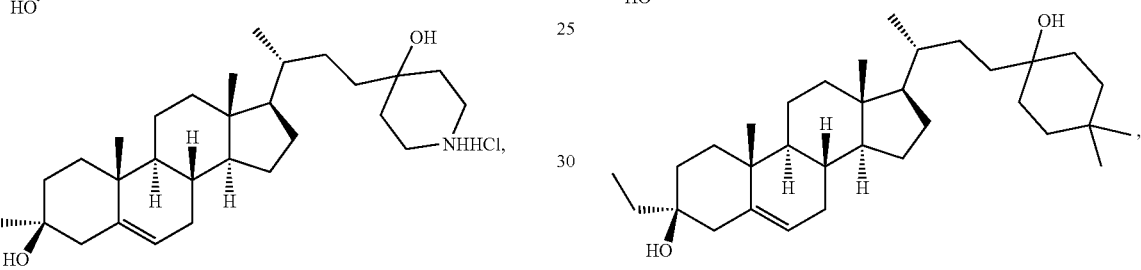
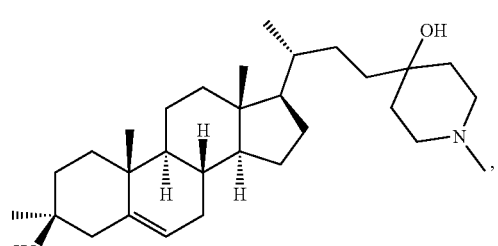
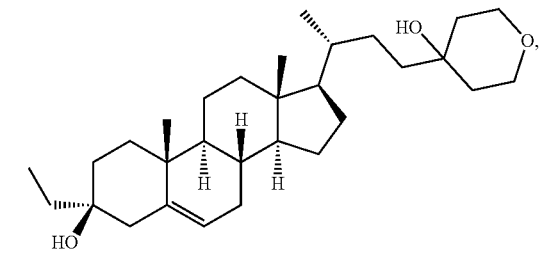
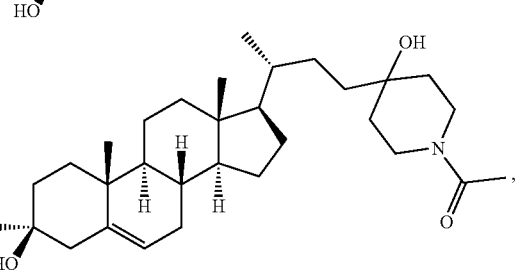
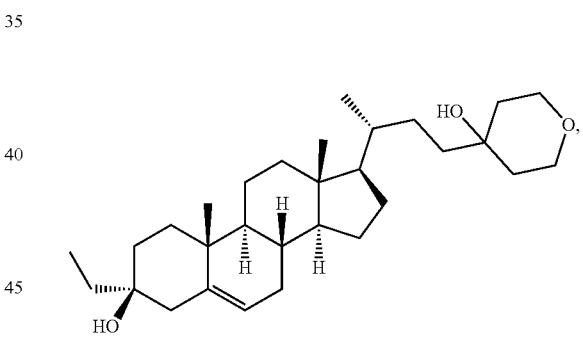
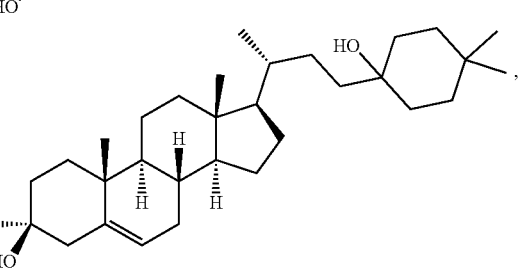
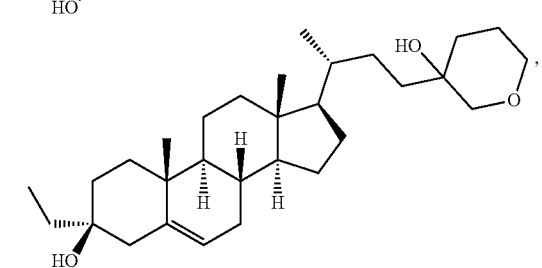
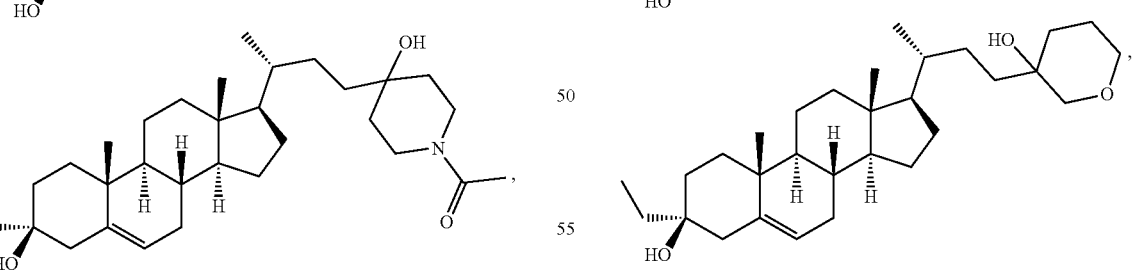

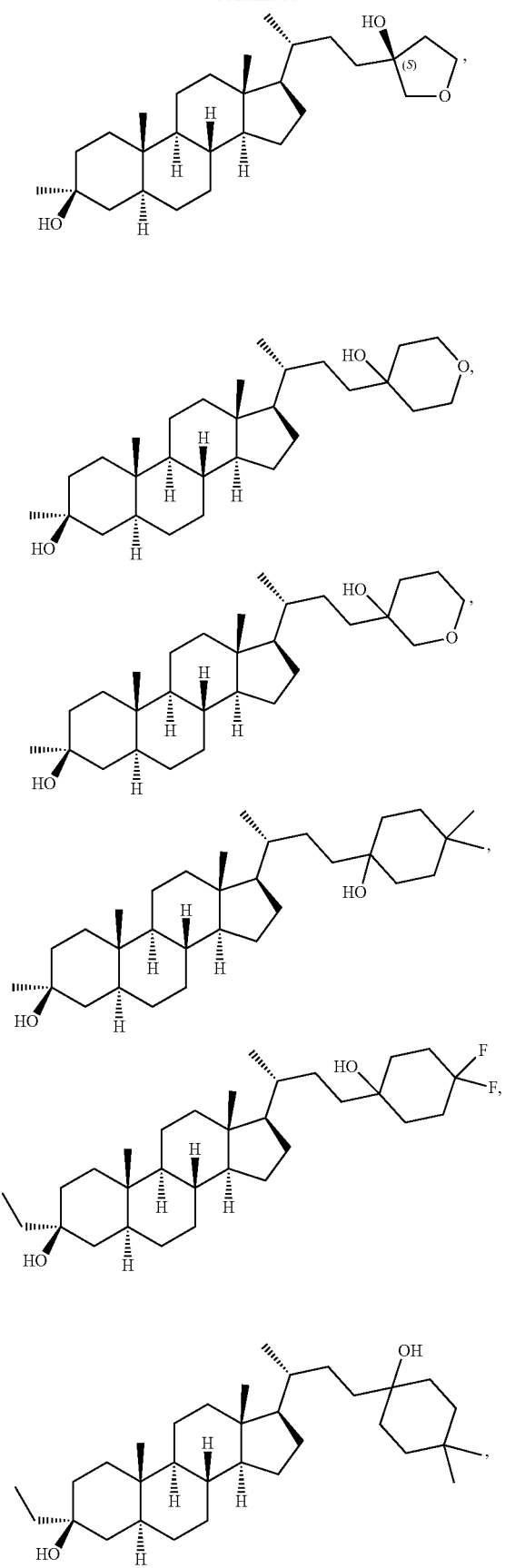

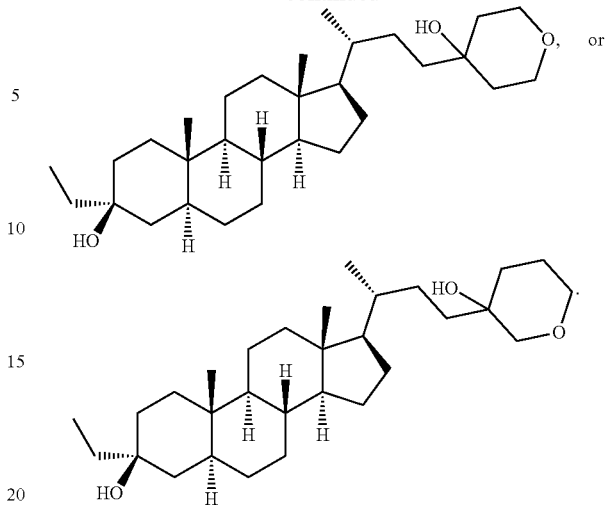

Pharmaceutical Compositions

In another aspect, the invention provides a pharmaceutical composition comprising a pharmaceutically acceptable carrier and a effective amount of a compound as described herein (e.g., Formula (I-A) (I-B), (II-A), (II-B), (II-C), (II-D), (II-E), (II-F), (II-G), (II-H), (II-I), or (II-J)).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound as described herein (e.g., Formula (I-A) (I-B), (II-A), (I-B), (II-C), (II-D), (II-E), (II-F), (II-G), (II-H), (II-I), or (II-J)), or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (I-A), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (I-A), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula (I-A), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula (I-A), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (I-A), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (I-A) (I-B), (II-A), (II-B), (II-C), (II-D), (II-E), (II-F), (II-G), (II-H), (II-I), or (II-J), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (I-A) (I-B), (II-A), (II-B), (II-C), (II-D), (II-E), (II-F), (II-G), (II-H), (II-I), or (II-J), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound as described herein (e.g., Formula (I-A) (I-B), (II-A), (II-B), (II-C), (II-D), (II-E), (II-F), (II-G), (II-H), (II-I), or (II-J)), or pharmaceutically acceptable salt thereof, may act as a negative allosteric modulator (NAM) of NMDA, and inhibit NMDA receptor function. In certain embodiments, the present invention, e.g., a compound of Formula (I-A) (I-B), (II-A), (II-B), (II-C), (II-D), (II-E), (II-F), (II-G), (II-H), (II-I), or (II-J), or pharmaceutically acceptable salt thereof, may act as positive allosteric modulators (PAM) of NMDA, and potentiate NMDA receptor function. In certain embodiments, the compound of Formula (I-A) (I-B), (II-A), (II-B), (II-C), (II-D), (II-E), (II-F), (II-G), (II-H), (II-I), or (II-J), or pharmaceutically acceptable salt thereof, modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a metabolic disorder. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketonuria.

Exemplary conditions related to NMDA-modulation includes, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (I-A) (I-B), (II-A), (II-B), (II-C), (II-D), (II-E), (II-F), (II-G), (II-H), (II-I), or (II-J), or pharmaceutically acceptable salt thereof, can be used to induce sedation or anesthesia. In certain embodiments, the compound of Formula (I-A) (I-B), (II-A), (II-B), (II-C), (II-D), (II-E), (II-F), (II-G), (II-H), (II-I), or (II-J), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, and tinnitus.

In another aspect, provided is a method of treating or preventing brain excitability in a subject susceptible to or afflicted with a condition associated with brain excitability, comprising administering to the subject an effective amount of a compound of the present invention, e.g., a compound of Formula (I-A) (I-B), (II-A), (II-B), (II-C), (II-D), (II-E), (II-F), (II-G), (II-H), (II-I), or (II-J), or a pharmaceutically acceptable salt thereof.

In yet another aspect, the present invention provides a combination of a compound of the present invention, e.g., a compound of Formula (I-A) (I-B), (II-A), (II-B), (II-C), (II-D), (II-E), (II-F), (II-G), (II-H), (II-I), or (II-J), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Diseases and Disorders Described herein are methods of treating a sterol synthesis disorder. Exemplary disorders are described herein. The methods include administering to a subject, e.g., a subject suffering from a sterol synthesis disorder such as SLOS, a NMDA receptor modulating compound. Exemplary compounds are described herein.

Sterol Synthesis Disorders

In one aspect, described herein are methods for treating a sterol synthesis disorder. Cholesterol has an essential rule in growth and development. It is a membrane lipid and a precursor to many molecules that play important roles in cellular growth and diffiuerentiation, protein glycosylation, and signaling pathways. Biosynthesis of cholesterol involves a number of enzymes and intermediates. Disorders resulting from a deficiency in any of the enzymes involved in cholesterol biosynthesis lead to the accumulation of intermediates and imbalance in biomolecules, resulting in disorders including congenital skeletal malformations, dysmorphic facial features, psychomotor retardation, and failure to thrive. In an embodiment, a sterol synthesis disorder or symptom of a sterol synthesis disorder can be treated by administering to a subject suffering from a sterol synthesis disorder a compound described herein, such as a NMDA receptor modulating compound as described herein. Additional disorders are described below.

Smith-Lemli-Opitz Syndrome

In one aspect, described herein are methods for treating Smith-Lemli-Opitz Syndrome (or SLOS, or 7-dehydrocholesterol reductase deficiency). SLOS is an inborn error of cholesterol synthesis. In addition to microcephaly, moderate to severe intellectual disability, sensory hypersensitivity, stereotyped behaviors, dysmorphic facial features, and syndactyly of the second/third toes, a feature of the disease is reduced cerebrosterol (24(S)-hydroxycholesterol) levels. SLOS is an autosomal recessive genetic condition resulting from deficiency in the final enzyme of the cholesterol synthesis pathway, and causes low or low-normal plasma cholesterol levels and increased 7- and 8-dehydrocholesterol (DHC; 7DHC and 8DHC) levels. Common therapies currently used include dietary cholesterol supplementation, treatment with 3-hydroxy-3-methylglutaryl coenzyme A reductase inhibitors (HMG CoA reductase inhibitors, also known as statins), and treatment with agents that enhance cholesterol production and/or accretion; and to decrease the accumulation of 7DHC and 8DHC, the potentially toxic precursors of cholesterol.

Desmosterolosis

Desmosterolosis is a deficiency in desmosterol reductase and has a similar phenotype to SLOS. In one aspect, described herein are methods for treating desmosterolosis with compounds described herein.

Sitosterolemia

Sitosterolemia is a rare autosomal recessive disorder caused by mutations in two ATP-binding cassette (ABC) transporter genes (ABCG5 and ABCG8). Sitosterolemia enhances the absorption of plant sterols and cholesterol from the intestines. Patients typically present with tendon and tuberous xanthomas and premature coronary artery disease. In one aspect, described herein are methods for treating sitosterolemia with compounds described herein.

Cerebrotendinous Xanthomatosis (CTX)

In one aspect, described herein are methods for treating cerebrotendinous xanthomatosis (also referred to as cerebral cholesterosis, or Van Bogaert-Scherer-Epstein syndrome) with compounds described herein. CTX can be caused by a mutation in the CYP27A1 gene, which produces the sterol 27-hydroxylase enzyme. Sterol 27-hydroxylase metabolizes cholesterol into bile acids (e.g., chenodeoxycholic acid) that are important in the absorption of fats in the intestine. Enzyme dysfunction can lead to cholesterol accumulation in tissues. CTX is characterized by childhood diarrhea, cataracts, tendon xanthomas, reduced mental capability and abnormal movements in adults.

Mevalonate Kinase Deficiency Syndromes (MKD)

Mevalonate Kinase Deficiency (also referred to as mevalonic aciduria (a more severe form of MKD), or Hyper IgD Syndrome (HIDS, or hyperimmunoglobulinemia D) with period fever syndrome (a more benign form of MKD)) causes an accumulation of mevalonic acid in the urine as a result of insufficient activity of mevalonate kinase. MKD can result in developmental delay, hypotonia, anemia, hepatosplenomegaly, dysmorphic features, mental retardation, and overall failure to thrive. Mevalonic aciduria is characterized by delayed physical and mental development, failure to thrive, recurrent episodes of fever with vomiting and diarrhea, enlarged liver, spleen and lymph nodes, microcephaly (small head size), cataract, low muscle tone, short statute, distinctfacial features, ataxia, and anemia. HIDS is characterized by recurrent episodes of fever associated with swollen lymph nodes, joint pain, gastrointestinal issues and skin rash. In one aspect, described herein are methods for treating MKD with the compounds described herein.

SC4MOL Gene Mutation (SMO Deficiency)

SC4MOL gene deficiency is a genetic disorder in the cholesterol biosynthesis pathway (e.g., mutations in the SC4MOL gene encoding a novel sterol oxidase). SC4MOL deficiency is characterized by the accumulation of dimethyl and monomethyl sterols that can be detected in blood, skin flakes or primary skin fibroblasts. In one aspect, described herein are methods for treating SMO deficiency with compounds described herein.

Niemann-Pick Disease

Niemann-Pick disease is a lysosomal storage disease resulting from a genetic mutation that affects metabolism. Niemann-Pick disease leads to abnormal accumulation of cholesterol and other fatty substances (lipids) due to an inability of the body to transport the substances. The accumulation damages the affected areas.

Autism

In one aspect, described herein are methods for treating autism spectrum disorder or autism. Autism spectrum disorder (ASD) and autism refer to a group of complex disorders of brain development. Autism is typically characterized by difficulties in social interaction, for example in verbal and nonverbal communication. Repetitive behaviors are also often seen in individuals having autism. Autism can be associated with intellectual disability, difficulties in motor coordination and attention and physical health issues, e.g., sleep and gastrointestinal disturbances. Individuals having autism can also excel in visual skills, music, math and art. Autism can refer to autistic disorder, childhood disintegrative disorder, pervasive developmental disorder-not otherwise specified (PDD-NOS), and Asperger syndrome. Autism also refers to monogenetic causes of autism such as synaptophathy's, e.g., Rett syndrome, Fragile X syndrome, Angelman syndrome.

Disorders Associated with Phenylketonuria

In one aspect, described herein are methods for treating disorders associated with phenylketonuria (e.g., cognitive disorders) with compounds described herein. Phenylketonuria can lead to hypochesterolemia and lowered vitamin D status. Total and low-density cholesterols and 25-hydroxy vitamin D have been found to be decreased in subjects suffering from phenylketonuria as compared with subjects not suffering from phenylketonuria (Clin. Chim. Acta 2013, 416: 54-59). 24S-hydroxycholesterol and 27S-hydroxycholesterol and 7α-hydroxycholesterol (e.g., representing peripheral and hepatic cholesterol elimination, respectively) have been shown to be significantly decreased in subjects suffering from phenylketonuria, while 7β-hydroxycholesterol (e.g., reflecting oxidative stress) was increased significantly in subjects suffering from phenylketonuria. Changes in the levels of 24S—OHC and 7p-hydroxycholesterol correlate with phenylalanine level, and 27S-hydroxycholesterol levels may correlate with the 25-hydroxy vitamin D level in subjects suffering from phenylketonuria.

Alternative Embodiments

In an alternative embodiment, a compound described herein (e.g., a compound of Formula (I-A) (I-B), (II-A), (II-B), (II-C), (II-D), (II-E), (II-F), (II-G), (II-H), (II-I), or (II-J)) may also comprise one or more isotopic substitutions. In some embodiments, hydrogen may be $^2$H (D or deuterium), or $^3$H (T or tritium). In some embodiments, carbon may be $^{13}$C or $^{14}$C. In some embodiments, oxygen may be $^{18}$O). In some embodiments, nitrogen may be $^{15}$N. In a further embodiment, a compound may comprise one or more isotopic substitutions where the site of isotopic substitution is enriched with a particular isotope. For example, a compound described herein can comprise hydrogen enriched as $^2$H or $^3$H, carbon enriched as $^{13}$C or $^{14}$C, oxygen enriched as $^{18}$O, or nitrogen enriched as $^{15}$N.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative neuroactive steroids that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$·H$_2$O). Flow rate: 25 mL/min.

Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: XBridge C18, 4.6*50 mm, 3.5 μm at 45 C.

NMDA Potentiation

NMDA potentiation was assessed using the whole cell patch clamp of mammalian cells which expressed NMDA receptors.

Whole-Cell Patch Clamp of Mammalian Cells (Ionworks Barracuda (IWB)

The whole-cell patch-clamp technique was used to investigate the effects of compounds on GluN1/GluN2A glutamate receptors expressed in mammalian cells. The results are shown in Table 1.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 µg/ml penicillin G sodium, 100 µg/ml streptomycin sulphate, 100 µg/ml Zeocin, 5 µg/ml blasticidin and 500 g/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeScienses). The measurements were performed using Ion Works Barracuda platform following this procedure:

Electrophysiological Procedures:
a) Intracellular solution (mM): 50 mM CsCl, 90 mM CsF, 2 mM $MgCl_2$, 5 mM EGTA, 10 mM HEPES. Adjust to pH 7.2 with CsOH.
b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
c) Holding potential: −70 mV, potential during agonist/PAM application: −40 mV.

Recording Procedure:
a) Extracellular buffer will be loaded into the PPC plate wells (11 µL per well). Cell suspension will be pipetted into the wells (9 µL per well) of the PPC planar electrode.
b) Whole-cell recording configuration will be established via patch perforation with membrane currents recorded by on-board patch clamp amplifiers.
c) Two recordings (scans) will be performed. First, during pre-application of test article alone (duration of pre-application—5 min) and second, during test articles and agonist ($EC_{20}$ L-glutamate and 30 µM glycine) co-application to detect positive modulatory effects of the test article.

Test Article Administration: The first pre-application will consist of the addition of 20 µL of 2× concentrated test article solution and, second, of 20 µL of 1× concentrated test article and agonist at 10 µL/s (2 second total application time).

Synthetic Methods

Example 1. Synthesis of Intermediate A-6

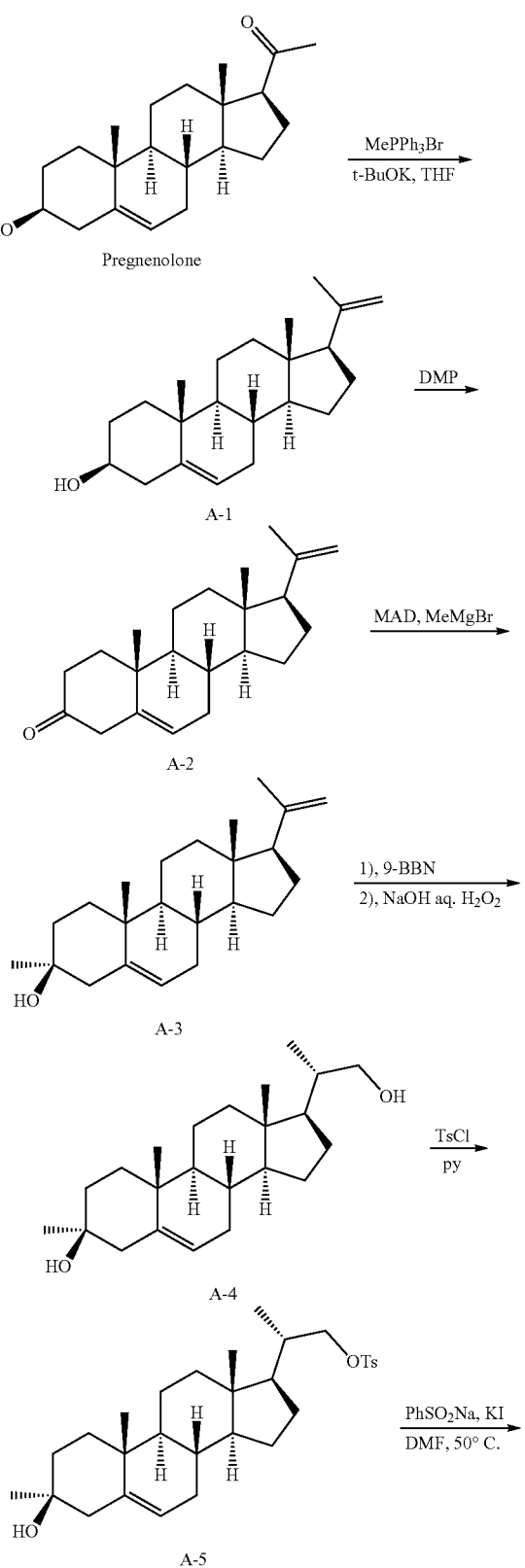

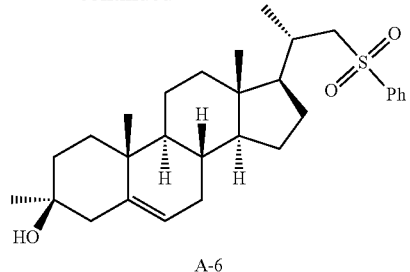

A-6

Step 1. Synthesis of Intermediate A-1. To a suspension of PPh₃MeBr (2.13 kg, 5.97 mol) in THF (3000 mL) was added t-BuOK (688 g, 6.14 mol) at 20° C. The color of the suspension changed to yellow. After stirring at 50° C. for 1 h, Pregnenolone (630 g, 2.05 mol) was added at 50° C. and the reaction mixture was stirred at 50° C. for 2 h. After cooling to 20° C., the mixture was treated with NH₄Cl (10% aq., 5 L) and heptane (3.5 L) and stirred for 15 minutes. The organic layer was separated and concentrated in vacuo to give the crude material as a thick oil, which was poured into MTBE (10 L) with vigorous stirring and allowed to stir at room temperature for 16 hours. The resulting off-white solid was collected by filtration and washed with MTBE (3 L). The combined filtrate was mixed with MeOH (10 L) and concentrated to 6 L in vacuo. The resulting off-white solid was collected by filtration, washed with MeOH (3 L), and air-dried to give 700 g of wet off-white solid. The combined MeOH filtrate was concentrated in vacuo to give a thick oil. The oil was poured into MTBE (3 L) with vigorous stirring and the mixture was allowed to stir for 3 hours. The resulting white solid was collected by filtration and washed with MTBE (1 L). The combined filtrate was mixed with MeOH (3 L) and concentrated to 1.5 L in vacuo. The resulting white solid was collected by filtration, washed with MeOH (500 mL) and air-dried to give 150 g of a wet off-white solid. The previous 700 g and 150 g batch were combined and vacuum-dried to give Intermediate A-1 (552 g, 88%) as an off-white solid.

¹H NMR (400 MHz, CDCl₃) δ 5.40-5.30 (m, 1H), 4.85 (s, 1H), 4.71 (s, 1H), 3.60-3.50 (m, 1H), 2.36-2.18 (m, 2H), 2.08-1.96 (m, 2H), 1.92-1.78 (m, 3H), 1.76 (s, 3H), 1.73-1.48 (m, 9H), 1.38-1.03 (m, 4H), 1.01 (s, 3H), 1.00-0.91 (m, 1H), 0.58 (s, 3H).

Step 2. Synthesis of Intermediate A-2. To a solution of Intermediate A-1 (184 g, 585 mmol) in DCM (2000 mL) was added DMP (496 g, 1.17 mol) at 25° C. in portions, followed by water (42 mL). The mixture was stirred at 25° C. for 30 min. Water (1500 mL) and NaHCO₃ (750 g) were added in portions (gas evolution was observed). The mixture was filtered through a pad of Celite and the solid was washed with DCM (500 mL). The organic layer in the filtrate was separated, washed with Na₂S₂O₃ (1000 mL, saturated), dried over Na₂SO₄, filtered, concentrated in vacuo below 30° C. to give Intermediate A-2 (250 g, crude) as a light yellow gum. The crude was used in the next step directly without further purification or analysis.

Step 3. Synthesis of Intermediate A-3. To a solution of BHT (769 g, 3.49 mol) in toluene (1500 mL) was added AlMe₃ (870 mL, 2M in toluene, 1.74 mol) at 0° C. After stirring at 0° C. for 1 h, the reaction mixture was cooled to −78° C. and a solution of Intermediate A-2 (250 g crude, theoretical mass: 182 g, 582 mmol) in toluene (1000 mL) was added. After stirring at −78° C. for 1 h, MeMgBr (580 mL, 3 M in ether, 1.74 mmol) was added and the mixture was stirred at −78° C. for another 1 h. The mixture was quenched by pouring into citric acid (4000 mL, 20% aq.) in portions (gas evolution was observed). Another two batches were conducted and combined. The mixture was extracted with EtOAc (10 L). The organic layer was separated, washed with brine (5 L, 10%), NaHCO₃ (5 L, saturated aq.), brine (5 L, saturated), dried over Na₂SO₄ and concentrated in vacuo. The resulting residue was purified by silica gel chromatography (PE to EtOAc) to give Intermediate A-3 (440 g, impure, containing Intermediate A-1) as a light yellow solid. To a solution of impure Intermediate A-3 (440 g) in DCM (6 L) was added DMAP (24.4 g) and Ac₂O (51 g). The mixture was stirred at 20° C. for 1 h. NaHCO₃ (1 L, saturated aq.) was added and the mixture was stirred for 10 min. The organic layer was separated, concentrated in vacuo and the residue was triturated with PE (2 L). The solid was washed with PE (3×500 mL) and dried in vacuo to give A-3 (262 g) as an off-white solid. The combined filtrate was concentrated, purified by silica gel chromatography (PE/EtOAc=50/1 to 8/1) and triturated with PE (1 L) to give A-3 (30 g). Total yield for the two steps was 510%.

¹H NMR (400 MHz, CDCl₃) δ 5.35-5.28 (m, 1H), 4.85 (s, 1H), 4.71 (s, 1H), 2.48-2.37 (m, 1H), 2.08-1.94 (m, 3H), 1.92-1.85 (m, 1H), 1.82-1.33 (m, 14H), 1.29-1.08 (m, 7H), 1.02 (s, 3H), 1.00-0.93 (m, 1H), 0.59 (s, 3H).

Step 4. Synthesis of Intermediate A-4. Intermediate A-3 (100 g, 304 mmol) was dissolved in 9-BBN (1.21 L, 0.5 M in THF, 608 mmol) at 0° C. under N₂. The solution was heated and stirred at 65° C. for 1 hour and re-cooled to 10° C. to generate a off-white precipitate. Ethanol (279 g, 6080 mmol) and aqueous NaOH (304 mL, 5 M, 1520 mmol) were added dropwise below 10° C. to give a clear solution. Hydrogen peroxide (343 g, 30% in water, 3040 mmol) was added dropwise below 10° C. and the reaction mixture was heated and stirred at 75° C. for 1 hour. The mixture was cooled to 20° C., and the resulting off-white precipitate was collected by filtration. The filter cake was washed with water (3×500 mL) and dried in vacuo to give an off-white solid, which was triturated with ethanol (1.5 L) at reflux to give Intermediate A-4 (92 g, 88%) as an off-white solid.

¹H NMR (400 MHz, CDCl₃) δ 5.31-5.29 (m, 1H), 3.65-3.63 (m, 1H), 3.38-3.37 (m, 1H), 2.42 (d, J=12.4, 1H), 2.05-1.92 (m, 3H), 1.88-1.63 (m, 4H), 1.63-1.40 (m, 8H), 1.40-0.90 (m, 16H), 0.70 (s, 3H).

Step 5. Synthesis of Intermediate A-3. To a solution of Intermediate A-4 (124.5 g, 357 mmol) in chloroform (1 L) and pyridine (700 mL) was added TsCl (204 g, 1071 mmol) at 15° C. and the mixture was stirred at 15° C. for 2 hrs. The mixture was concentrated in vacuo to remove most of the chloroform. The pyridine mixture was poured into water (6 L) and the resulting off-white solid was collected by filtration, and the filter cake was washed with water (6×1 L). The off-white solid was dissolved in DCM (3.5 L), dried over Na₂SO₄, filtered and concentrated in vacuo to give Intermediate A-5 (163 g, 92%) as an off-white solid.

¹H NMR (400 MHz, CDCl₃) δ 7.78 (d, J=8.0 Hz, 2H), 7.34 (d, J=8.4 Hz, 2H), 5.29-5.28 (m, 1H), 3.96 (dd, J=3.2, 9.6 Hz, 1H), 3.79 (dd, J=6.4, 9.2 Hz, 1H), 2.45 (s, 3H), 2.41 (d, J=13.6 Hz, 1H), 1.99-1.91 (m, 3H), 1.77-1.39 (m, 11H), 1.26-0.86 (m, 16H), 0.64 (s, 3H).

Step 6 Synthesis of Intermediate A-6 To a solution of Intermediate A-5 (163 g, 325 mmol) in DMF (1.7 L) was added KI (258 g, 1560 mmol) at 15° C. The mixture was heated and stirred at 60° C. for 2 hours. Sodium benzene-sulfinate (195 g, 975 mmol) was added and stirring was continued at 60° C. for 2 hours. The reaction mixture was cooled to 25° C. and combined with another batch of 83 g of Intermediate A-5. The combined mixture was poured into water (20 L) to give a yellow solid which was collected by filtration and washed with water (3×2 L). The resulting filter cake was dissolved in DCM (5 L), washed with water (2×1 L), brine (2×1 L), dried over Na$_2$SO$_4$, filtered and concentrated in vacuo to give a yellow solid residue, which was re-crystallized from toluene (2.5 L) to give Intermediate A-6 (150 g, 65%) as a light yellow solid. The re-crystallization filtrate was concentrated in vacuo to give crude Intermediate A-6 (30 g) as a yellow solid.

$^1$H NMR (400 MHz, CDCl$_3$) δ 7.91 (d, J=7.2 Hz, 2H), 7.69-7.61 (m, 1H), 7.60-7.50 (m, 2H), 5.28-5.27 (m, 1H), 3.14 (d, J=14.0 Hz, 1H), 2.85 (dd, J=9.6, 14.0 Hz, 1H), 2.41 (d, J=12.8 Hz, 1H), 2.17-2.03 (m, 1H), 2.02-1.87 (m, 3H), 1.81-1.65 (m, 3H), 1.60-1.32 (m, 8H), 1.25-0.85 (m, 15H), 0.65 (s, 3H). LCMS Rt=2.057 min in 3.0 min chromatography, 30-90 AB, MS ESI calcd. for C$_{29}$H$_{41}$O$_2$S [M+H−H$_2$O]$^+$ 453, found 453.

Example 2. Synthesis of Intermediate B-4

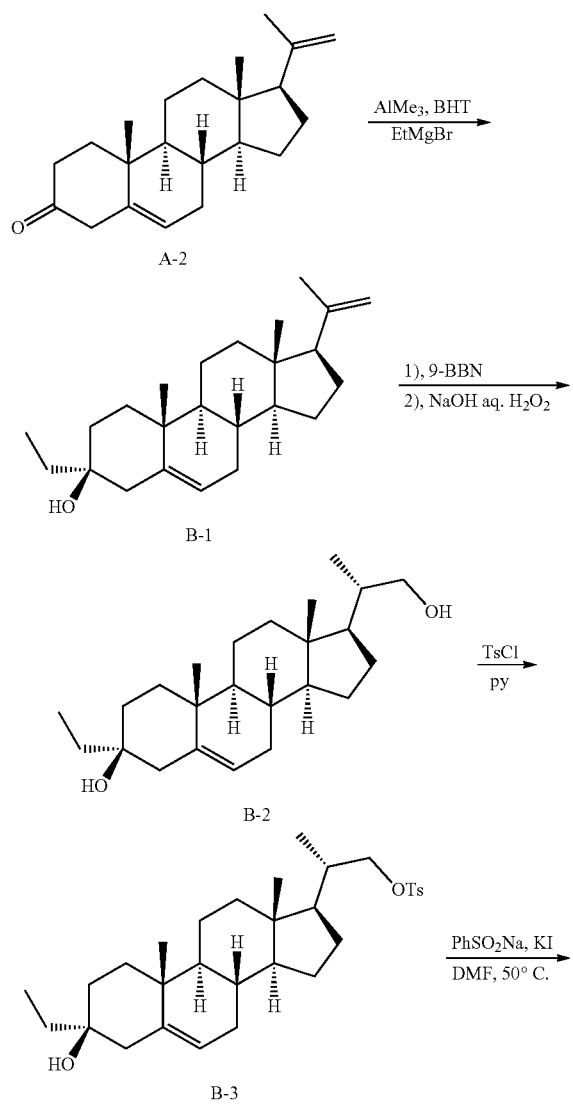

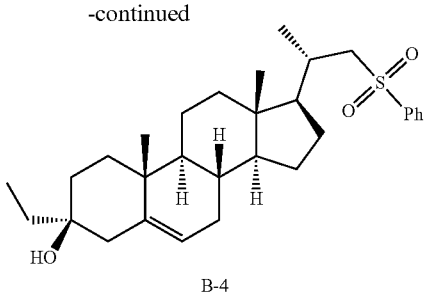

Step 1. Synthesis of Intermediate B-1. To a solution of BHT (191 g, 866 mmol) in toluene (500 mL) was added AlMe$_3$ (2 M in toluene, 216 mL, 433 mmol) at 10° C. and the solution was stirred for 1 h. To the mixture was added a solution of Intermediate A-2 (Theoretical Mass: 44.6 g) in DCM (100 mL) at −78° C. The mixture was stirred at −78° C. for 1 h. EtMgBr (141 mL, 426 mmol) was added at −78° C. and the mixture was stirred at −78° C. for 20 mins. Saturated citric acid (1 L) was added. The organic phase was separated, washed with brine (600 mL), dried over Na$_2$SO$_4$ and concentrated in vacuo to give a residue, which was purified by column chromatography on silica gel (PE:EtOAc=50:1 to 30:1) to give Intermediate B-1 (27 g, 55%) as a yellow solid.

$^1$H NMR (400 MHz, CDCl$_3$) δ 5.35-5.25 (m, 1H), 4.85 (s, 1H), 4.71 (s, 1H), 2.40-2.30 (m, 1H), 2.10-1.60 (m, 14H), 1.50-0.75 (m, 17H), 0.58 (s, 3H).

Step 2. Synthesis of Intermediate B-2. To 9-BBN (200 mL, 0.5 M in THF, 100 mL) was added Intermediate B-1 (13 g, 37.9 mmol) at 0° C. under N$_2$. The mixture was heated and stirred at 65° C. for 2 hrs then cooled to 10° C. EtOH (46.5 g) was added, followed by aqueous NaOH (51 mL, 5 M) and H$_2$O$_2$ (57 g, 30% in water) and the resulting mixture was stirred at 75° C. for 1 h. The mixture was concentrated in vacuo to give a solution (100 mL), which was extracted with EtOAc (2×150 mL), washed with NH$_4$Cl (2×300 mL) and brine (2×300 mL), dried over Na$_2$SO$_4$, filtered and concentrated in vacuo to give a residue, which was purified by column chromatography on silica gel (PE:EtOAc=50:1 to 3:1) to give Intermediate B-2 (9.86 g, 72%) as an off-white solid.

$^1$H NMR (400 MHz, CDCl$_3$) δ 5.31-5.29 (m, 1H), 3.70-3.60 (m, 1H), 3.40-3.30 (m, 1H), 2.40-2.30 (m, 1H), 2.10-1.90 (m, 3H), 1.75-1.65 (m, 1H), 1.65-1.55 (m, 2H), 1.50-1.26 (m, 6H), 1.25-0.95 (m, 15H), 0.90-0.75 (m, 6H), 0.70 (s, 3H).

Step 3. Synthesis of intermediate B-3. To a solution of Intermediate B-2 (9.86 g, 27.3 mmol) in CHCl$_3$ (100 mL) and pyridine (20 mL) was added TsCl (15.6 g, 81.9 mmol) at 15° C. The mixture was stirred at 15° C. for 1 h. The reaction mixture was concentrated in vacuo to give 60 mL of the mixture, which was poured into 600 mL of water to give an off-white precipitate. The mixture was filtered, the filter cake was washed with water, dissolved in DCM (150 mL), dried over Na$_2$SO$_4$, filtered, concentrated under vacuum to give Intermediate B-3 as an off-white solid (9.9 g, 70%).

$^1$H NMR (400 MHz, CDCl$_3$) δ 7.78 (d, J=8.4 Hz, 2H), 7.34 (d, J=8.0 Hz, 2H), 5.30-5.20 (m, 1H), 4.00-3.90 (m, 1H), 3.80-3.70 (m, 1H), 2.45 (s, 3H), 2.40-2.30 (m, 1H), 2.10-1.90 (m, 3H), 1.75-1.60 (m, 6H), 1.55-1.30 (m, 5H), 1.25-0.95 (m, 13H), 0.90-0.80 (m, 5H), 0.65-0.50 (m, 3H).

Step 4. Synthesis of Intermediate B-4. To a solution of Intermediate B-3 (9.9 g, 19.2 mmol) in DMF (150 mL) was added KI (15.2 g, 92.1 mmol) at 15° C. The mixture was heated and stirred at 60° C. for 2 hrs. Sodium benzenesulfinate (9.43 g, 57.5 mmol) was added and the mixture was stirred at 60° C. for 2 hrs. The mixture was poured into water (200 mL) and the resulting yellow precipitate was collected by filtration. The filter cake was washed with water (2×100 L), dissolved in DCM (500 mL), washed with water (2×500 mL) and brine (2×1 L), dried over $Na_2SO_4$, filtered and concentrated in vacuo to give a yellow solid residue, which was purified by silica gel chromatography (0-35% EtOAc in PE) to give Intermediate B-4 (8 g, 89%).

$^1$H NMR (400 MHz, $CDCl_3$) δ 7.95-7.88 (m, 2H), 7.68-7.62 (m, 1H), 7.61-7.53 (m, 2H), 5.30-5.22 (m, 1H), 3.20-3.08 (m, 1H), 2.91-2.79 (m, 1H), 2.40-2.30 (m, 1H), 2.09-1.87 (m, 4H), 1.74-1.60 (m, 4H), 1.50-1.36 (m, 7H), 1.24-0.98 (m, 13H), 0.90-0.80 (m, 4H), 0.65 (s, 3H).

Example 3. Synthesis of Intermediate C-8

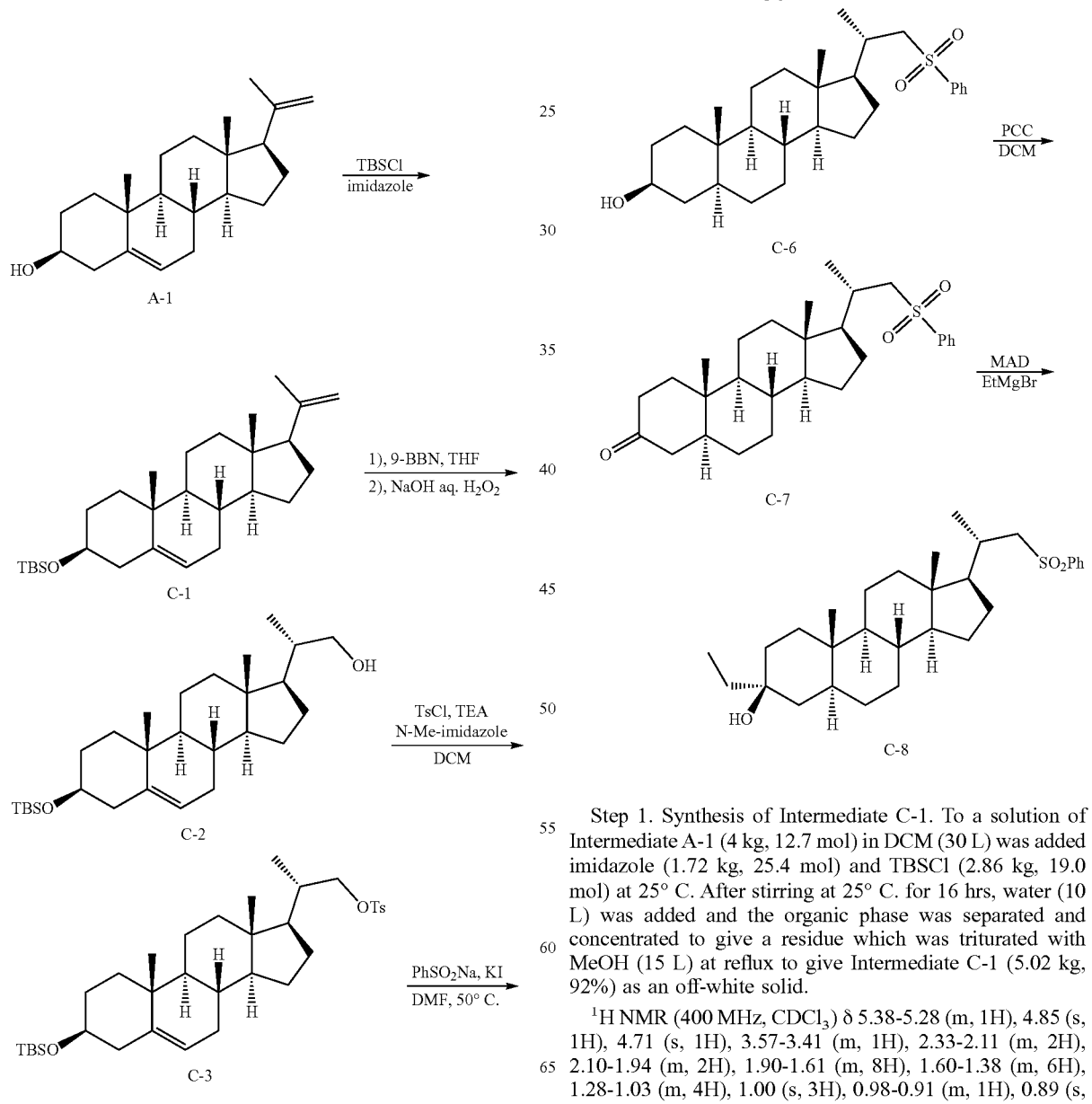

Step 1. Synthesis of Intermediate C-1. To a solution of Intermediate A-1 (4 kg, 12.7 mol) in DCM (30 L) was added imidazole (1.72 kg, 25.4 mol) and TBSCl (2.86 kg, 19.0 mol) at 25° C. After stirring at 25° C. for 16 hrs, water (10 L) was added and the organic phase was separated and concentrated to give a residue which was triturated with MeOH (15 L) at reflux to give Intermediate C-1 (5.02 kg, 92%) as an off-white solid.

$^1$H NMR (400 MHz, $CDCl_3$) δ 5.38-5.28 (m, 1H), 4.85 (s, 1H), 4.71 (s, 1H), 3.57-3.41 (m, 1H), 2.33-2.11 (m, 2H), 2.10-1.94 (m, 2H), 1.90-1.61 (m, 8H), 1.60-1.38 (m, 6H), 1.28-1.03 (m, 4H), 1.00 (s, 3H), 0.98-0.91 (m, 1H), 0.89 (s, 9H), 0.58 (s, 3H), 0.06 (s, 6H).

Step 2. Synthesis of Intermediate C-2. To a solution of Intermediate C-1 (1.69 kg, 3.94 mol) in THF (8 L) was added 9-BBN dimer (671 g, 2.75 mol) and the resulting mixture was stirred at 25° C. under $N_2$ for 1 h (formation of an off-white precipitate was observed). Ethanol (2.26 L, 39.4 mol) and NaOH (3.94 L, 5 M, 19.7 mol) were added and the resulting clear solution was treated dropwise with $H_2O_2$ (3.94 L, 10 M, 39.4 mol) at 25° C. (the inner temperature raised to reflux). After addition was complete, the mixture was cooled to 25° C. and stirred for 16 hrs, followed by addition of $Na_2SO_3$ (2.5 L, 20% aq.) and water (5 L) at 25° C. After stirring for 1 hr, the mixture was allowed to settle to a clear lower layer and an upper suspension layer. The upper suspension layer was collected and treated with water (20 L). The mixture was stirred for 15 mins and filtered. The solid was washed with water to pH<9 to give the wet product, which was combined with two other batches of product from a previous synthesis. The wet product was dissolved in DCM (100 L) and the organic layer was separated, dried over $Na_2SO_4$, filtered and concentrated to 20 L. The residue was used in the next step directly.

$^1$H NMR (400 MHz, $CDCl_3$) δ 5.40-5.23 (m, 1H), 3.70-3.60 (m, 1H), 3.55-3.42 (m, 1H), 3.41-3.31 (m, 1H), 2.31-2.20 (m, 1H), 2.20-2.11 (m, 1H), 2.06-1.91 (m, 2H), 1.89-1.67 (m, 3H), 1.65-1.39 (m, 7H), 1.38-1.08 (m, 6H), 1.05 (d, J=6.4 Hz, 3H), 1.00 (s, 3H), 0.99-0.91 (m, 2H), 0.88 (s, 9H), 0.70 (s, 3H), 0.05 (s, 6H).

Step 3. Synthesis of Intermediate C-3. To a solution of Intermediate C-2 (theoretical mass: 5.2 kg, 11.6 mol) in DCM (15 L) was added N-methyl-imidazole (1.37 L, 17.4 mol) and TEA (3.2 L, 23.2 mol) at 25° C. TsCl (2.53 kg, 13.3 mol) was added portionwise to the above solution, maintaining the inner temperature between 25~30° C. The reaction mixture was stirred at 25° C. for 1 h. To the mixture was added water (10 L), citric acid (20%, 1 L) and HCl (1 M) to adjust the pH to ~3. The organic layer was separated, washed with water (2×10 L), $NaHCO_3$ (saturated aq. 5 L) and brine (5 L), dried over $Na_2SO_4$, filtered and concentrated to give Intermediate C-3 (6.63 kg, 95% for 2 steps) as an off-white solid.

$^1$H NMR (400 MHz, $CDCl_3$) δ 7.78 (d, J=8.4 Hz, 2H), 7.34 (d, J=8.0 Hz, 2H), 5.37-5.25 (m, 1H), 3.96 (dd, J=2.8, 9.2 Hz, 1H), 3.79 (dd, J=6.4, 9.2 Hz, 1H), 3.53-3.41 (m, 1H), 2.45 (s, 3H), 2.32-2.20 (m, 1H), 2.20-2.11 (m, 1H), 2.01-1.88 (m, 2H), 1.84-1.61 (m, 4H), 1.56-1.31 (m, 6H), 1.23-1.02 (m, 5H), 1.02-0.95 (m, 7H), 0.93-0.90 (m, 1H), 0.88 (s, 9H), 0.63 (s, 3H), 0.05 (s, 6H).

Step 4. Synthesis of Intermediate C-4. To a suspension of Intermediate C-3 (2.69 kg, 4.47 mol) in DMF (25 L) was added KI (1.48 g, 8.94 mol) at 70° C. and the mixture was stirred at 70° C. for 1 h. $PhSO_2Na$ (2.19 kg, 13.4 mol) was added and stirring was continued at 70° C. for 1 h. The mixture was poured into water (50 L) and filtered. The filter cake was washed with water (2×10 L) to give the wet product, which was combined with two other batches from previous syntheses. Half of the wet product was triturated with MeCN (20 L) at 80° C. and cooled to 30° C. The heating and cooling process was repeated two more times and the residue was collected by filtration and further triturated with MeCN/toluene (20 L, 10:1) at 80° C., filtered, washed with MeCN (3×5 L), dried in vacuo to give Intermediate C-4 (2.21 kg) as a white solid. Another half of the wet product was triturated with MeCN (20 L) at 80° C. and cooled to 50° C. The heating and cooling process was repeated two more times and the precipitate was collected by filtration to give Intermediate C-4 (1.92 kg) as an off-white solid. Totally 4.13 kg of the product was obtained (67% yield).

$^1$H NMR (400 MHz, $CDCl_3$) δ 8.00-7.82 (m, 2H), 7.69-7.61 (m, 1H), 7.60-7.49 (m, 2H), 5.37-5.20 (m, 1H), 3.57-3.39 (m, 1H), 3.14 (d, 0.1=14.0 Hz, 1H), 2.85 (dd, J=9.6, 14.0 Hz, 1H), 2.35-2.05 (m, 3H), 2.02-1.88 (m, 2H), 1.85-1.62 (m, 3H), 1.61-1.32 (m, 7H), 1.29-0.91 (m, 12H), 0.88 (s, 9H), 0.65 (s, 3H), 0.05 (s, 6H).

Step 5. Synthesis of Intermediate C-5. To a suspension of Intermediate C-4 (2.21 kg, 3.87 mol) in THF (10 L) was added TBAF·3$H_2O$ (1.87 kg, 5.92 mol). The mixture was heated and stirred at 65° C. for 1 h to give a clear solution, which was treated with water (25 L) and stirred at 80° C. for 2 h. After cooling, the mixture was filtered and the filter cake was washed with water (3×10 L) and air-dried to give Intermediate C-5 (1.83 kg, crude) as an off-white solid.

$^1$H NMR (400 MHz, $CDCl_3$) δ 7.98-7.88 (m, 2H), 7.69-7.61 (m, 1H), 7.60-7.51 (m, 2H), 5.40-5.28 (m, 1H), 3.58-3.44 (m, 1H), 3.14 (d, J=13.2 Hz, 1H), 2.85 (dd, J=9.6, 14.0 Hz, 1H), 2.36-2.18 (m, 2H), 2.18-2.04 (m, 1H), 2.03-1.90 (m, 2H), 1.89-1.79 (m, 2H), 1.78-1.68 (m, 1H), 1.62-1.48 (m, 6H), 1.38-0.84 (m, 14H), 0.65 (s, 3H).

Step 6. Synthesis of Intermediate C-6. To a solution of Intermediate C-5 (50 g, 109 mmol) in THF (500 mL) was added Pd/C (wet, 10%, 11.7 g, 10.9 mmol) under Ar. After degassing three times with $N_2$, the reaction mixture was purged three times with $H_2$. The reaction mixture was stirred for 72 h at 25° C. under a hydrogen atmosphere (50 Psi). Formation of the desired product and consumption of starting material was confirmed by NMR. The catalyst was removed by filtration and the filtrate was concentrated to give Intermediate C-6 (39 g, crude) as an off-white solid, which was used in next step directly without further purification.

$^1$H NMR (400 MHz, $CDCl_3$) δ 7.85-7.82 (m, 2H), 7.58-7.55 (m, 1H), 7.52-7.47 (m, 2H), 3.54-3.47 (m, 1H), 3.09-3.04 (m, 1H), 2.80-2.74 (m, 1H), 2.03-1.83 (m, 2H), 1.63-1.46 (m, 2H), 1.30-1.21 (m, 8H), 1.20-1.17 (m, 7H), 1.16-1.10 (m, 6H), 1.09-0.92 (m, 2H), 0.72 (s, 3H), 0.60-0.48 (m, 4H).

Step 7. Synthesis of Intermediate C-7. To a solution of Intermediate C-6 (196 g, 427 mmol) in DCM (2 L) was added PCC (137 g, 640 mmol) and the reaction mixture was stirred at 25° C. for 2 h, then filtered and concentrated in vacuo to give a residue which was purified by silica gel chromatography (DCM) to give Intermediate C-7 (145 g, 74%) as an off-white solid.

$^1$H NMR (400 MHz, $CDCl_3$) δ 7.95-7.85 (m, 2H), 7.70-7.60 (m, 1H), 7.60-7.50 (m, 2H), 3.20-3.10 (m, 1H), 2.90-2.80 (m, 1H), 2.45-2.20 (m, 3H), 2.15-1.90 (m, 4H), 1.75-1.60 (m, 2H), 1.55-1.00 (m, 16H), 0.99 (s, 3H), 0.95-0.70 (m, 2H), 0.66 (s, 3H).

Step 8. Synthesis of Intermediate C-8. To a solution of BHT (499 g, 2.27 mmol) in anhydrous toluene (1 L) under $N_2$ at 0° C. trimethylaluminum (2 M in toluene, 525 mL, 1.05 mmol) was added dropwise. The mixture was stirred at 25° C. for 1 hour and cooled to −70° C. Intermediate C-7 (160 g, 350 mmol) in toluene (500 mL) was added maintaining the temperature below −60° C. The resulting mixture was stirred at −70° C. for 1 hour. Ethylmagnesium bromide (350 mL, 3.0 M in diethyl ether, 1.05 mmol) was added dropwise maintaining the temperature below −60° C. and stirring was continued at −70° C. for another 1 hour. The reaction mixture was quenched with saturated citric acid (2 L) at −70° C., warmed slowly to 25° C., and extracted with ethyl acetate (500 mL×3). The combined organic layers were washed with brine (200 mL), dried over Na$_2$SO$_4$, filtered and concentrated. The residue was purified by silica gel chromatography (0%~30% EtOAc in PE) to afford Intermediate C-8 (153 g, 90%) as an off-white solid. A small sample of this material (300 mg) was purified by re-crystallization from MeCN (2 mL) to give Intermediate C-8 (200 mg) as an off-white solid.

$^1$H NMR (400 MHz, CDCl$_3$) δ 7.95-7.85 (m, 2H), 7.70-7.60 (m, 1H), 7.60-7.50 (m, 2H), 3.20-3.10 (m, 1H), 2.90-2.80 (m, 1H), 2.15-2.05 (m, 1H), 1.95-1.85 (m, 1H), 1.75-1.60 (m, 3H), 1.55-1.40 (m, 6H), 1.40-1.15 (m, 11H), 1.15-0.95 (m, 7H), 0.88 (t, J=7.2 Hz, 3H), 0.81 (s, 3H), 0.65-0.55 (m, 4H).

LCMS Rt=1.194 min in 2.0 min chromatography, 30-90 AB, purity 100%, MS ESI calcd. for C$_{30}$H$_{48}$O$_4$S[M+H$_2$O]$^+$ 504, found 504.

Example 4. Synthesis of Compound 1

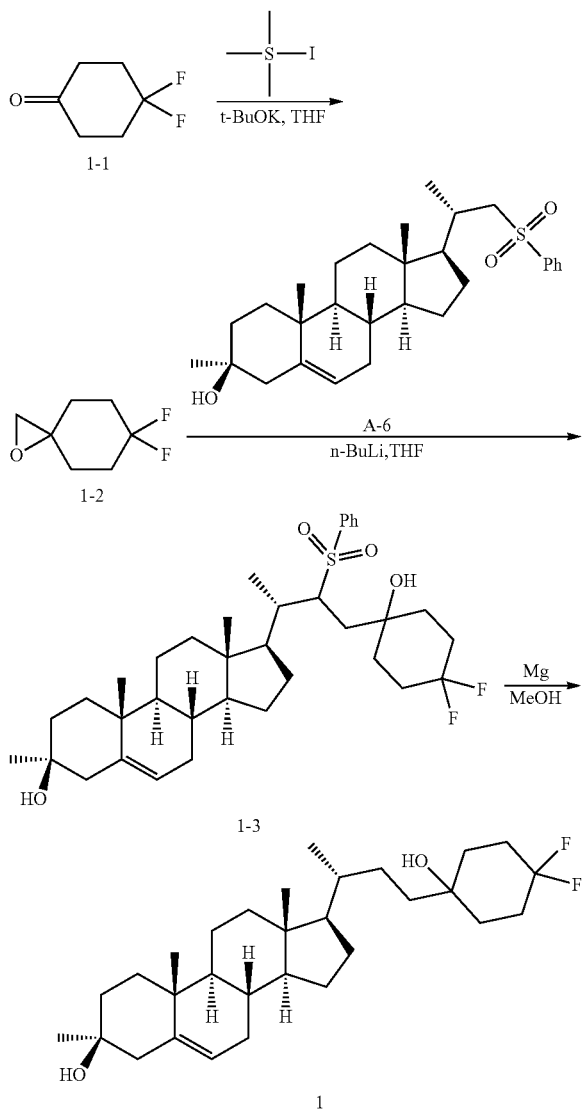

Step 1. Synthesis of Intermediate 1-2. To a suspension of Me$_3$SI (3.93 g, 19.3 mmol) in THF (20 mL) was added a solution of t-BuOK (3.33 g, 29.8 mmol) in THF (10 mL) under N$_2$ at 15° C. and the resulting suspension was stirred at 15° C. for 30 mins. A solution of Intermediate 1-1 (2 g, 14.9 mmol) in THF (5 mL) was added dropwise at 15° C. and the mixture was stirred at 15° C. for 16 hrs. The mixture was quenched with saturated NH$_4$Cl (50 mL) and extracted with EtOAc (3×20 mL). The combined organic phases were dried over Na$_2$SO$_4$, filtered, and concentrated to give Intermediate 1-2 (1.8 g, 82%) as a brown solid.

$^1$H NMR (400 MHz, CDCl$_3$) δ 2.72 (s, 2H), 2.20-1.85 (m, 8H).

Step 2. Synthesis of Intermediate 1-3. To a flask containing THF (5 mL) was added n-BuLi (2.5 M, 1.59 mmol, 0.636 mL) under N$_2$ at −70° C. A suspension of A-6 (0.637 mmol, 300 mg) in THF (4 mL) was added dropwise to give a light yellow suspension. After stirring at −70° C. for 30 mins, a solution of Intermediate 1-2 (0.764 mmol, 113 mg) in THF (1 mL) was added dropwise and the reaction was stirred at 15° C. for 12 hrs. The reaction was quenched with saturated NH$_4$Cl (30 mL) and extracted with EtOAc (10 mL×3). The combined organic layers were dried over Na$_2$SO$_4$, filtered and concentrated to give Intermediate 1-3 (400 mg, crude) as light yellow solid, which was used directly for the next step.

Step 3. Synthesis of Compound 1. To a solution of Intermediate 1-3 (400 mg, 0.646 mmol) in MeOH (5 mL) was added Mg powder (930 mg, 38.76 mmol) at 60° C. and the mixture was stirred at 60° C. for 16 hrs. The reaction was quenched with HCl (50 mL, TN) and extracted with DCM (2×30 mL). The combined organic phases were dried over Na$_2$SO$_4$, filtered, concentrated and the residue was purified by silica gel chromatography (0-10% EtOAc in PE) to give 50 mg impure product, which was purified by SFC (column: AD (250 mm*30 mm, 5 um), gradient: 0-40% B (A=0.05% NH$_3$/H$_2$O, B=MeOH); FlowRate (mL/min): 60) to give Compound 1 (32 mg, 10%) as an off-white solid.

$^1$H NMR (400 MHz, CDCl$_3$) δ 5.31-5.29 (m, 1H), 2.43-2.40 (m, 1H), 2.20-2.02 (m, 4H), 2.00-1.73 (m, 5H), 1.72-1.61 (m, 5H), 1.60-1.46 (m, 10H), 1.45-1.22 (m, 3H), 1.21-1.06 (m, 8H), 1.05-0.96 (m, 3H), 0.95-0.90 (m, 5H), 0.68 (s, 3H). LCMS Rt=1.256 min in 2.0 min chromatography, 30-90AB_ELSD, purity 100%, MS ESI calcd. for C$_{30}$H$_{45}$F$_2$[M+H−2H$_2$O]$^+$ 443, found 443.

Example 5. Synthesis of Compound 2

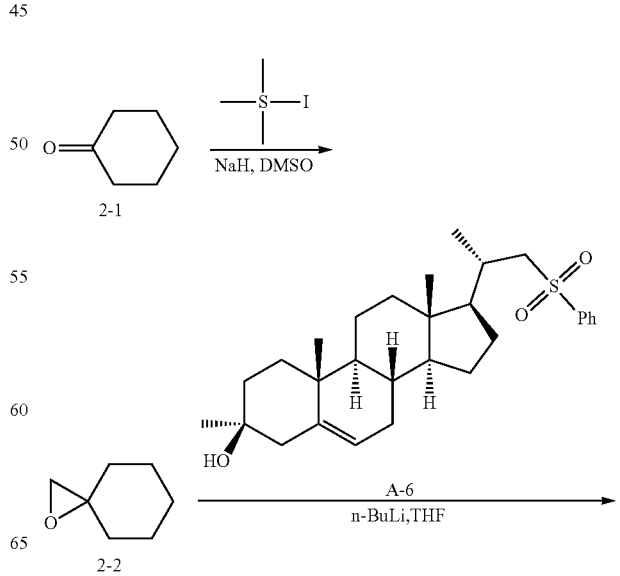

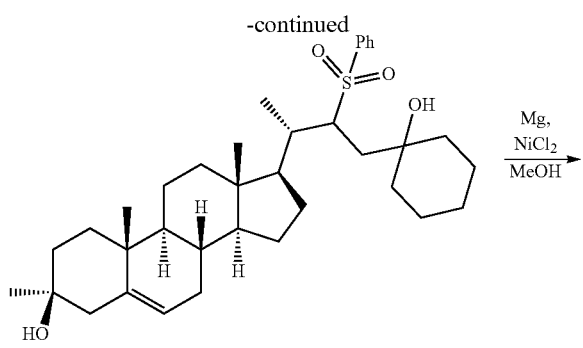

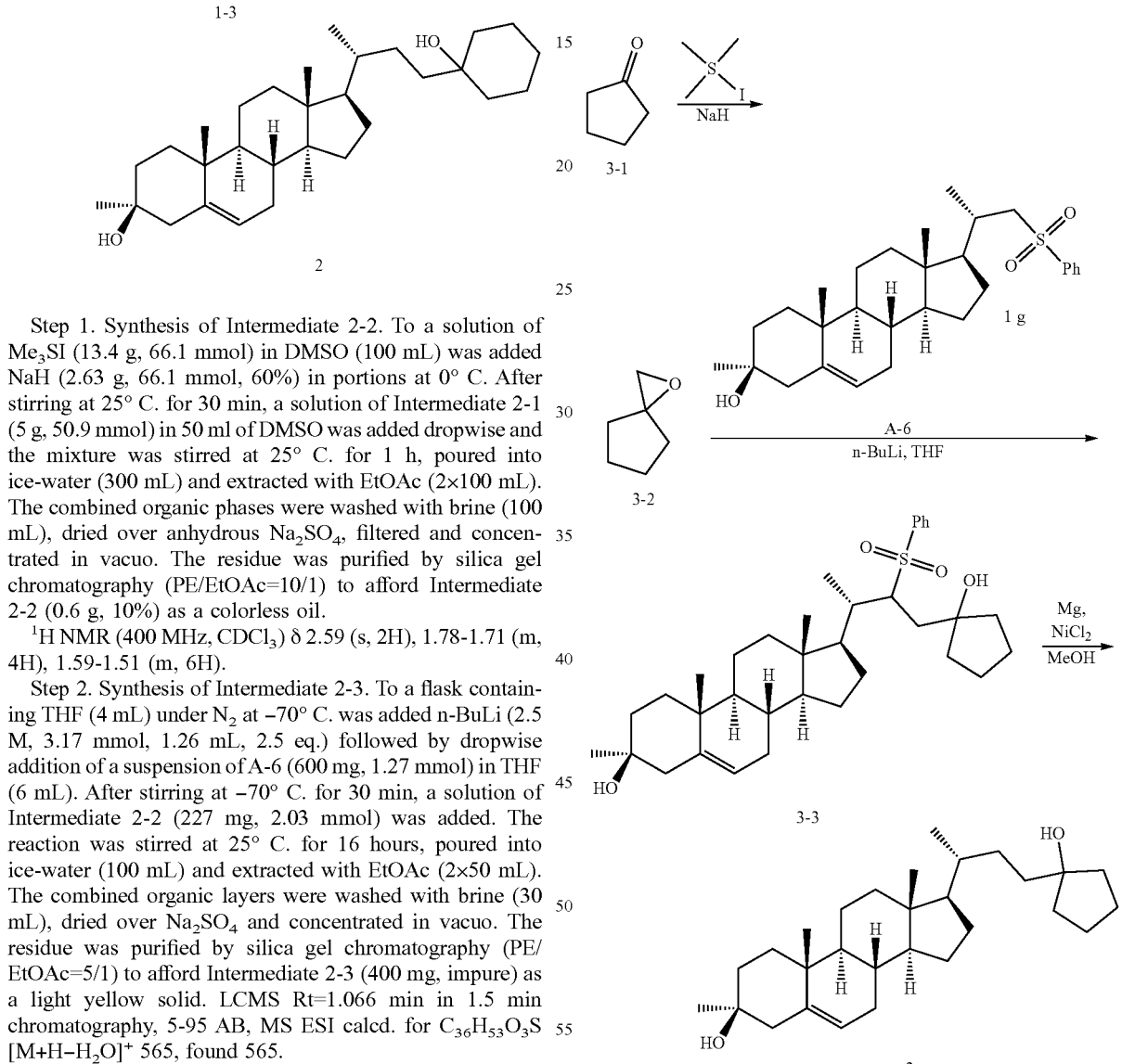

Step 1. Synthesis of Intermediate 2-2. To a solution of Me₃SI (13.4 g, 66.1 mmol) in DMSO (100 mL) was added NaH (2.63 g, 66.1 mmol, 60%) in portions at 0° C. After stirring at 25° C. for 30 min, a solution of Intermediate 2-1 (5 g, 50.9 mmol) in 50 ml of DMSO was added dropwise and the mixture was stirred at 25° C. for 1 h, poured into ice-water (300 mL) and extracted with EtOAc (2×100 mL). The combined organic phases were washed with brine (100 mL), dried over anhydrous Na₂SO₄, filtered and concentrated in vacuo. The residue was purified by silica gel chromatography (PE/EtOAc=10/1) to afford Intermediate 2-2 (0.6 g, 10%) as a colorless oil.

¹H NMR (400 MHz, CDCl₃) δ 2.59 (s, 2H), 1.78-1.71 (m, 4H), 1.59-1.51 (m, 6H).

Step 2. Synthesis of Intermediate 2-3. To a flask containing THF (4 mL) under N₂ at −70° C. was added n-BuLi (2.5 M, 3.17 mmol, 1.26 mL, 2.5 eq.) followed by dropwise addition of a suspension of A-6 (600 mg, 1.27 mmol) in THF (6 mL). After stirring at −70° C. for 30 min, a solution of Intermediate 2-2 (227 mg, 2.03 mmol) was added. The reaction was stirred at 25° C. for 16 hours, poured into ice-water (100 mL) and extracted with EtOAc (2×50 mL). The combined organic layers were washed with brine (30 mL), dried over Na₂SO₄ and concentrated in vacuo. The residue was purified by silica gel chromatography (PE/EtOAc=5/1) to afford Intermediate 2-3 (400 mg, impure) as a light yellow solid. LCMS Rt=1.066 min in 1.5 min chromatography, 5-95 AB, MS ESI calcd. for C₃₆H₅₃O₃S [M+H−H₂O]⁺ 565, found 565.

Step 3. Synthesis of Compound 2. To a solution of Intermediate 2-3 (400 mg, 0.69 mmol) in 10 mL of dry methanol, magnesium turnings (492 mg, 20.5 mmol) (activated with 0.5% aqueous HCl, water, dry ethanol, and MTBE) and NiCl₂ (44.4 mg, 0.34 mmol) were added under N₂ and the reaction was stirred at 50° C. for 1 h. The reaction was quenched at 10° C. by dropwise addition of 2M HCl (50 mL) until the complete dissolution of all solids. The mixture was extracted with EtOAc (50 mL) and the organic layer was washed with saturated NaHCO₃ (50 mL), brine (50 mL), dried over Na₂SO₄, filtered and concentrated. The residue was purified by silica gel chromatography (PE/EtOAc=10/1) to afford Compound 2 (42 mg, 14%) as an off-white solid.

¹H NMR (400 MHz, CDCl₃) δ 5.31-5.30 (m, 1H), 2.44-2.41 (m, 1H), 2.02-1.93 (m, 3H), 1.86-1.58 (m, 6H), 1.52-1.36 (m, 16H), 1.32-1.25 (m, 3H), 1.18-1.07 (m, 9H), 1.03-0.92 (m, 8H), 0.68 (s, 3H). LCMS Rt=1.353 min in 2.0 min chromatography, 30-90 AB, MS ESI calcd. for C₃₀H₄₇ [M+H−2H₂O]⁺ 407, found 407.

Example 6. Synthesis of Compound 3

Step 1. Synthesis of Intermediate 3-2. To a mixture of trimethylsulfoxonium iodide (47.1 g, 231 mmol) in 100 mL of DMSO was added NaH (9.23 g, 60% in mineral oil, 231 mmol) portionwise at 10° C. under N₂. The mixture was stirred at 10° C. for 30 mins. Intermediate 3-1 (15 g, 178 mmol) in DMSO (50 mL) was added dropwise below 15° C. and the reaction mixture was stirred at 15° C. for 20 hrs. The reaction was quenched at 10° C. with water (200 mL) and extracted with MTBE (2×300 mL). The combined organic phases were washed with water (2×400 mL), brine (200 mL), dried over Na$_2$SO$_4$, filtered and concentrated in vacuo to give a residue, which was purified by silica gel chromatography (DCM) to give Intermediate 3-2 (11 g, impure) as a colorless oil.

$^1$H NMR (400 MHz, CDCl$_3$) δ 2.83 (s, 2H), 1.95-1.77 (m, 4H), 1.74-1.60 (m, 4H).

Step 2. Synthesis of Intermediate 3-3. To a flask containing THF (4 mL) under N$_2$ at −70° C. was added n-BuLi (2.5 M, 5.30 mmol, 2.11 mL), followed by dropwise addition of a suspension of A-6 (2.12 mmol, 1 g) in THF (10 mL). After stirring at −70° C. for 30 mins, a solution of Intermediate 3-2 (4.24 mmol, 416 mg) in THF (4 mL) was added and the reaction was stirred at −70° C. for 10 mins and at 25° C. for 16 hrs. The reaction was quenched with water (10 mL) and extracted with EtOAc (3×50 mL). The combined organic phases were washed with brine (100 mL), dried over Na$_2$SO$_4$, filtered and concentrated in vacuo to give Intermediate 3-3 (1.2 g, crude) as a yellow solid. LCMS Rt=1.161 min & 1.222 min in 2.0 min chromatography, 30-90 AB, 28%, MS ESI calcd. for C$_{35}$H$_{52}$O$_4$SNa [M+Na]$^+$ 591, found 591.

Step 3. Synthesis of Compound 3. To a solution of Intermediate 3-3 (1.2 g, 2.10 mmol) in 50 mL of dry MeOH and 25 mL of THF, magnesium turnings (3.06 g, 126 mol) (activated with 0.5% aqueous HCl, water, dry ethanol, and MTBE) and NiCl$_2$ (54.4 mg, 0.42 mmol) were added under N$_2$ at 50° C. to initiate continuous hydrogen generation. The reaction was quenched at 10° C. by addition of 1 M HCl (200 mL) until the complete dissolution of all solids. The mixture was extracted with EtOAc (2×200 mL). The combined organic layers were washed with saturated NaHCO$_3$ (500 mL), brine (500 mL), dried over Na$_2$SO$_4$, filtered and concentrated in vacuo to give Compound 3 (600 mg, crude), which was purified by column chromatography on silica gel (PE/EtOAc=5/1) to give a product (150 mg, impure) as an off-white solid. The impure product was purified by SFC (Column: AD (250 mm*30 mm, 5 um); Condition: Base-ETOH, 40% B; FlowRate (ml/min): 60 mL/min) to give 30 mg of the product. The product was washed with n-hexane (5 mL) to give Compound 3 (3 mg, 0.3%).

$^1$H NMR (400 MHz, CDCl$_3$) δ 5.34-5.28 (m, 1H), 2.46-2.35 (m, 1H), 2.05-1.93 (m, 3H), 1.89-1.59 (m, 12H), 1.53-1.24 (m, 11H), 1.21-0.99 (m, 13H), 0.96-0.89 (m, 4H), 0.68 (s, 3H).

LCMS Rt=1.161 min & 1.295 min in 2.0 min chromatography, 30-90 AB_E, MS ESI calcd. for C$_{29}$H$_{45}$ [M+H−2H$_2$O]$^+$ 393, found 393.

Example 7. Synthesis of Compound 4

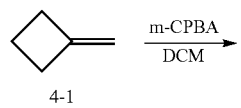

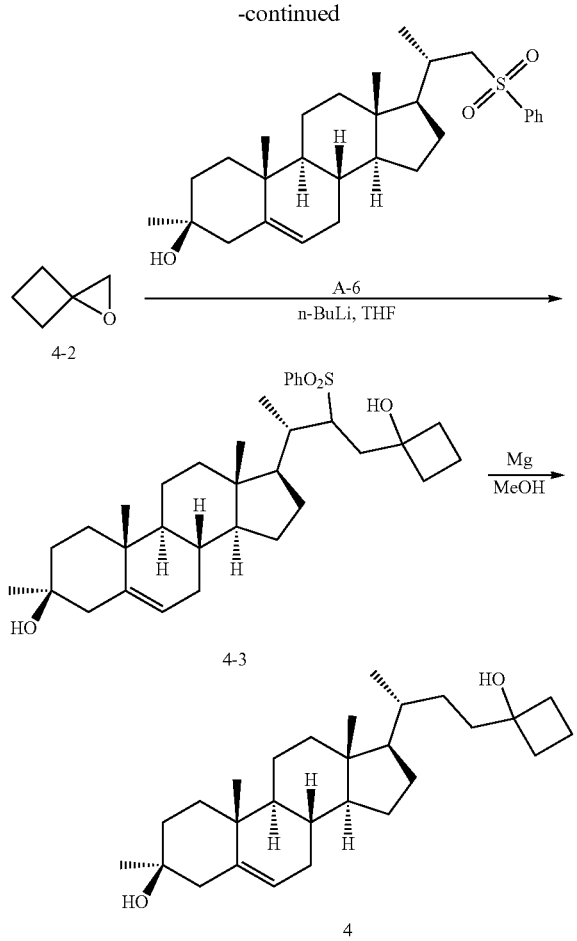

Step 1. Synthesis of Intermediate 4-2. To a solution of Intermediate 4-1 (1 g, 14.6 mmol) in DCM (30 mL) was added m-CPBA (3.77 g, 21.9 mmol) and the mixture was stirred at 25° C. for 16 hrs. The reaction mixture was filtered, and the filtrate was distilled in vacuo to give a solution of Intermediate 4-2 in DCM. The solution was distilled under normal pressure to give a solution of Intermediate 4-2 (5 g, 2% solution in DCM calculated from $^1$HNMR, 8% yield calculated from HNMR).

$^1$H NMR (400 MHz, CDCl$_3$) δ 2.67 (s, 2H), 2.54-2.43 (m, 2H), 2.30-2.20 (m, 2H), 1.89-1.72 (m, 2H).

Step 2. Synthesis of Intermediate 4-3. To a solution of n-BuLi (2.5 M in hexane, 1.1 mL, 2.65 mmol) in anhydrous THF (8 mL) under nitrogen at −78° C., A-6 (500 mg, 1.06 mmol) was added in one portion and the mixture was stirred at −78° C. for 0.5 hr. A solution of Intermediate 4-2 (5 g, 2% in DCM, 1.18 mmol) was added dropwise to the above mixture and the reaction was gradually warmed to 15° C. After stirring for 16 hrs the reaction was quenched with saturated NH$_4$Cl (20 mL) and extracted with EtOAC (3×30 mL). The combined organic layers were dried over anhydrous Na$_2$SO$_4$, filtered and concentrated. The residue was purified by column chromatography on silica gel (PE:EtOAc=9:1) to give Intermediate 4-3 (100 mg, 17%) as an off-white solid. LCMS Rt=1.131 min in 2.0 min chromatography, 30-90 AB, MS ESI calcd. for C$_{34}$H$_{49}$O$_3$S [M+H−H$_2$O]$^+$ 537, found 537.

Step 3. Synthesis of Compound 4. To a solution of Intermediate 4-3 (100 mg, 0.180 mmol) in anhydrous MeOH (5 mL) under nitrogen was added magnesium powder (260 mg, 10.7 mmol). The mixture was stirred at 60° C. for 2 hrs, cooled to room temperature, neutralized with 1 M HCl and extracted with EtOAc (4×20 mL). The combined organic layers were washed with water (40 mL) and brine (40 mL), dried over anhydrous sodium sulfate, filtered and concentrated. The residue was purified by column chromatography on silica gel (PE:EtOAc=10:1) to afford a residue, which was triturated with n-hexane to give Compound 4 (23 mg, 31%) as an off-white solid.

$^1$H NMR (400 MHz, CDCl$_3$) δ 5.34-5.26 (m, 1H), 2.46-2.37 (m, 1H), 2.09-1.57 (m, 14H), 1.54-1.23 (m, 11H), 1.21-1.05 (m, 8H), 1.04-0.90 (m, 8H), 0.69 (s, 3H). LCMS Rt=1.230 min in 2.0 min chromatography, 30-90 AB, MS ESI calcd. for C$_{28}$H$_{43}$ [M+H−2H$_2$O]$^+$ 379, found 379.

Example 8. Synthesis of Compound 5

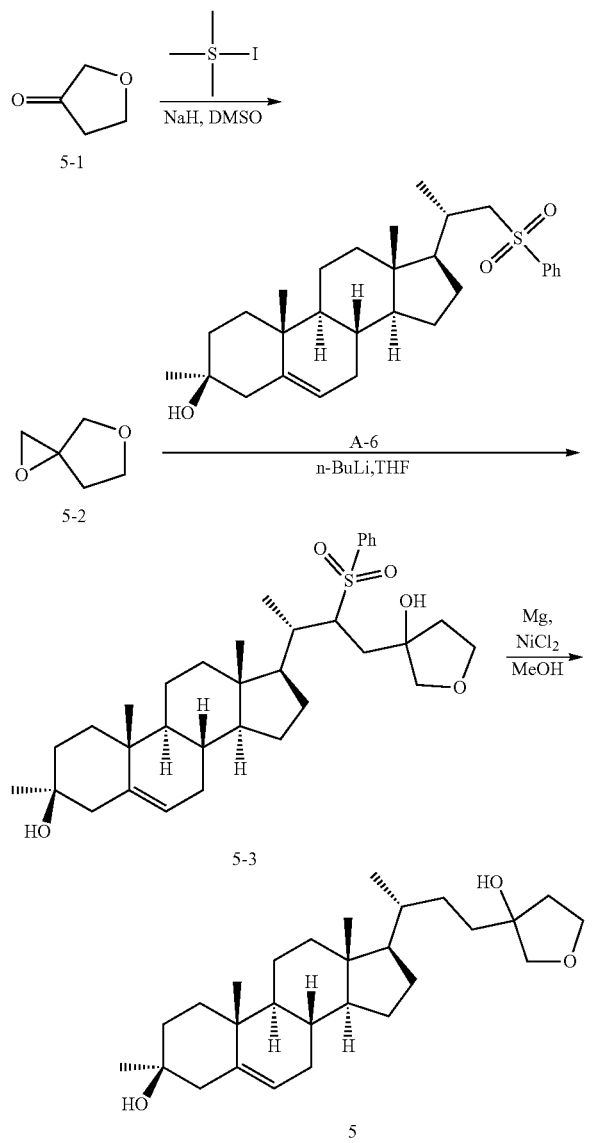

Step 1. Synthesis of Intermediate 5-2. To a mixture of trimethylsulfoxonium iodide (28.3 g, 139 mmol) in DMSO (60 mL) was added NaH (5.55 g, 60% in mineral oil, 139 mmol) in portions at 5° C. under N$_2$ and the mixture was stirred at 5° C. for 30 mins. Dihydrofuran-3(2H)-one (10 g, 116 mmol) in DMSO (40 mL) was added dropwise while maintaining the temperature below 15° C. and the resulting mixture was stirred at 15° C. for 20 hrs. The reaction was quenched at 10° C. with water (200 mL) and extracted with MTBE (2×200 mL). The combined organic phases were washed with brine (200 mL), dried over Na$_2$SO$_4$, filtered and concentrated and the residue was purified by silica gel chromatography (0%~40% EtOAc in PE) to afford Intermediate 5-2 (100 mg, 1%) as a colorless oil.

$^1$H NMR (400 MHz, CDCl$_3$) δ 4.12-3.93 (m, 3H), 3.68 (d, J=10.4 Hz, 1H), 3.05 (d, J=4.4 Hz, 1H), 2.96 (d, J=4.4 Hz, 1H), 2.37-2.25 (m, 1H), 2.02-1.92 (m, 1H).

Step 2. Synthesis of Intermediate 5-3. To a flask containing THF (2 mL) under N$_2$ at −78° C. was added n-BuLi (0.9 mL, 2.22 mmol, 2.5 M) followed by a suspension of A-6 (300 mg, 0.637 mmol) in THF (4 mL), giving a light yellow suspension. After stirring at −78° C. for 30 mins, a solution of Intermediate 5-2 (100 mg, 1.01 mmol) in THF (2 mL) was added and the reaction was stirred at −78° C. for 10 mins and at 15° C. for 16 hrs. The reaction was quenched with saturated NH$_4$Cl (20 mL), extracted with EtOAc (3×20 mL) and the combined organic phases were washed with brine (50 mL), dried over Na$_2$SO$_4$, filtered and concentrated to give crude Intermediate 5-3 (300 mg) as a yellow solid, which was used directly in next step.

LCMS Rt=0.907 min in 1.5 min chromatography, 5-95 AB, MS ESI calcd. for C$_{34}$H$_{49}$O$_4$S [M+H−H$_2$O]$^+$ 553, found 553.

Step 3. Synthesis of Compound 5. To a solution of Intermediate 5-3 (300 mg, 0.525 mmol) in 20 mL of dry MeOH under N$_2$, magnesium turnings (127 mg, 5.24 mmol) (activated with 0.5% aqueous HCl, water, dry EtOH, and MTBE) and NiCl$_2$ (13.6 mg, 0.10 mmol) were added with stirring at 55° C. to initiate continuous hydrogen generation. After four batches of 127 mg of magnesium turnings were added most of the starting material was consumed. The reaction was quenched by adding 2M HCl (50 mL) until the complete dissolution of all solids. The mixture was extracted with DCM (3×20 mL) and the combined organic phases were washed with brine (50 mL), dried over Na$_2$SO$_4$, filtered and concentrated. The residue was purified by silica gel chromatography (0%~50% EtOAc in PE) to afford Compound 5 (34 mg, 15%) as an off-white solid.

$^1$H NMR (400 MHz, CDCl$_3$) δ 5.37-5.24 (m, 1H), 4.08-3.98 (m, 1H), 3.94-3.84 (m, 1H), 3.74-3.65 (m, 1H), 3.59-3.51 (m, 1H), 2.48-2.37 (m, 1H), 2.06-1.67 (m, 9H), 1.66-1.38 (m, 13H), 1.34-1.07 (m, 8H), 1.06-0.90 (m, 7H), 0.68 (s, 3H). LCMS Rt=1.111 min in 2 min chromatography, 30-90AB_E, MS ESI calcd. for C$_{30}$H$_{49}$O$_3$NNa [M+MeCN+Na]$^+$ 494, found 494.

Example 9. Preparation of Compound 5-A and 5-B

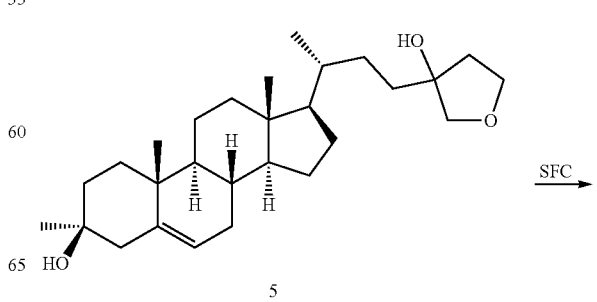

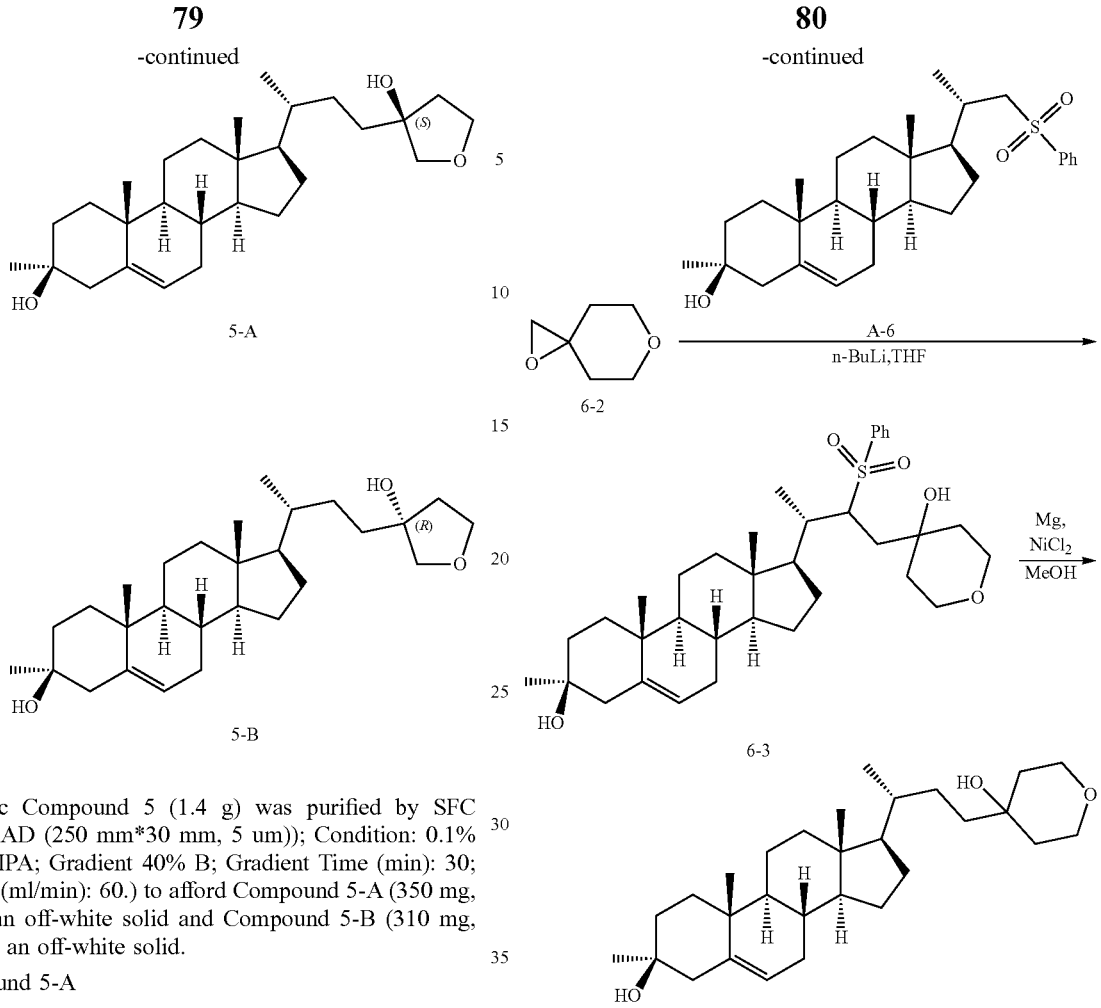

Racemic Compound 5 (1.4 g) was purified by SFC (Column: AD (250 mm*30 mm, 5 um)); Condition: 0.1% NH₃H₂O IPA; Gradient 40% B; Gradient Time (min): 30; FlowRate (ml/min): 60.) to afford Compound 5-A (350 mg, 15%) as an off-white solid and Compound 5-B (310 mg, 14%) as a an off-white solid.

Compound 5-A $^1$H NMR (400 MHz, CDCl$_3$) δ 5.33-5.28 (m, 1H), 4.10-4.00 (m, 1H), 3.93-3.85 (m, 1H), 3.69 (d, J=9.2 Hz, 1H), 3.54 (d, J=9.2 Hz, 1H), 2.46-2.38 (m, 1H), 2.04-1.88 (m, 5H), 1.87-1.56 (m, 9H), 1.53-1.23 (m, 7H), 1.21-1.09 (m, 7H), 1.08-0.89 (m, 9H), 0.68 (s, 3H). LCMS Rt=1.091 min in 2 min chromatography, 30-90AB E, purity 100%, MS ESI calcd. for C$_{28}$H$_{46}$O$_3$Na [M+Na]$^+$ 453, found 453.

Compound 5-B $^1$H NMR (400 MHz, CDCl$_3$) δ 5.32-5.28 (m, 1H), 4.10-4.00 (m, 1H), 3.93-3.85 (m, 1H), 3.70 (d, J=9.2 Hz, 1H), 3.55 (d, J=9.2 Hz, 1H), 2.45-2.39 (m, 1H), 2.04-1.83 (m, 6H), 1.81-1.63 (m, 4H), 1.61-1.54 (m, 5H), 1.52-1.37 (m, 6H), 1.26-1.08 (m, 8H), 1.05-0.92 (m, 8H), 0.68 (s, 3H).

LCMS Rt=1.093 min in 2 min chromatography, 30-90AB_E, purity 100%, MS ESI calcd. for C$_{28}$H$_{43}$O [M+H−2H$_2$O]$^1$ 395, found 395.

Example 10. Synthesis of Compound 6

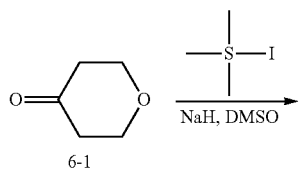

Step 1. Synthesis of Intermediate 6-2. To a mixture of trimethylsulfoxonium iodide (12.2 g, 59.8 mmol) in DMSO (40 mL) at 5° C. under N$_2$, NaH (2.38 g, 60% in mineral oil, 59.8 mmol) was added portionwise and the mixture was stirred at 5° C. for 30 mins. Intermediate 6-1 (5 g, 49.9 mmol) in DMSO (40 mL) was added dropwise maintaining the temperature below 15° C. and the reaction mixture was stirred at 15° C. for 20 hrs. The reaction was quenched at 10° C. with water (200 mL) and extracted with MTBE (2×200 mL). The combined organic phases were washed with brine (200 mL), dried over Na$_2$SO$_4$, filtered and concentrated and the resulting residue was purified by silica gel chromatography (0%~50% EtOAc in PE) to afford Intermediate 6-2 (1.5 g, 26%) as colorless oil.

$^1$H NMR (400 MHz, CDCl$_3$) δ 3.93-3.76 (m, 4H), 2.69 (s, 2H), 1.94-1.81 (m, 2H), 1.58-1.48 (m, 2H).

Step 2. Synthesis of Intermediate 6-3. To a flask containing THF (5 mL) under N$_2$ at −78° C., n-BuLi (2.96 mL, 7.42 mmol, 2.5 M) was added, followed by dropwise addition of a suspension of A-6 (1 g, 2.12 mmol) in THF (10 mL) to give a light yellow suspension. After stirring at −78° C. for 30 mins, a solution of Intermediate 6-2 (483 mg, 4.24 mmol) in THF (5 mL) was added and the reaction was stirred at −78° C. for 10 min and at 15° C. for 16 hrs. The reaction was quenched with saturated NH$_4$Cl (50 mL) and extracted with EtOAc (3×30 mL). The combined organic phases were washed with brine (50 mL), dried over anhydrous Na$_2$SO$_4$, filtered and concentrated to give crude Intermediate 6-3 (1 g)

as a yellow solid, which was used directly in next step. LCMS Rt=2.423 min in 3.0 min chromatography, 10-80 AB, MS ESI calcd. for $C_{35}H_{52}O_5SNa$ [M+Na]$^+$ 607, found 607.

Step 3. Synthesis of Compound 6 To a solution of Intermediate 6-3 (1 g, 1.70 mmol) in 20 mL of anhydrous MeOH under N$_2$, magnesium turnings (410 mg, 16.9 mmol) (activated with 0.5% aqueous HCl, water, anhydrous ethanol, and MTBE) and NiCl$_2$ (44.0 mg, 0.34 mmol) were added with stirring at 55° C. to initiate continuous hydrogen generation. After four batches of magnesium turnings (410 mg overall) were added, the reaction was quenched at 10° C. by dropwise addition of 2M HCl (80 mL) until the complete dissolution of all solids. The mixture was extracted with DCM (3×50 mL) and the combined organic phases were washed with brine (80 mL), dried over Na$_2$SO$_4$, filtered and concentrated. The resulting residue was purified by silica gel chromatography (0%~70% EtOAc in PE) to afford Compound 6 (200 mg, 26%) as an off-white solid.

$^1$H NMR (400 MHz, DMSO-d$_6$) δ 5.24-5.15 (m, 1H), 4.34 (s, 1H), 4.02 (s, 1H), 3.64-3.47 (m, 4H), 2.30-2.23 (m, 1H), 2.00-1.75 (m, 5H), 1.70-1.24 (m, 14H), 1.20-0.83 (m, 18H), 0.63 (s, 3H). LCMS Rt=2.043 min in 3.0 min chromatography, 10-80 AB, MS ESI calcd. for $C_{29}H_{45}O$ [M+H−2H$_2$O]$^+$ 409, found 409.

Example 11. Synthesis of Compound 7

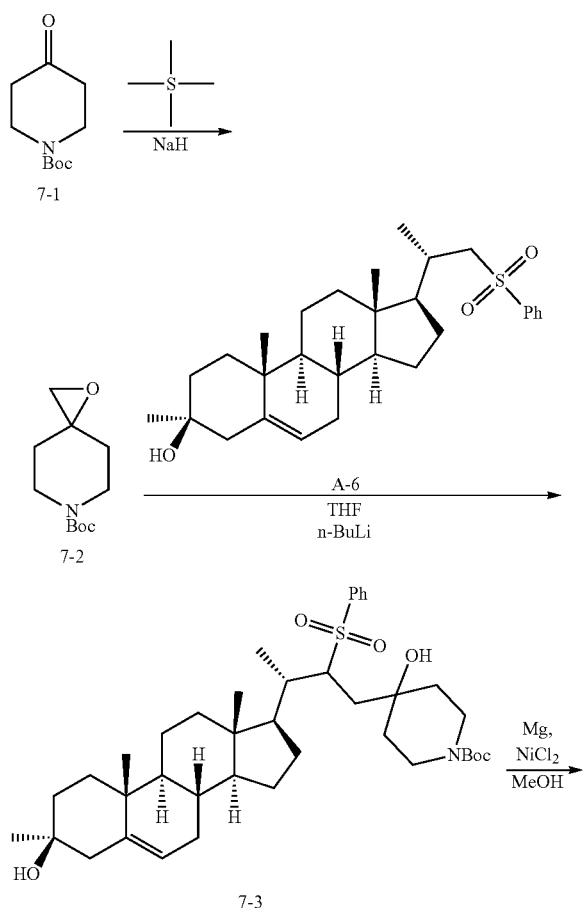

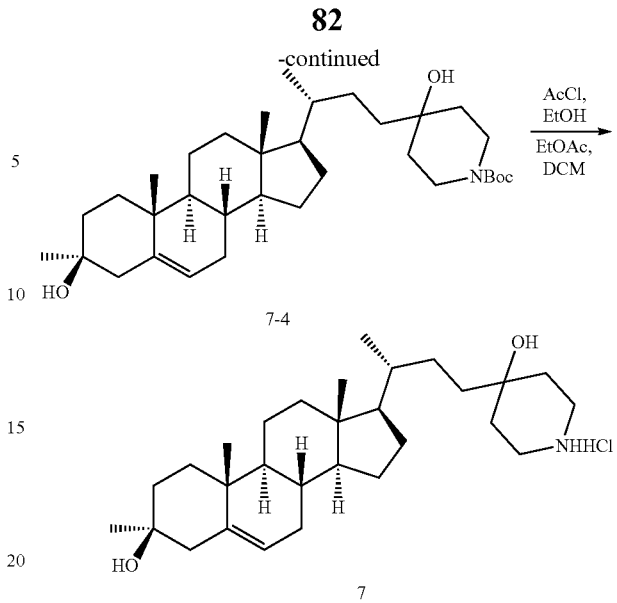

Step 1. Synthesis of Intermediate 7-2. To a solution of trimethylsulfoxonium iodide (26.5 g, 130 mmol) in 50 mL of DMSO at 10° C. under N$_2$, NaH (5.18 g, 60% in mineral oil, 130 mmol) was added portionwise and the mixture was stirred at 10° C. for 30 mins. Intermediate 7-1 (20 g, 100 mmol) in DMSO (50 mL) was added dropwise maintaining the temperature below 15° C. and stirring was continued at 15° C. for 20 hrs. The reaction was quenched at 10° C. with water (200 mL) and extracted with MTBE (2×300 mL). The combined organic phases were washed with water (2×400 mL), brine (200 mL), dried over Na$_2$SO$_4$, filtered and concentrated in vacuo to give a residue, which was purified by silica gel chromatography (PE:EtOAc=6:1) to give Intermediate 7-2 (15 g, 70%) as an off-white solid.

$^1$H NMR (400 MHz, CDCl$_3$) δ 3.77-3.66 (m, 2H), 3.43 (m, 2H), 2.69 (s, 2H), 1.86-1.72 (m, 2H), 1.52-1.39 (m, 11H).

Step 2. Synthesis of Intermediate 7-3. To a solution of n-BuLi (2.5 M in hexane, 4.2 mL, 10.6 mmol) in anhydrous THF (20 mL) at −70° C. under nitrogen A-6 (2 g, 4.24 mmol) was added in one portion and the mixture was stirred at −70° C. for 30 mins. Intermediate 7-2 (1.80 g, 8.48 mmol) was added and the resulting mixture was gradually warmed to 15° C. and stirred for an additional 16 hours. The reaction was quenched with saturated NH$_4$Cl (30 mL) and extracted with EtOAc (3×40 mL). The combined organic layers were dried over anhydrous Na$_2$SO$_4$, filtered and concentrated. The residue was purified by column chromatography on silica gel (PE:THF=5:1) to give Intermediate 7-3 (2.3 g, 79%) as an off-white solid.

$^1$H NMR (400 MHz, CDCl$_3$) δ 7.96-7.87 (m, 2H), 7.72-7.55 (m, 3H), 5.31-5.24 (m, 1H), 4.00-3.83 (m, 2H), 3.43-3.32 (m, 1H), 3.30-3.06 (m, 2H), 2.44-2.24 (m, 2H), 1.99-1.87 (m, 3H), 1.80-1.50 (m, 1H), 1.49-1.42 (m, 12H), 1.40-1.25 (m, 4H), 1.18-0.80 (m, 15H), 0.43 (s, 3H).

Step 3. Synthesis of Intermediate 7-4. To a solution of Intermediate 7-3 (2.3 g, 3.36 mmol) and nickel(II) chloride (435 mg, 3.36 mmol) in anhydrous MeOH (30 mL) and THF (10 mL) under nitrogen at 45° C. was added a single portion of magnesium turnings (3.25 g, 134 mmol). The internal temperature rose to 60° C. and vigorous gas evolution was observed. The mixture was stirred at 60° C. for 3 hrs, cooled to room temperature, quenched with 1 M HCl (100 mL) and extracted with EtOAc (2×100 mL). The combined organic layers were washed with saturated NaHCO$_3$ (100 mL) and brine (100 mL), dried over Na$_2$SO$_4$, filtered and concentrated. The residue was purified by column chromatography on silica gel (PE:THF=6:1) to give Intermediate 7-4 (1.1 g, 60%) as an off-white solid.

$^1$H NMR (400 MHz, CDCl$_3$) δ 5.34-5.27 (m, 1H), 3.91-3.66 (m, 2H), 3.23-3.07 (m, 2H), 2.47-2.38 (m, 1H), 2.03-1.91 (m, 3H), 1.88-1.65 (m, 4H), 1.60-1.54 (m, 4H), 1.47-1.42 (m, 12H), 1.38-1.24 (m, 4H), 1.20-0.97 (m, 14H), 0.97-0.77 (m, 7H), 0.68 (s, 3H).

Step 4. Synthesis of Compound 7. To a solution of Intermediate 7-4 (1 g, 1.83 mmol) in EtOAc (8 mL) and DCM (8 mL) were added ethanol (843 mg, 18.3 mmol) and acetyl chloride (1.43 g, 18.3 mmol). The mixture was stirred at 15° C. for 16 hrs. The precipitated solid was collected by filtration and dried in vacuo to afford crude product (720 mg), which was triturated with methanol to give the hydrochloride of Compound 7 (260 mg, 30%) as an off-white solid.

$^1$H NMR (400 MHz, DMSO-d$_6$) δ 8.70-8.38 (m, 1H), 5.24-5.15 (m, 1H), 4.52-4.24 (m, 2H), 3.11-2.94 (m, 4H), 2.35-2.25 (m, 1H), 1.98-1.77 (m, 4H), 1.71-1.50 (m, 8H), 1.47-1.31 (m, 7H), 1.28-0.98 (m, 8H), 0.97-0.86 (m, 10H), 0.65 (s, 3H). LCMS Rt=1.054 min in 2.0 min chromatography, 10-80 AB, MS ESI calcd. for C$_{29}$H$_{50}$NO$_2$ [M+H]$^+$ 444, found 444.

Example 12. Synthesis of Compound 8

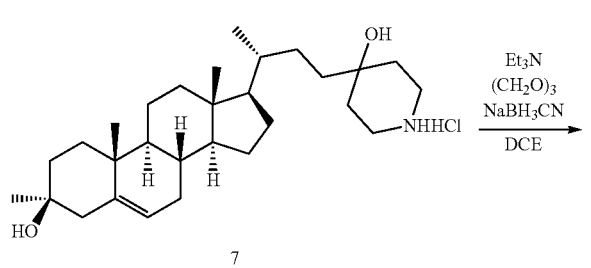

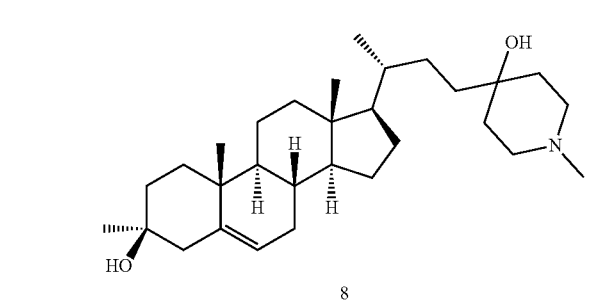

To a suspension of Compound 7 hydrochloride (50 mg, 0.104 mmol) in DCE (4 mL) were added Et$_3$N (21.0 mg, 0.208 mmol), paraformaldehyde (18.7 mg, 0.208 mmol) and NaBH$_3$CN (16.3 mg, 0.260 mmol) and the mixture was stirred at 25° C. for 16 hrs. The reaction mixture was neutralized with 1 M HCl and purified by preparative HPLC (Column: DuraShell 150*25 mm*5 um. Mobile phase: A: Water (0.1% TFA), B: ACN. Gradient: 35-60% B, 25 Min. Flow rate: 30 mL/min) to give Compound 8 (3 mg, 6%) as an off-white solid.

$^1$H NMR (400 MHz, CDCl$_3$) δ 5.34-5.26 (m, 1H), 3.44-3.32 (m, 2H), 3.19-3.04 (m, 2H), 2.78 (d, J=4.0 Hz, 3H), 2.48-2.37 (m, 1H), 2.16-1.92 (M, 5H), 1.86-1.56 (m, 9H), 1.51-1.35 (m, 7H), 1.31-1.04 (m, 10H), 1.04-0.87 (m, 8H), 0.67 (s, 3H). LCMS Rt=0.748 min in 2.0 min chromatography, 30-90 AB, MS ESI calcd. for C$_{30}$H$_{52}$NO$_2$ [M+H]$^+$ 458, found 458.

Example 13. Synthesis of Compound 9

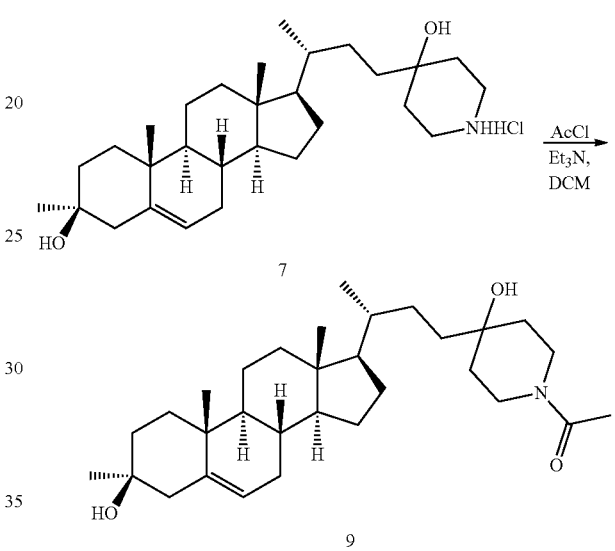

To a suspension of Compound 7 hydrochloride (50 mg, 0.104 mmol) in DCM (4 mL) were added Et$_3$N (31.5 mg, 0.312 mmol) and AcCl (16.3 mg, 0.208 mmol) and the mixture was stirred at 25° C. for 16 hrs. The reaction mixture was neutralized with 1 M HCl and purified by preparative HPLC (Column: DuraShell 150*25 mm*5 um. Mobile phase: A: Water (0.1% TFA), B: ACN. Gradient: 51-76% B, 25 Min. Flow rate: 30 mL/min) to give Compound 9 (15 mg, 30%) as an off-white solid.

$^1$H NMR (400 MHz, CDCl$_3$) δ 5.35-5.25 (m, 1H), 4.43-4.27 (m, 1H), 3.65-3.38 (m, 2H), 3.12-2.94 (m, 1H), 2.48-2.37 (m, 1H), 2.11 (s, 11H), 1.89-1.57 (m, 6H), 1.52-1.21 (m, 9H), 1.20-1.03 (m, 8H), 1.03-0.89 (m, 8H), 0.68 (s, 3H). LCMS Rt=1.036 min in 2.0 min chromatography, 30-90 AB, MS ESI calcd. for C$_{31}$H$_{52}$NO$_3$ [M+H]$^+$ 486, found 486.

Example 14. Synthesis of Compound 10

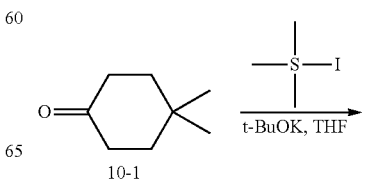

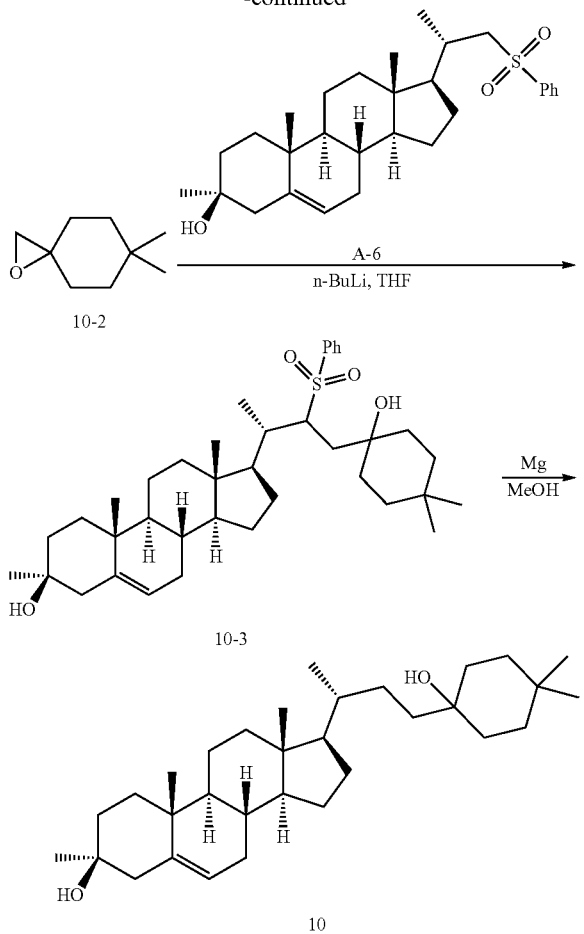

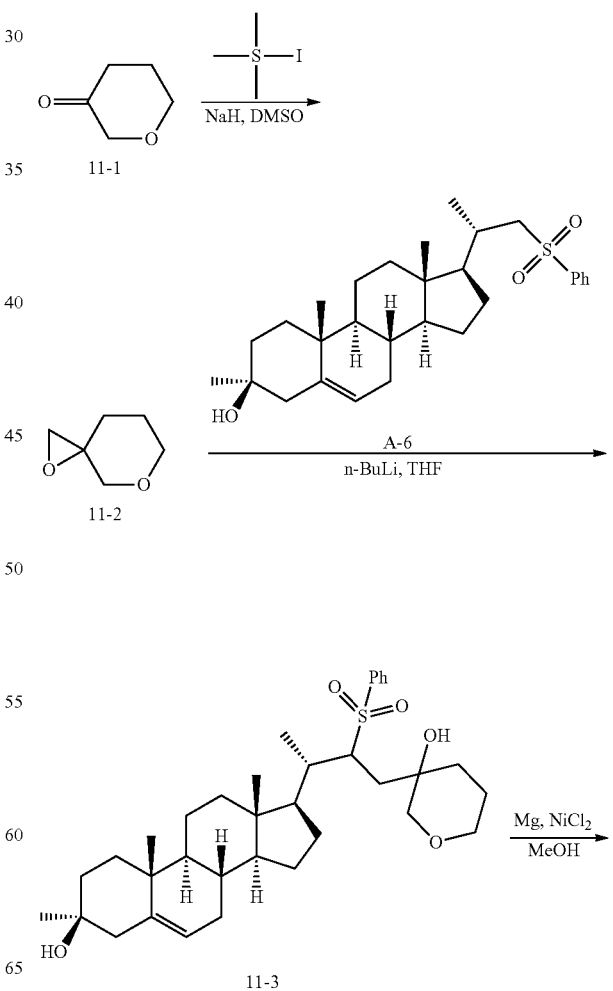

Step 1. Synthesis of Intermediate 10-2. To a suspension of t-BuOK (3.53 g, 31.6 mmol) in THF (30 mL) was added Me₃SI (4.18 g, 20.5 mmol) under N₂ and the suspension was stirred at 15° C. for 30 min. A solution of Intermediate 10-1 (2 g, 15.8 mmol) in 10 ml of THF was added dropwise and stirring was continued at 15° C. for 16 hrs. The reaction was quenched with saturated NH₄Cl (100 mL) and extracted with EtOAc (3×150 mL). The combined organic phases were dried over Na₂SO₄, filtered, and concentrated in vacuo to give Intermediate 10-2 (1.8 g, 81%) as a yellow liquid.

$^1$H NMR (400 MHz, CDCl$_3$) δ 2.58 (s, 2H), 1.90-1.80 (m, 1H), 1.70-1.55 (m, 2H), 1.54-1.45 (m, 3H), 1.40-1.30 (m, 2H), 1.00-0.90 (m, 6H).

Step 2. Synthesis of Intermediate 10-3. To a flask containing THF (0.5 mL) under N₂ at −70° C. was added n-BuLi (1.05 mL, 2.5 M, 2.65 mmol), followed by dropwise addition of a suspension of Intermediate A-6 (500 mg, 1.06 mmol) in THF (1 mL) to give a light yellow suspension. After stirring at −70° C. for 30 min, a solution of Intermediate 10-2 (178 mg, 1.27 mmol) in THF (1 mL) was added dropwise and the reaction was stirred at 15° C. for 12 hrs. The reaction was quenched with saturated NH₄Cl (10 mL) and extracted with EtOAc (3×10 mL). The combined organic layers were dried over Na₂SO₄, filtered and concentrated to give Intermediate 10-3 (500 mg, crude) as a yellow solid, which was used directly for the next step.

Step 3. Synthesis of Compound 10. To a solution of Intermediate 10-3 (500 mg, 0.818 mmol) and nickel (II) chloride (26.4 mg, 0.204 mmol) in dry methanol under N₂ (20 mL) was added magnesium powder (794 mg, 32.7 mmol) with stirring at 50° C. to initiate continuous hydrogen generation. After stirring at 60° C. for 1 hour the reaction was quenched at 10° C. by dropwise addition of 2M HCl (100 mL) until the complete dissolution of all solids. After extraction with EtOAc (2×150 mL), the combined organic layers were washed with sat. NaHCO₃ aq. (300 mL), brine (300 mL), dried over Na₂SO₄, filtered and concentrated in vacuo to give a yellow solid, which was purified by silica gel chromatography (PE/THF=4/1) to give 150 mg of white solid. 72 mg of the solid was purified by SFC (column: AD (250 mm*30 mm, 10 um)), gradient: 55-55% B (A=0.1% NH₃/H₂O, B=EtOH), flow rate: 80 mL/min) to give Compound 10 (39 mg) as an off-white solid.

$^1$H NMR (400 MHz, CDCl$_3$) δ 5.35-5.30 (m, 1H), 2.45-2.40 (m, 2H), 2.10-1.95 (m, 3H), 1.90-1.65 (m, 7H), 1.60-1.40 (m, 14H), 1.39-1.10 (m, 11H), 1.09-1.00 (m, 4H), 0.09-0.88 (m, 6H), 0.87 (s, 3H), 0.67 (m, 3H).

LCMS Rt=1.481 min in 2.0 min chromatography, 30-90 AB, purity 100%, MS ESI calcd. for C₃₂H₅₁ [M+H−2H₂O]⁻ 435, found 435.

Example 15. Synthesis of Compound 11

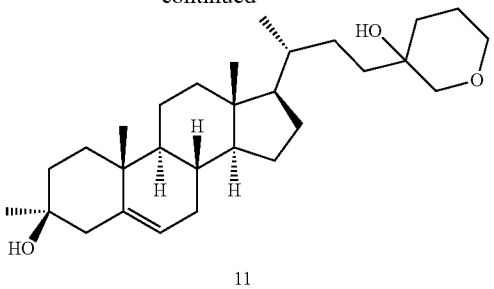

11

Step 1. Synthesis of Intermediate 11-2. To a mixture of trimethylsulfoxonium iodide (12.2 g, 59.8 mmol) in DMSO (40 mL) was added NaH (2.38 g, 60% in mineral oil, 59.8 mmol) portionwise at 5° C. under $N_2$ and the mixture was stirred at 5° C. for 30 mins. Intermediate 11-1 (5 g, 49.9 mmol) in DMSO (40 mL) was added dropwise maintaining the temperature below 15° C. and stirring was continued at 15° C. for 20 hrs. The reaction was quenched at 10° C. with water (200 mL) and extracted with DCM (2×200 mL). The combined organic phases were washed with brine (200 mL), dried over $Na_2SO_4$, filtered and concentrated. The residue was purified by silica gel chromatography (0%~50% EtOAc in PE) to afford Intermediate 11-2 (2 g, 35%) as a colorless oil.

$^1$H NMR (400 MHz, CDCl$_3$) δ 3.81-3.60 (m, 3H), 3.49 (d, J=12.0 Hz, 1H), 2.73-2.65 (m, 2H), 2.03-1.82 (m, 2H), 1.81-1.62 (m, 2H).

Step 2. Synthesis of Intermediate 11-3. To a flask containing THF (3 mL) under $N_2$ at −78° C. was added n-BuLi (1.48 mL, 3.71 mmol, 2.5 M), followed by dropwise addition of a suspension of Intermediate A-6 (500 mg, 1.06 mmol) in THF (5 mL) to give a light yellow suspension. After stirring at −78° C. for 30 min, a solution of Intermediate 11-2 (362 mg, 3.18 mmol) in THF (2 mL) was added and the reaction was stirred at −78° C. for 10 min and at 15° C. for 16 hrs. The reaction was quenched with aq.NH$_4$Cl (50 mL) and extracted with EtOAc (3×30 mL). The combined organic phases were washed with brine (50 mL), dried over anhydrous sodium sulfate, filtered and concentrated to give crude Intermediate 11-3 (500 mg) as a yellow solid, which was used directly in next step.

LCMS Rt=0.939 min in 1.5 min chromatography, 5-95 AB, purity 79%, MS ESI calcd. for $C_{35}H_{51}O_4S$ [M+H−H$_2$O]$^+$ 567, found 567.

Step 3. Synthesis of Compound 11. To a solution of Intermediate 11-3 (500 mg, 0.85 mmol) in 20 mL of dry MeOH under $N_2$, magnesium turnings (828 mg, 34.1 mmol) (activated with 0.5% aqueous HCl, water, dry ethanol, and MTBE) and NiCl$_2$ (22 mg, 0.17 mmol) were added with stirring at 55° C. to initiate continuous hydrogen generation. After two batches of magnesium turnings (828 mg) were added, most of the starting material was consumed. The reaction mixture was quenched at 10° C. by addition of 2M HCl (40 mL) until the complete dissolution of all solids. The resulting solution was extracted with DCM (3×50 mL) and the combined organic phases were washed with brine (80 mL), dried over Na$_2$SO$_4$, filtered and concentrated. The resulting residue was purified by silica gel chromatography (0%~20% MeOH in DCM) to afford the crude product, which was recrystallized from MeCN (20 mL) to afford Compound 11 (150 mg, 40%) as a white solid.

$^1$H NMR (400 MHz, CDCl$_3$) δ 5.25-5.22 (m, 1H), 3.84-3.75 (m, 1H), 3.50-3.40 (m, 1H), 3.36-3.21 (m, 2H), 2.39-2.32 (m, 1H), 2.19-2.14 (m, 1H), 1.96-1.86 (m, 3H), 1.85-1.51 (m, 6H), 1.49-1.40 (m, 3H), 1.44-1.26 (m, 8H), 1.25-1.14 (m, 2H), 1.13-0.97 (m, 8H), 0.96-0.82 (m, 8H), 0.61 (s, 3H).

LCMS Rt=1.226 min in 2 min chromatography, 30-90AB_E, purity 100%, MS ESI calcd. for $C_{29}H_{45}O$ [M+H−2H$_2$O]$^+$ 409, found 409.

Example 16. Synthesis of Compound 12

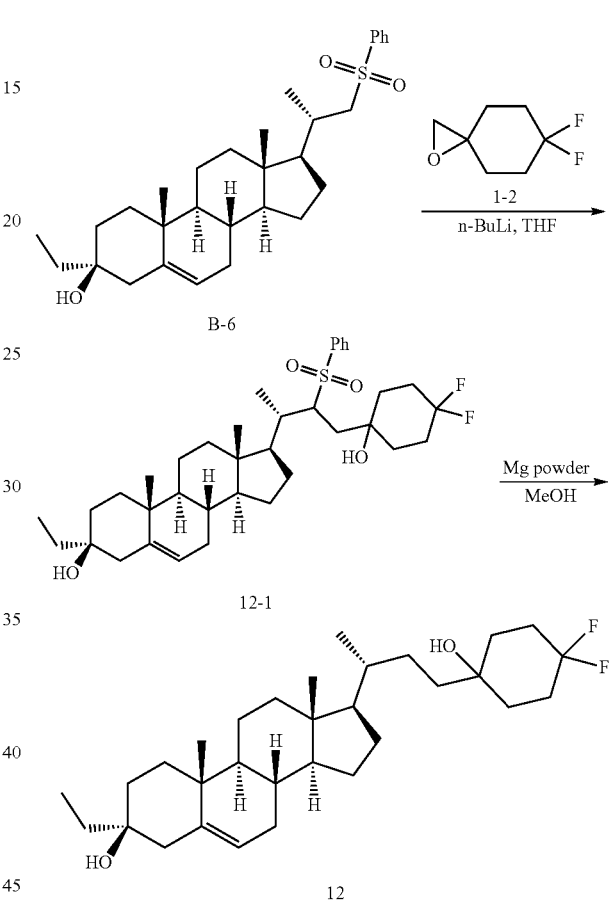

Step 1. Synthesis of Intermediate 12-1. To a flask containing THF (5 mL) was added BuLi (4.12 mL, 2.5 M in hexane, 10.3 mmol) and the solution was cooled to −70° C. and treated with a solution of Intermediate B-4 (2 g, 4.12 mmol) in THF (10 mL). The mixture was stirred at −70° C. for 1 h and treated with a solution of Intermediate 1-2 (1.89 g, 6.18 mmol, 50% purity) in THF (5 mL) at −70° C. The reaction was warmed to 25° C. and allowed to stir for 16 hrs. NH$_4$Cl (40 mL, saturated aq.) was added and the mixture was extracted with EtOAc (30 mL). The organic layer was separated, dried over Na$_2$SO$_4$, filtered, and concentrated. The crude residue was purified by silica gel chromatography (0-25% EtOAc in PE) to give Intermediate 12-1 (150 mg, 6%) as an off-white solid.

$^1$H NMR (400 MHz, CDCl$_3$) δ 7.96-7.90 (m, 2H), 7.70-7.62 (m, 1H), 7.62-7.55 (m, 2H), 5.30-5.26 (m, 1H), 3.58 (m, 1H), 2.40-2.28 (m, 3H), 2.10-2.00 (m, 2H), 1.99-1.76 (m, 6H), 1.75-1.58 (m, 7H), 1.56-1.31 (m, 8H), 1.30-1.15 (m, 4H), 1.14-1.03 (m, 3H), 1.01 (s, 3H), 0.96-0.75 (m, 8H), 0.58 (s, 3H).

Step 2. Synthesis of Compound 12. To a solution of Intermediate 12-1 (170 mg, 0.268 mmol) in MeOH (15 mL) was added Mg powder (256 mg, 10.7 mmol) at 55° C. After stirring at 60° C. for 16 hrs., the reaction was quenched by addition of HCl (50 mL, 1 N) until the reaction became clear and the resulting solution was extracted with DCM (2×30 mL). The combined organic phases were dried over $Na_2SO_4$, filtered, concentrated and purified by silica gel chromatography (0-10% EtOAc in PE) to give Compound 12 (50 mg, 38%) as an off-white solid.

$^1$H NMR (400 MHz, $CDCl_3$) δ 5.30-5.26 (m, 1H), 2.38-2.31 (m, 1H), 2.18-1.76 (m, 8H), 1.75-1.58 (m, 8H), 1.56-1.41 (m, 9H), 1.40-1.20 (m, 3H), 1.18-1.05 (m, 5H), 1.02 (s, 3H), 1.00-0.90 (m, 6H), 0.88-0.80 (m, 3H), 0.68 (s, 3H).

LCMS Rt=1.268 min in 2.0 min chromatography, 30-90 AB, purity 100%, MS ESI calcd. for $C_{31}H_{47}F_2[M+H-2H_2O]^+$ 457, found 457.

Example 17. Synthesis of Compound 13

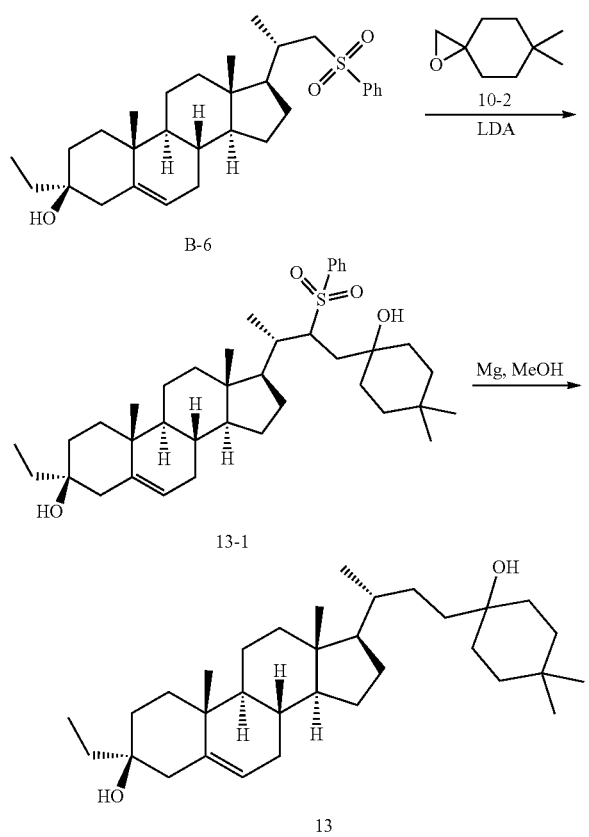

Step 1. Synthesis of Intermediate 13-1. To a solution of diisopropylamine (526 mg, 5.20 mmol) in THF (1 mL) was added n-BuLi (1.93 mL, 2.5 M in hexane, 4.84 mmol) under $N_2$ at −70° C. and the mixture was allowed to warm to 25° C. After cooling to −70° C., a suspension of Intermediate B-4 (588 mg, 1.21 mmol) in THF (5 mL) was added dropwise under $N_2$ and stirring was continued at −70° C. for 30 min. Intermediate 10-2 (339 mg, 2.42 mmol) was added at −70° C. and the reaction was allowed to slowly warm to 25° C. After stirring for 16 hours, the reaction was quenched with saturated aqueous $NH_4Cl$ (15 mL) and the resulting mixture was extracted with EtOAc (2×15 mL). The combined organic phases were washed with brine (2×20 mL), dried over $Na_2SO_4$, filtered and concentrated in vacuo to give Intermediate 13-1 (840 mg, crude) as a yellow oil which was used directly for next step without further purification.

Step 2. Synthesis of Compound 13. A solution of Intermediate 13-1 (840 mg, 1.34 mmol) in MeOH (40 mL) was heated to 65° C. $NiCl_2$ (34.2 mg, 268 μmol) and Mg powder (1.28 g, 53.6 mmol) were added in one portion and the mixture was allowed to stir at 65° C. for 1 h. After cooling, the mixture was quenched by addition of HCl (40 mL, 2N) until the reaction became clear and the resulting solution was extracted with DCM (2×40 mL). The combined organic layers were dried over $Na_2SO_4$, filtered, concentrated and purified by silica gel chromatography (0-10% EtOAc in PE) to give Compound 13 (240 mg, 37%) as an off-white solid.

$^1$H NMR (400 MHz, $CDCl_3$) δ 5.31-5.26 (m, 1H), 2.42-2.31 (m, 1H), 2.07-1.92 (m, 3H), 1.92-1.78 (m, 1H), 1.77-1.68 (m, 1H), 1.68-1.58 (m, 3H), 1.52-1.44 (m, 10H), 1.44-1.34 (m, 4H), 1.34-1.23 (m, 3H), 1.22-1.14 (m, 3H), 1.14-1.05 (m, 5H), 1.04-0.96 (m, 5H), 0.96-0.89 (m, 7H), 0.89-0.82 (m, 6H), 0.68 (s, 3H).

LCMS Rt=1.475 min in 2 min chromatography, 30-90AB, purity 100%, MS ESI calcd. For $C_{33}H_{53} [M+H-2H_2O]^+$ 449, found 449.

Example 18. Synthesis of Compound 14

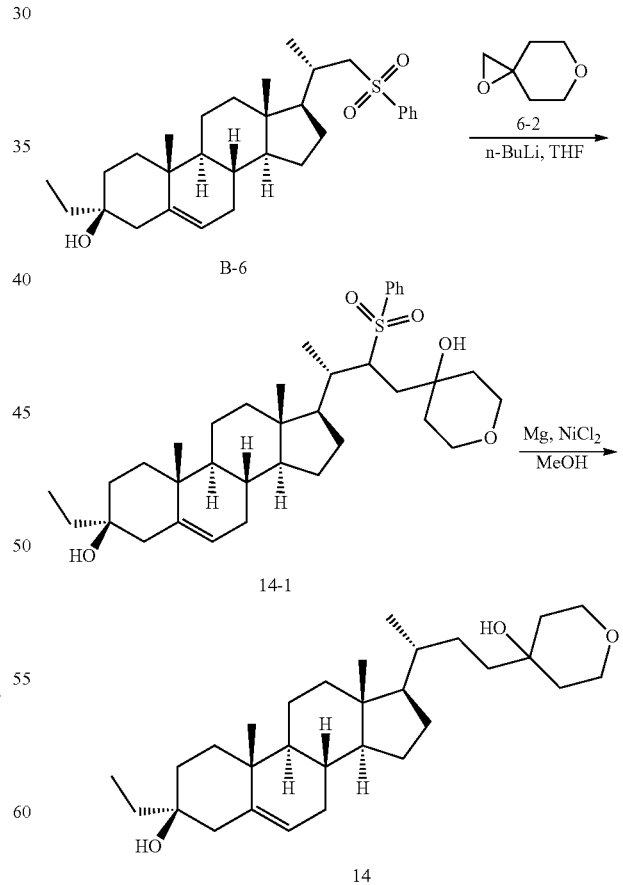

Step 1. Synthesis of Intermediate 14-1. To a flask containing THF (3 mL) under $N_2$ at −78° C. was added n-BuLi (1.44 mL, 3.60 mmol, 2.5 M), followed by dropwise addition of a suspension of Intermediate B-4 (500 mg, 1.03 mmol) in THF (5 mL) to give a light yellow suspension. After stirring at −78° C. for 30 min, a solution of Intermediate 6-2 (352 mg, 3.09 mmol) in THF (2 mL) was added, and the reaction was stirred at −78° C. for 10 min at 15° C. for 16 hours. The reaction was quenched with saturated NH$_4$Cl (50 mL) and extracted with DCM (3×50 mL). The combined organic phases were washed with brine (100 mL), dried over anhydrous sodium sulfate, filtered and concentrated to give crude Intermediate 14-1 (500 mg) as a yellow solid, which was used directly in next step.

LCMS Rt=0.953 min in 1.5 min chromatography, 5-95 AB, purity 36%, MS ESI calcd. for C$_{36}$H$_{54}$O$_5$SNa [M+Na]$^+$ 621, found 621.

Step 2. Synthesis of Compound 14. To a solution of Intermediate 14-1 (500 mg, 0.834 mmol) in 20 mL of anhydrous MeOH under N$_2$, magnesium turnings (809 mg, 33.3 mmol) (activated with 0.5% aqueous HCl, water, anhydrous EtOH, and MTBE) and NiCl$_2$ (21.5 mg, 0.17 mmol) were added with stirring at 55° C. to initiate continuous hydrogen generation. After two batches of 809 mg of magnesium turnings were added, most of the starting material was consumed. The reaction mixture was quenched at 10° C. by addition of 2M HCl (40 mL) until the complete dissolution of all solids and the resulting solution was extracted with DCM (3×50 mL). The combined organic phases were washed with brine (80 mL), dried over Na$_2$SO$_4$, filtered and concentrated. The resulting residue was purified by silica gel chromatography (0%~20% MeOH in DCM), to afford the crude product, which was recrystallized from MeCN (20 mL) to afford Compound 14 (150 mg, 39%) as an off-white solid.

$^1$H NMR (400 MHz, CDCl$_3$) δ 5.26-5.18 (m, 1H), 3.78-3.61 (m, 4H), 2.34-2.25 (m, 1H), 2.02-1.85 (m, 4H), 1.83-1.71 (m, 1H), 1.69-1.49 (m, 7H), 1.47-1.35 (m, 9H), 1.27-1.15 (m, 4H), 1.12-0.96 (m, 9H), 0.90-0.77 (m, 7H), 0.61 (s, 3H).

LCMS Rt=1.227 min in 2.0 min chromatography, 30-90 AB, purity 100%, MS ESI calcd. for C$_{30}$H$_{47}$O [M+H−2H$_2$O]$^+$ 423, found 423.

Example 19. Synthesis of Compound 15

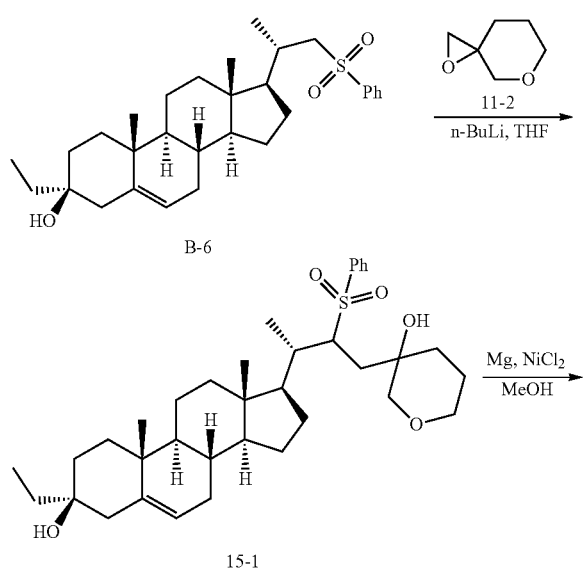

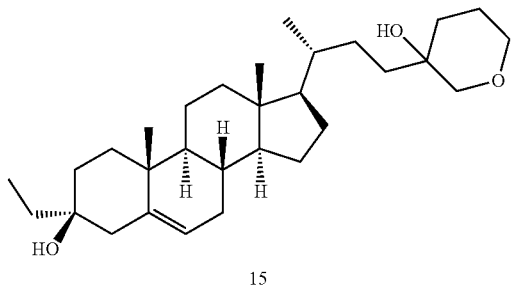

Step 1. Synthesis of Intermediate 15-1. To a flask containing THF (3 mL) under N$_2$ at −78° C. was added n-BuLi (1.44 mL, 3.60 mmol, 2.5 M), followed by dropwise addition of a suspension of Intermediate B-4 (500 mg, 1.03 mmol) in THF (5 mL) to give a light yellow suspension. After stirring at −78° C. for 30 min, a solution of Intermediate 11-2 (352 mg, 3.09 mmol) in THF (2 mL) was added. The reaction was stirred at −78° C. for 10 mins and at 15° C. for 16 hrs. The reaction was quenched with aq.NH$_4$Cl (50 mL) and extracted with DCM (3×50 mL). The combined organic phases were washed with brine (100 mL), dried over anhydrous sodium sulfate, filtered and concentrated to give crude Intermediate 15-1 (500 mg) as a yellow solid, which was used directly in next step.

LCMS Rt=0.973 min in 1.5 min chromatography, 5-95 AB, purity 47%, MS ESI calcd. for C$_{36}$H$_{53}$O$_4$S [M+H−H$_2$O]$^+$ 581, found 581.

Step 2. Synthesis of Compound 15. To a solution of Intermediate 15-1 (500 mg, 0.834 mmol) in 20 mL of dry MeOH under N$_2$, magnesium turnings (809 mg, 33.3 mmol) (activated with 0.5% aqueous HCl, water, dry ethanol, and MTBE) and NiCl$_2$ (21.5 mg, 0.17 mmol) were added with stirring at 55° C. to initiate continuous hydrogen generation. After two batches of magnesium turnings (809 mg) were added, most of the starting material was consumed. The reaction mixture was quenched at 10° C. by addition of 2M HCl (40 mL) until the complete dissolution of all solids. The resulting solution was extracted with DCM (3×50 mL) and the combined organic phases were washed with brine (80 mL), dried over Na$_2$SO$_4$, filtered and concentrated. The resulting residue was purified by silica gel chromatography (0%~20% MeOH in DCM) to provide the product which was recrystallized from MeCN (20 mL) to afford Compound 15 (150 mg, 39%) as an off-white solid.

$^1$H NMR (400 MHz, CDCl$_3$) δ 5.25-5.18 (m, 1H), 3.84-3.74 (m, 1H), 3.50-3.41 (m, 1H), 3.35-3.21 (m, 2H), 2.33-2.26 (m, 1H), 2.20-2.12 (m, 1H), 2.00-1.64 (m, 7H), 1.63-1.47 (m, 6H), 1.44-1.31 (m, 9H), 1.26-1.14 (m, 3H), 1.10-0.94 (m, 8H), 0.89-0.75 (m, 7H), 0.61 (s, 3H).

LCMS Rt=1.284 min in 2.0 min chromatography, 30-90 AB, purity 100%, MS ESI calcd. for C$_{30}$H$_{47}$O [M+H−2H$_2$O]$^+$ 423, found 423.

Example 20. Synthesis of Compound 16

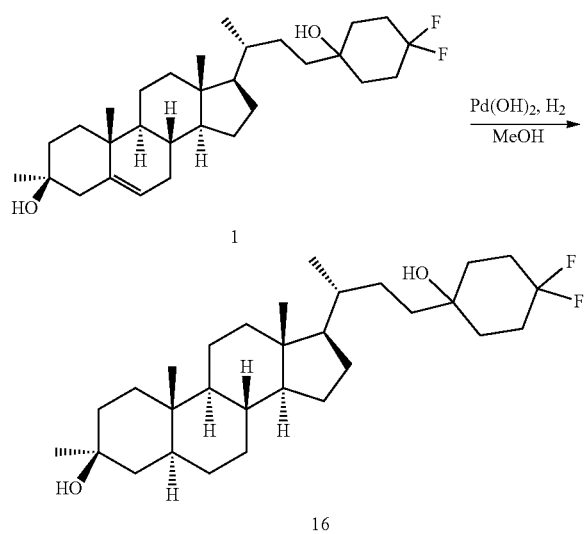

To a solution of Compound 1 (300 mg, 0.626 mmol) in MeOH (20 mL) was added Pd(OH)$_2$ (100 mg, dry). The mixture was hydrogenated at 50° C., 50 Psi for 48 hrs. The mixture was filtered, washed with DCM (100 mL) and the filtrate was concentrated. The resulting residue was purified by silica gel chromatography (0-15% EtOAc in PE) to give Compound 16 (114 mg, 38%) as an off-white solid.

$^1$H NMR (400 MHz, CDCl$_3$) δ 2.20-2.00 (m, 2H), 1.99-1.75 (m, 4H), 1.70-1.60 (m, 5H), 1.59-1.42 (m, 8H), 1.41-1.23 (m, 6H), 1.22-1.16 (m, 6H), 1.15-0.96 (m, 8H), 0.95-0.82 (m, 4H), 0.80 (s, 3H), 0.70-0.60 (m, 4H).

LCMS Rt=1.275 min in 2.0 min chromatography, 30-90 AB, purity 100%, MS ESI calcd. for C$_{30}$H$_{47}$F$_2$[M+H−2H$_2$O]$^+$ 445, found 445.

Example 21. Synthesis of Compound 17

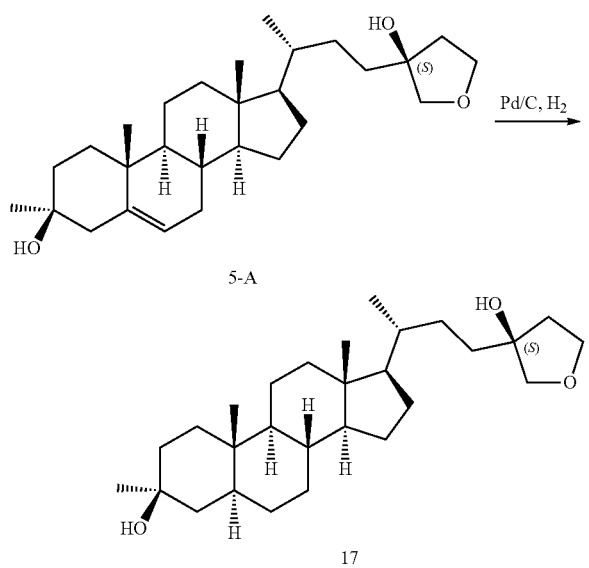

To a solution of Compound 5-A (100 mg, 0.232 mmol) in MeOH (10 mL) was added dry Pd/C (100 mg) at 15° C. The mixture was degassed and purged several times with H$_2$ and was allowed to stir under 50 psi H$_2$ at 55° C. for 48 hrs. The reaction mixture was filtered to remove the Pd/C and the filtrate was concentrated. The resulting residue was purified by silica gel chromatography (0%~30%) EtOAc in PE/DCM (v/v=1/1)) to afford Compound 17 (30 mg, 30%) as an off-white solid.

$^1$H NMR (400 MHz, CDCl$_3$) δ 4.06-3.98 (m, 1H), 3.93-3.85 (m, 1H), 3.69 (d, J=9.2 Hz, 1H), 3.54 (d, J=9.2 Hz, 1H), 1.99-1.75 (m, 4H), 1.74-1.58 (m, 5H), 1.55-1.37 (m, 7H), 1.35-1.18 (m, 10H), 1.17-0.95 (m, 7H), 0.94-0.83 (m, 4H), 0.80 (s, 3H), 0.70-0.60 (m, 4H).

LCMS Rt=1.114 min in 2.0 min chromatography, 30-90 AB, purity 100%, MS ESI calcd. for C$_{28}$H$_{45}$O [M+H−2H$_2$O]$^+$ 397, found 397.

Example 22. Synthesis of Compound 18

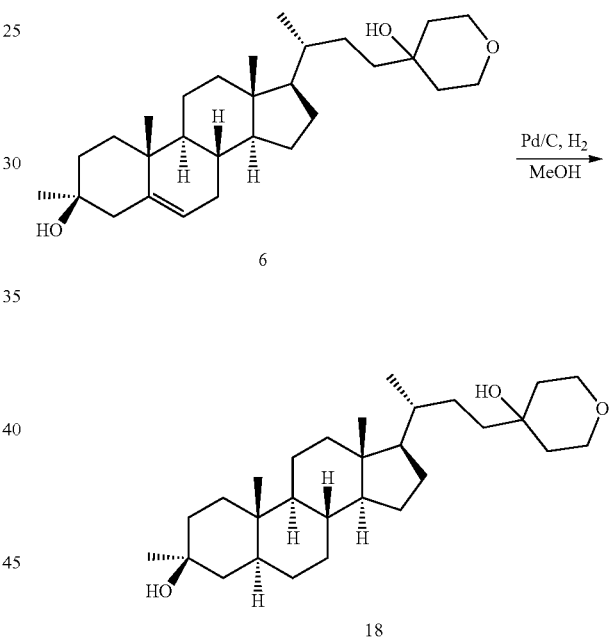

To a solution of Compound 6 (100 mg, 0.224 mmol) in MeOH (10 mL) was added dry Pd/C (100 mg) at 15° C. The mixture was degassed and purged several times with H$_2$ and was allowed to stir under 50 psi H$_2$ at 50° C. for 48 hrs. The reaction mixture was filtered to remove the Pd/C and the filtrate was concentrated. The resulting residue was purified by silica gel chromatography (0%~30% EtOAc in PE/DCM (v/v=1/1)) to afford Compound 18 (32 mg, 32.0%) as an off-white solid.

$^1$H NMR (400 MHz, CDCl$_3$) δ 3.75-3.61 (m, 4H), 1.92-1.84 (m, 1H), 1.81-1.70 (m, 1H), 1.66-1.49 (m, 7H), 1.48-1.36 (m, 7H), 1.34-1.22 (m, 5H), 1.20-1.12 (m, 7H), 1.09-0.98 (m, 5H), 0.96-0.77 (m, 6H), 0.81 (s, 3H), 0.64-0.53 (m, 4H).

LCMS Rt=1.216 min in 2.0 min chromatography, 30-90 AB, purity 100%, MS ESI calcd. for C$_{29}$H$_{47}$O [M+H−2H$_2$O]$^+$ 411, found 411.

Example 23. Synthesis of Compound 19

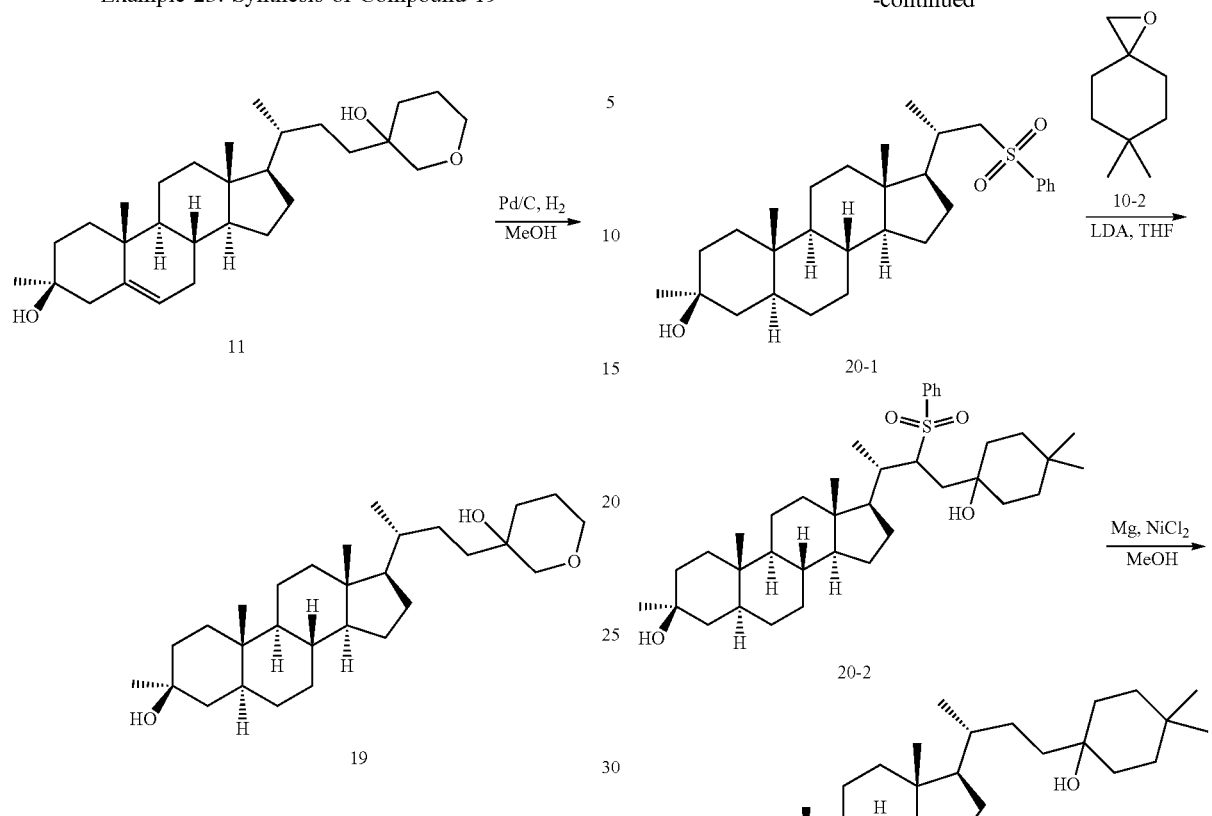

To a solution of Compound 11 (100 mg, 0.224 mmol) in MeOH (10 mL) was added dry Pd/C (100 mg) at 15° C. The mixture was degassed and purged several times with H₂ and was allowed to stir under 50 psi H₂ at 50° C. for 48 hrs. The reaction mixture was filtered to remove the Pd/C and the filtrate was concentrated. The resulting residue was purified by silica gel chromatography (0%~30% EtOAc in PE/DCM (v/v=1/1)) to afford Compound 19 (35.0 mg, 35%) as an off-white solid.

$^1$H NMR (400 MHz, CDCl$_3$) δ 3.84-3.74 (m, 1H), 3.49-3.42 (m, 1H), 3.35-3.20 (m, 2H), 2.18-2.14 (m, 1H), 1.93-1.71 (m, 3H), 1.68-1.49 (m, 5H), 1.47-1.34 (m, 7H), 1.33-1.21 (m, 4H), 1.21-1.10 (m, 8H), 1.10-0.89 (m, 7H), 0.88-0.68 (m, 7H), 0.63-0.52 (m, 4H).

LCMS Rt=1.249 min in 2 min chromatography, 30-90AB_E, purity 100%, MS ESI calcd. for C$_{29}$H$_{47}$O [M+H−2H$_2$O]$^+$411, found 411.

Example 24. Synthesis of Compound 20

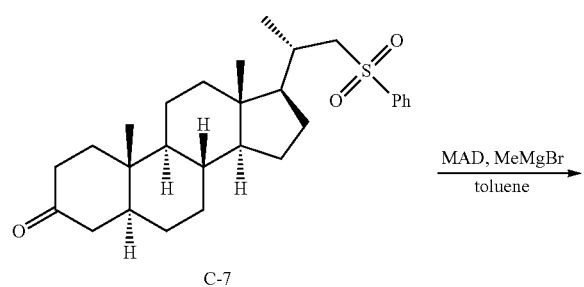

Step 1. Synthesis of Intermediate 20-1. To a solution of 2,6-di-tert-butyl-4-methylphenol (14.4 mg, 65.4 mmol) in toluene (100 mL) was added AlMe3 (16.3 mL, 32.7 mmol, 2 M in toluene) dropwise at 0° C. The mixture was stirred at 25° C. for 1 h to give a MAD solution. A solution of Intermediate C-7 (5 g, 10.9 mmol) in toluene (50 mL) was added dropwise to the MAD (116 ml, 0.28 M in toluene) reaction mixture at −65° C. After stirring at −65° C. for 1 h, MeMgBr (10.8 mL, 32.6 mmol, 3M in ethyl ether) was added dropwise at −65° C. and the resulting solution was stirred at −65° C. for 1 hr. The reaction was quenched at −65° C. with saturated aqueous NH$_4$Cl (100 mL) and the mixture was allowed to warm to 25° C. After stirring for 10 min, the resulting suspension was filtered through a Celite pad and the pad was washed with EtOAc (100 mL). The combined organic layers were separated, washed with brine (50 mL), dried over Na$_2$SO$_4$, filtered and concentrated in vacuo to afford Intermediate 20-1 (4.5 g crude) as an off-white solid.

$^1$H NMR (400 MHz, CDCl$_3$) δ 7.95-7.83 (m, 2H), 7.66-7.60 (m, 1H), 7.58-7.51 (m, 2H), 3.17-3.08 (m, 1H), 2.88-2.68 (m, 1H), 2.15-2.03 (m, 1H), 1.94-1.86 (m, 1H), 1.73-1.40 (m, 9H), 1.40-0.90 (m, 19H), 0.90-0.80 (m, 1H), 0.79 (s, 3H), 0.62 (s, 3H).

Step 2. Synthesis of Intermediate 20-2. To a solution of n-BuLi (504 μL, 2.5 M in hexane, 1.26 mmol) in THF (1 mL) at −65° C. under N$_2$, a suspension of Intermediate 20-1

(200 mg, 0.423 mmol) in THF (3 mL) was added dropwise. After stirring for 30 minutes at −65° C., a solution of diisopropylamine (127 mg, 1.26 mmol) was added dropwise, followed by the dropwise addition of a solution of Intermediate 10-2 (176 mg, 1.26 mmol). The mixture was stirred for another 30 min at −65° C. and then gradually warmed to 25° C. and allowed to stir for 16 hours. The reaction was quenched with saturated aqueous $NH_4Cl$ (10 mL) and extracted with EtOAc (3×10 mL). The combined organic layers were dried over $Na_2SO_4$, filtered and concentrated to give Intermediate 20-2 (270 mg, crude), which was used directly for the next step.

Step 3. Synthesis of Compound 20. A solution of Intermediate 20-2 (270 mg, 0.44 mmol) in MeOH (50 mL) was heated to 60° C. One portion of $NiCl_2$ (2.83 mg, 0.022 mmol) was added, followed by four portions of Mg (420 mg, 17.5 mmol). After stirring at 60° C. for 1 h, the reaction was quenched by addition of HCl (10 mL, 2 M) until a clear solution was obtained and the solution was extracted with DCM (2×20 mL). The combined organic phases were dried over $Na_2SO_4$, filtered, concentrated and purified by silica gel chromatography (0-20% EtOAc in PE) to give Compound 20 (100 mg, 48%). The product was dissolved in MeCN (25 mL), vacuum concentrated at 70° C., triturated with water (5 mL), filtered and concentrated to give Compound 20 as an off-white solid (56 mg).

$^1$H NMR (400 MHz, $CDCl_3$) δ 2.00-1.91 (m, 1H), 1.89-1.78 (m, 1H), 1.70-1.51 (m, 3H), 1.51-1.19 (m, 13H), 1.19-1.04 (m, 13H), 1.18-1.06 (m, 5H), 1.06-0.96 (m, 3H), 0.95-0.86 (m, 10H), 0.82-0.79 (m, 3H), 0.70-0.60 (m, 4H).

LCMS Rt=1.442 min in 2 min chromatography, 30-90AB_2MIN_E, purity 100%, MS ESI calcd. for $C_{32}H_{53}$ $[M+H-2H_2O]^+$ 437, found 437.

Example 25. Synthesis of Compound 21

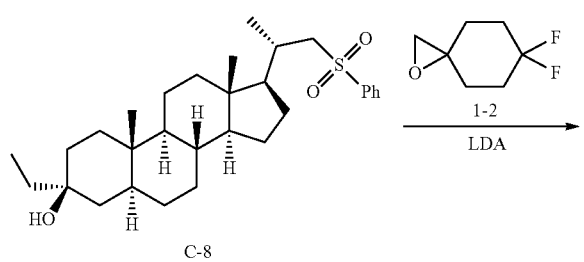

C-8

Step 1. Synthesis of Intermediate 21-1. To a solution of diisopropylamine (173 mg, 1.72 mmol) in THF (0.5 mL) cooled to −70° C. was added butyllithium (0.616 mL, 1.54 mmol, 2.5 M in n-hexane) and the mixture was stirred at −70° C. for 30 minutes. A solution of Intermediate C-8 (300 mg, 0.616 mmol) in THF (3 mL) was added and the mixture was stirred at −70° C. for 30 minutes. Intermediate 1-2 (182 mg, 1.23 mmol) was added at −70° C. and the mixture was warmed to 25° C. and stirred at this temperature for 17 hours. The mixture was quenched with saturated $NH_4Cl$ (30 mL), extracted with EtOAc (3×10 mL), washed with brine (2×30 mL), dried over $Na_2SO_4$, filtered and concentrated in vacuo to give Intermediate 21-1 (350 mg) as a yellow solid, which was used directly in the next step.

Step 2. Synthesis of Compound 21. A solution of Intermediate 21-1 (350 mg, 0.551 mmol) in MeOH (15 mL) was heated to 55° C., treated with one portion of Mg powder (547 mg, 22.8 mmol) and heated to reflux for 1 h. The reaction was quenched with HCl (50 mL, 1N) and the resulting clear solution was extracted with DCM (2×30 mL). The combined organic phases were dried over $Na_2SO_4$, filtered, concentrated and purified by silica gel chromatography (0-10% EtOAc in PE) to give impure Compound 21 (120 mg, 44% yield, containing 22,23-olefin) as an off-white solid. The 120 mg of impure sample was dissolved in THF (5 mL) and treated with Pd/C (100 mg, wet). The mixture was hydrogenated (15Psi, 25° C.) for 2 hrs, filtered, concentrated and purified by silica gel chromatography (0-15% EtOAc in PE) to give Compound 21 (86 mg, 72%) as an off-white solid.

$^1$H NMR (400 MHz, $CDCl_3$) δ 2.20-2.01 (m, 2H), 1.98-1.72 (m, 4H), 1.70-1.58 (m, 10H), 1.56-1.41 (m, 6H), 1.40-1.30 (m, 5H), 1.29-1.18 (m, 4H), 1.17-1.05 (m, 4H), 1.04-0.96 (m, 3H), 0.95-0.80 (m, 10H), 0.68-0.58 (m, 4H).

LCMS Rt=1.325 min in 2.0 min chromatography, 30-90 AB, purity 100%, MS ESI calcd. for $C_{31}H_{49}F_2[M+H-2H_2O]^1$ 459, found 459.

Example 26. Synthesis of Compound 22

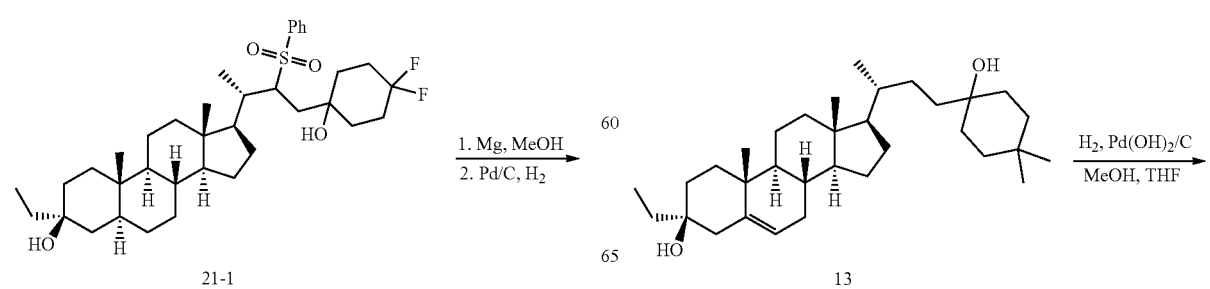

-continued

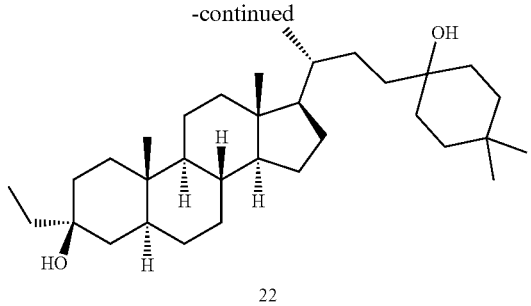

22

To a solution of Compound 13 (160 mg, 0.391 mmol) in MeOH (15 mL) and THF (15 mL) was added Pd(OH)$_2$/C (dry, 350 mg) under N$_2$. The suspension was degassed and purged with H$_2$ three times. The mixture was stirred under H$_2$ (50 psi) at 50° C. for 48 hours to give a black suspension. The reaction mixture was filtered through a pad of Celite, washed with THF (3×20 mL) and the filtrate was concentrated in vacuo to give Compound 22 (12 mg, 8%) as an off-white solid.

$^1$H NMR (400 MHz, CDCl$_3$) δ 2.00-1.91 (m, 1H), 1.91-1.73 (m, 1H), 1.69-1.56 (m, 5H), 1.54-1.44 (m, 9H), 1.44-1.41 (m, 1H), 1.41-1.32 (m, 4H), 1.32-1.15 (m, 9H), 1.15-1.04 (m, 5H), 1.04-0.95 (m, 3H), 0.95-0.91 (m, 5H), 0.91-0.89 (m, 2H), 0.89-0.85 (m, 6H), 0.85-0.79 (m, 3H), 0.69-0.60 (m, 4H)

LCMS Rt=1.515 min in 2 min chromatography, 30-90AB, purity 100%, MS ESI calcd. For C$_{33}$H$_{55}$ [M+H−2H$_2$O]$^+$ 451, found 451.

Example 27. Synthesis of Compound 23

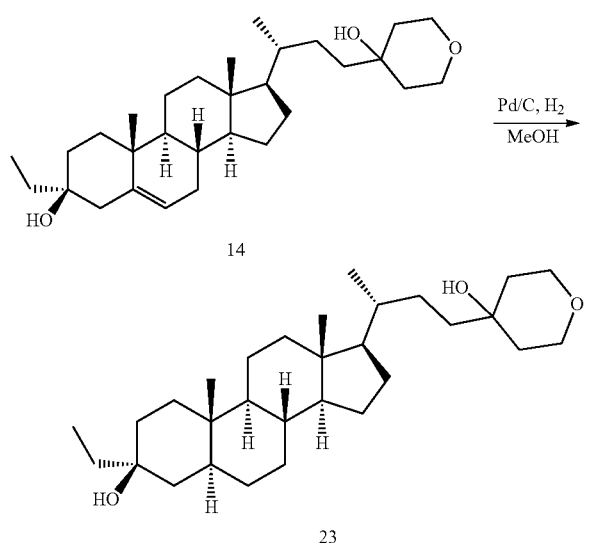

To a solution of Compound 14 (100 mg, 0.217 mmol) in MeOH (10 mL) was added dry Pd/C (100 mg) at 15° C. The mixture was degassed and purged with H$_2$ several times and was stirred under 50 psi H$_2$ at 55° C. for 48 hrs. The reaction mixture was filtered to remove the Pd/C, the filtrate was concentrated and the residue was purified by silica gel chromatography (0%~30% EtOAc in PE/DCM (v/v=1/1)) to afford Compound 23 (36.0 mg, 36%) as an off-white solid.

$^1$H NMR (400 MHz, CDCl$_3$) δ 3.82-3.69 (m, 4H), 1.99-1.91 (m, 1H), 1.87-1.75 (m, 1H), 1.73-1.57 (m, 7H), 1.55-1.42 (m, 7H), 1.40-1.17 (m, 10H), 1.16-0.95 (m, 8H), 0.94-0.84 (m, 7H), 0.82 (s, 3H), 0.70-0.55 (m, 4H).

LCMS Rt=1.208 min in 2.0 min chromatography, 30-90 AB, purity 100%, MS ESI calcd. for C$_{30}$H$_{49}$O [M+H−2H$_2$O]$^+$ 425, found 425.

Example 28. Synthesis of Compound 24

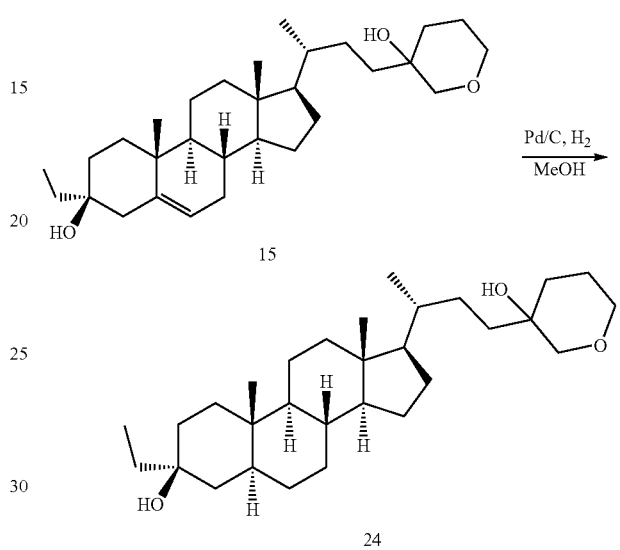

To a solution of Compound 15 (100 mg, 0.217 mmol) in MeOH (10 mL) was added dry Pd/C (100 mg) at 15° C. The mixture was degassed and purged with H$_2$ several times and stirred under 50 psi H$_2$ at 50° C. for 48 hours. The reaction mixture was filtered to remove the Pd/C, the filtrate was concentrated and the residue was purified by silica gel chromatography (0%~30% EtOAc in PE/DCM (v/v=1/1)) to afford Compound 24 (27 mg, 27%) as a white solid.

$^1$H NMR (400 MHz, CDCl$_3$) δ 3.89-3.81 (m, 1H), 3.55-3.48 (m, 1H), 3.43-3.25 (m, 2H), 2.25-2.20 (m, 1H), 1.99-1.77 (m, 3H), 1.73-1.57 (m, 6H), 1.54-1.41 (m, 7H), 1.40-1.18 (m, 10H), 1.15-0.96 (m, 7H), 0.93-0.80 (m, 10H), 0.70-0.57 (m, 4H).

LCMS Rt=1.270 min in 2.0 min chromatography, 30-90 AB, purity 100%, MS ESI calcd. for C$_{30}$H$_{49}$O [M+H−2H$_2$O]$^+$ 425, found 425.

TABLE 1

| | NMDA Potentiation |
|---|---|
| Compound | GluN2A PCA IWB Ephys % potentiation at 3 µM |
| 1 | C |
| 2 | C |
| 3 | C |
| 4 | B |
| 5 | C |
| 5-A | B |
| 5-B | C |
| 6 | B |
| 7 | B |
| 8 | A |
| 9 | C |

TABLE 1-continued

NMDA Potentiation

| Compound | GluN2A PCA IWB Ephys % potentiation at 3 μM |
|---|---|
| 10 | A |
| 11 | C |
| 12 | C |
| 13 | A |
| 14 | C |
| 15 | C |
| 16 | A |
| 17 | C |
| 18 | C |
| 19 | C |
| 20 | A |
| 21 | C |
| 22 | A |
| 23 | C |
| 24 | C |

For Table 1, "A" indicates 10 to 100%, "B" indicates potentiation of >100% to 150%; and "C" indicates potentiation of >150%.

The data in Table 1 demonstrate the ability of the exemplified compounds to modulate the NMDA receptor as positive allosteric modulators (PAMs).

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I-B):

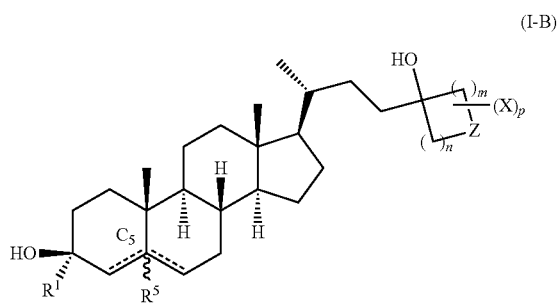

(I-B)

or a pharmaceutically acceptable salt thereof, wherein:
$R^1$ is hydrogen or substituted or unsubstituted $C_{1-6}$ alkyl;
$R^5$ is absent or hydrogen;
Z is —C($R^A$)$_2$—, —$NR^B$—, —O—, or —S—;
X is halogen, substituted or unsubstituted $C_{1-6}$ alkyl, or —$OR^C$;
$R^A$ is hydrogen, halogen, or substituted or unsubstituted $C_{1-6}$ alkyl;
$R^B$ is hydrogen, substituted or unsubstituted $C_{1-6}$ alkyl, —C(O)$R^C$, —C(O)O$R^C$, —C(O)N($R^D$)$_2$, or —S(O)$_2$$R^C$;
$R^C$ is hydrogen or substituted or unsubstituted $C_{1-6}$ alkyl;
each $R^D$ is independently hydrogen, substituted or unsubstituted $C_{1-6}$ alkyl, substituted or unsubstituted aryl, or substituted or unsubstituted heteroaryl;
m is an integer selected from 1, 2, and 3;
n is an integer selected from 1, 2, and 3;
p is an integer selected from 0, 1, 2, 3, 4, and 5; and
═══ represents a single or double bond, wherein when one ═══ is a double bond, then the other ═══ is a single bond and $R^5$ is absent.

2. The compound of claim 1, or a pharmaceutically acceptable salt thereof, wherein the compound is a compound of Formula (II-A), Formula (II-B), or Formula (II-C):

(II-A)
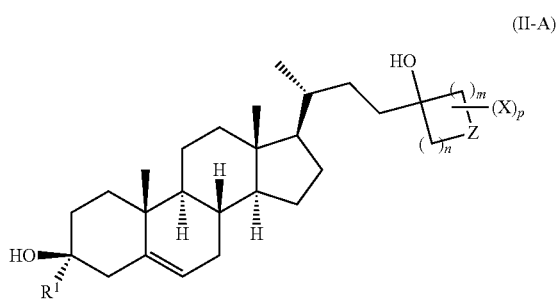

(II-B)
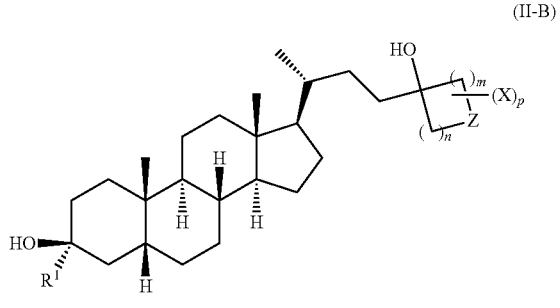

(II-C)
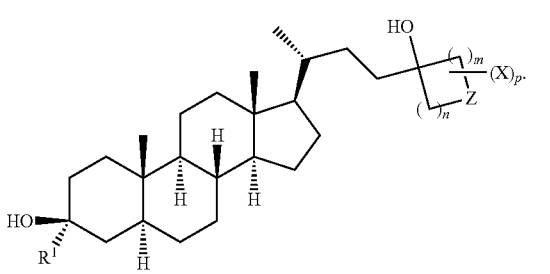

3. The compound of claim 1, or a pharmaceutically acceptable salt thereof, wherein p is an integer selected from 0, 1, or 2.

4. The compound of claim 1, or a pharmaceutically acceptable salt thereof, wherein p is 0.

5. The compound of claim 1, or a pharmaceutically acceptable salt thereof, wherein p is 1.

6. The compound of claim 1, or a pharmaceutically acceptable salt thereof, wherein p is 1 and X is halogen.

7. The compound of claim 2, or a pharmaceutically acceptable salt thereof, wherein the compound is of Formula (II-D), Formula (II-E), or Formula (II-F):

(II-D)
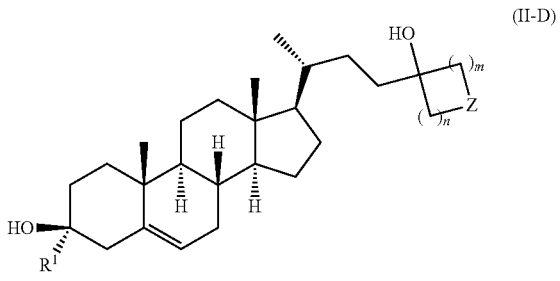

-continued (II-E)
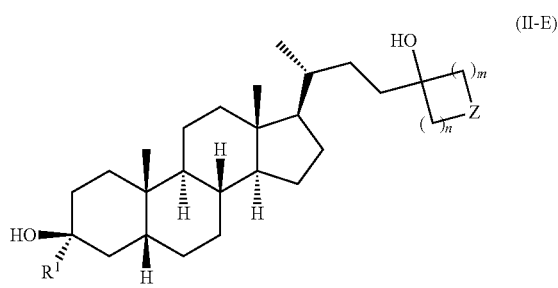

(II-F)
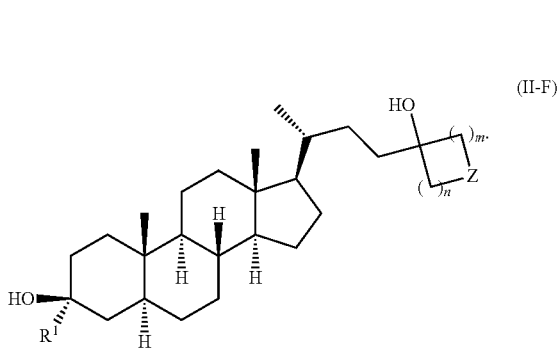

8. The compound of claim 1, or a pharmaceutically acceptable salt thereof, wherein $R^1$ is substituted or unsubstituted $C_{1-6}$ alkyl.

9. The compound of claim 8, or a pharmaceutically acceptable salt thereof, wherein $R^1$ is methyl or ethyl.

10. The compound of claim 1, or a pharmaceutically acceptable salt thereof, wherein the compound is of Formula (II-G) or Formula (II-H):

(II-G)
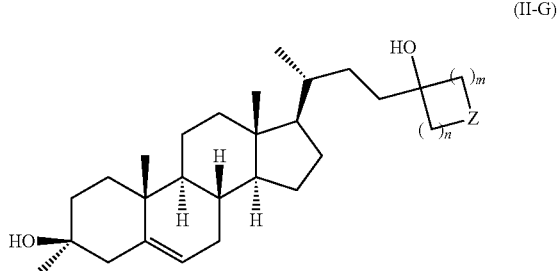

(II-H)
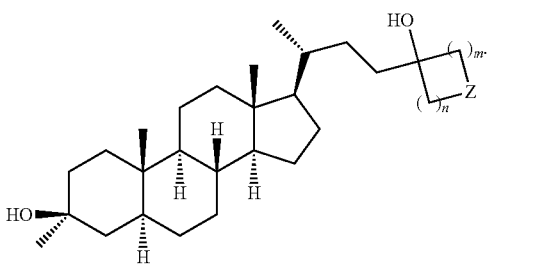

11. The compound of claim 1, or a pharmaceutically acceptable salt thereof, wherein the compound is of Formula (II-I) or Formula (II-J):

12. The compound of claim 1, or a pharmaceutically acceptable salt thereof, wherein Z is —C(R$^A$)$_2$—, —O—, or —NR$^B$—.

13. The compound of claim 1, or a pharmaceutically acceptable salt thereof, wherein R$^A$ is halogen.

14. The compound of claim 1, or a pharmaceutically acceptable salt thereof, wherein Z is —CH$_2$—, —CF$_2$—, or —C(CH$_3$)$_2$—.

15. The compound of claim 1, or a pharmaceutically acceptable salt thereof, wherein Z is —O— or —NR$^B$—.

16. The compound of claim 1, or a pharmaceutically acceptable salt thereof, wherein Z is —NH—, —NCH$_3$—, or —NC(O)CH$_3$—.

17. The compound of claim 1, or a pharmaceutically acceptable salt thereof, wherein Z is —CH$_2$—.

18. The compound of claim 1, or a pharmaceutically acceptable salt thereof, wherein Z is —C(CH$_3$)$_2$—.

19. The compound of claim 1, or a pharmaceutically acceptable salt thereof, wherein Z is —CF$_2$—.

20. The compound of claim 1, or a pharmaceutically acceptable salt thereof, wherein m is 1, n is 2, and Z is —O—.

21. The compound of claim 1, or a pharmaceutically acceptable salt thereof, wherein m is 2 and n is 2.

22. The compound of claim 1, or a pharmaceutically acceptable salt thereof, wherein m is 3 and n is 1.

23. The compound of claim 1, or a pharmaceutically acceptable salt thereof, wherein m is 3, n is 1, and Z is —O—.

24. The compound of claim 1, or a pharmaceutically acceptable salt thereof, wherein m is 2, n is 2, and Z is —O— or —NR$^B$—.

25. A compound selected from:

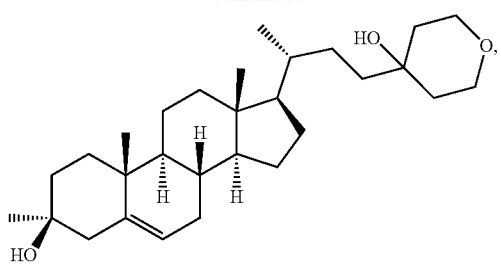
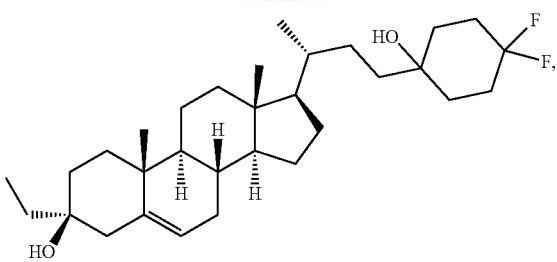
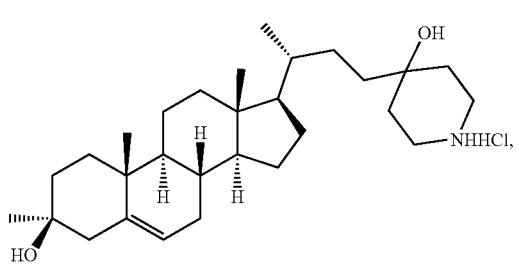
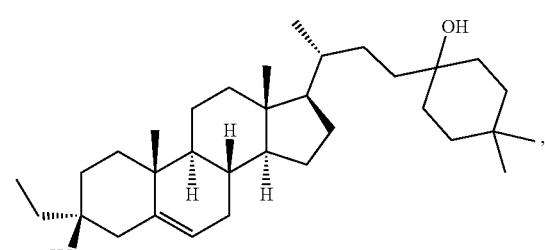
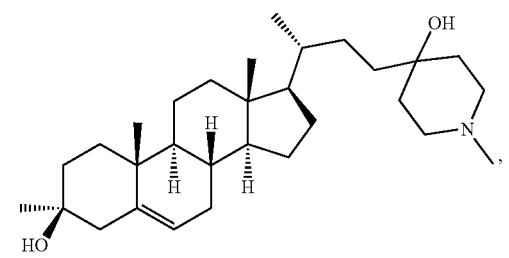
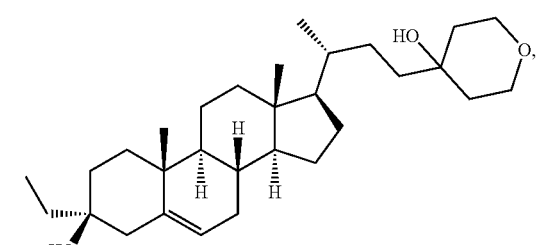
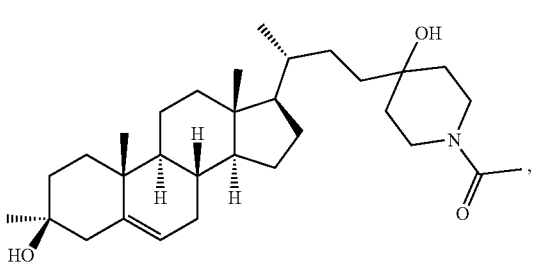
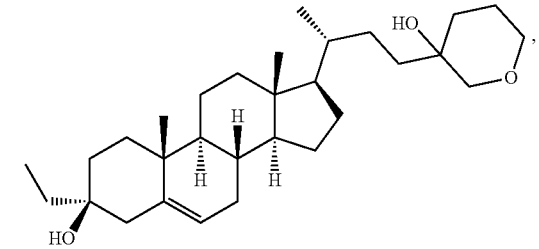
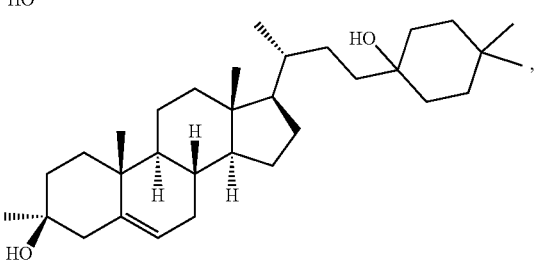
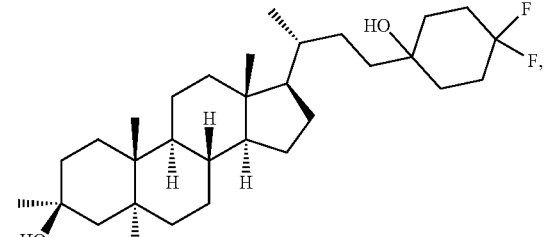
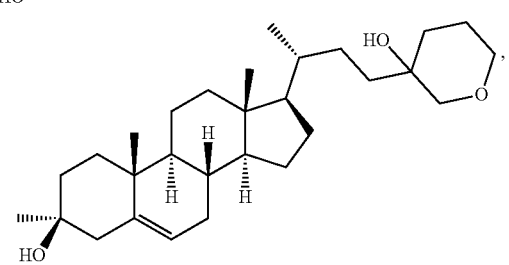
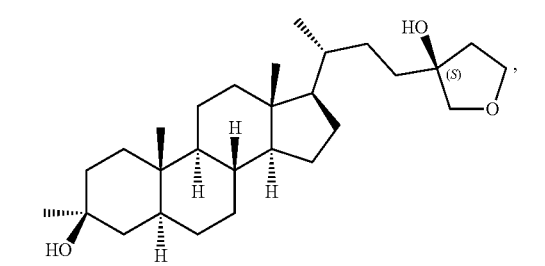

-continued
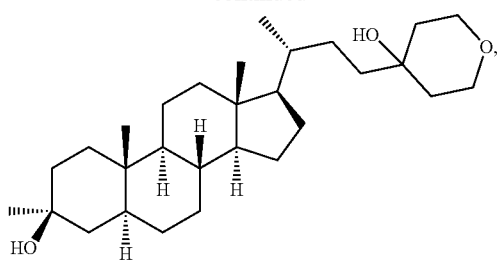
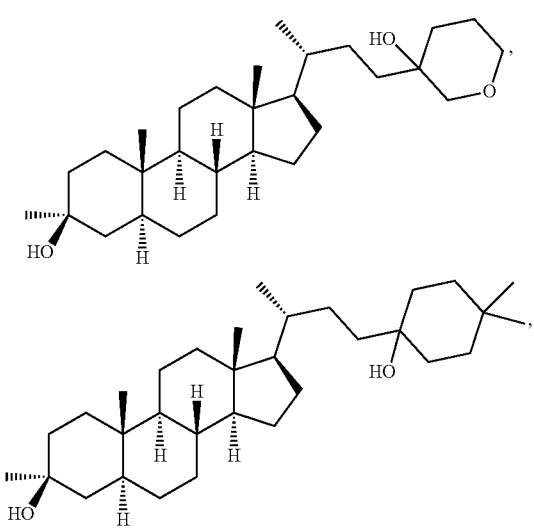
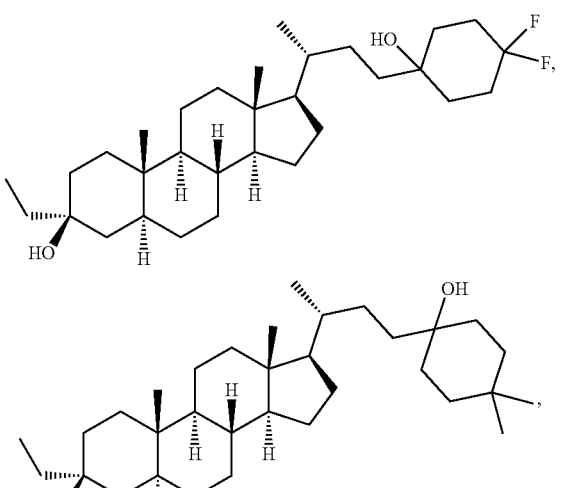
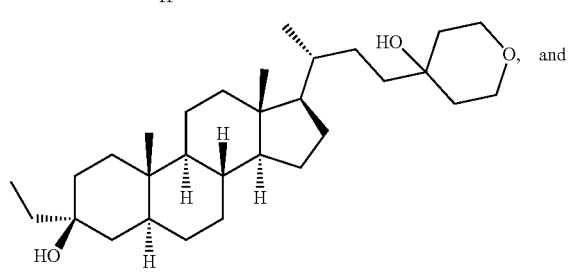
-continued
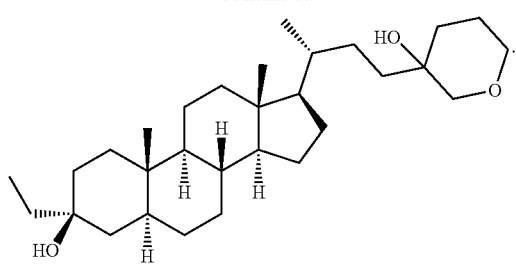
26. A pharmaceutically acceptable salt of a compound selected from:
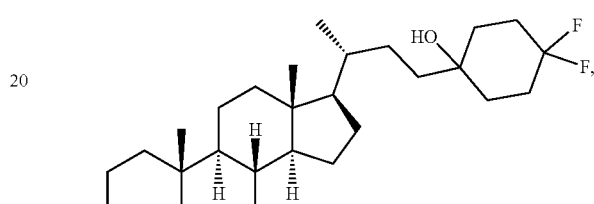
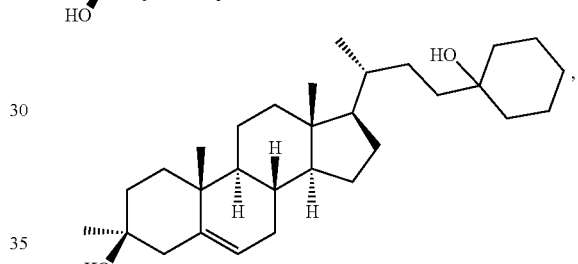
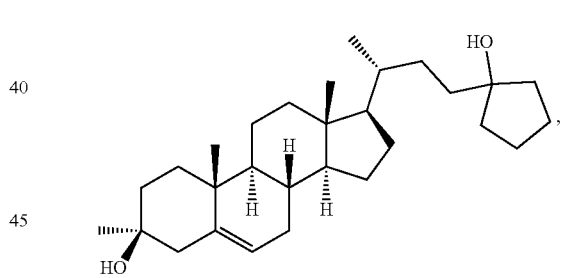
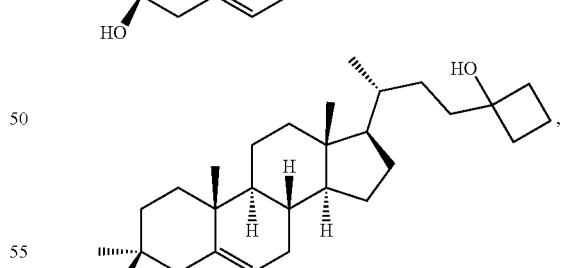
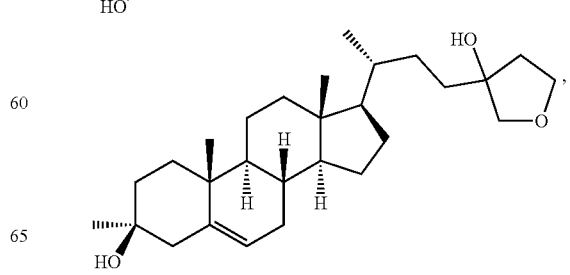

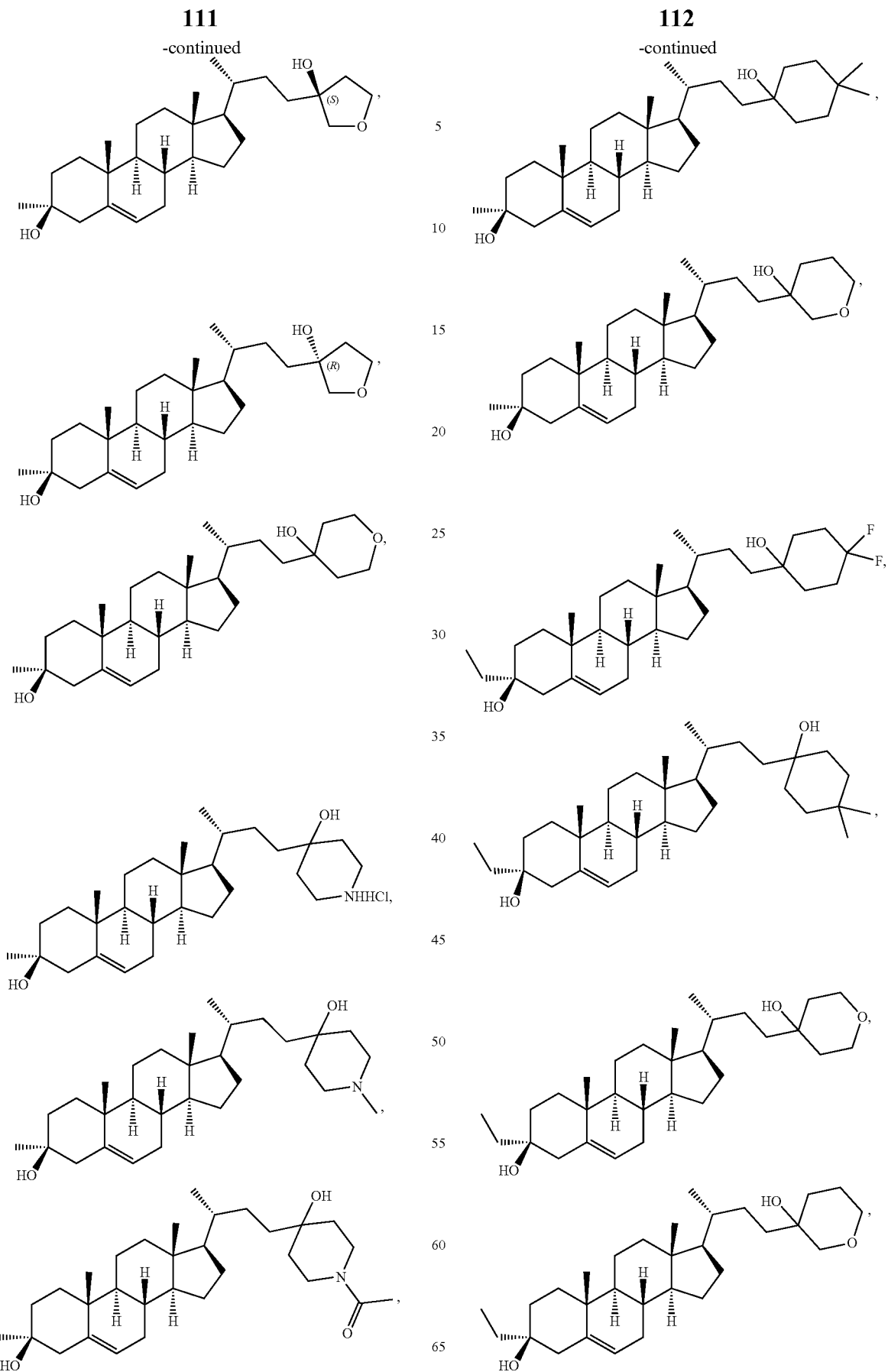

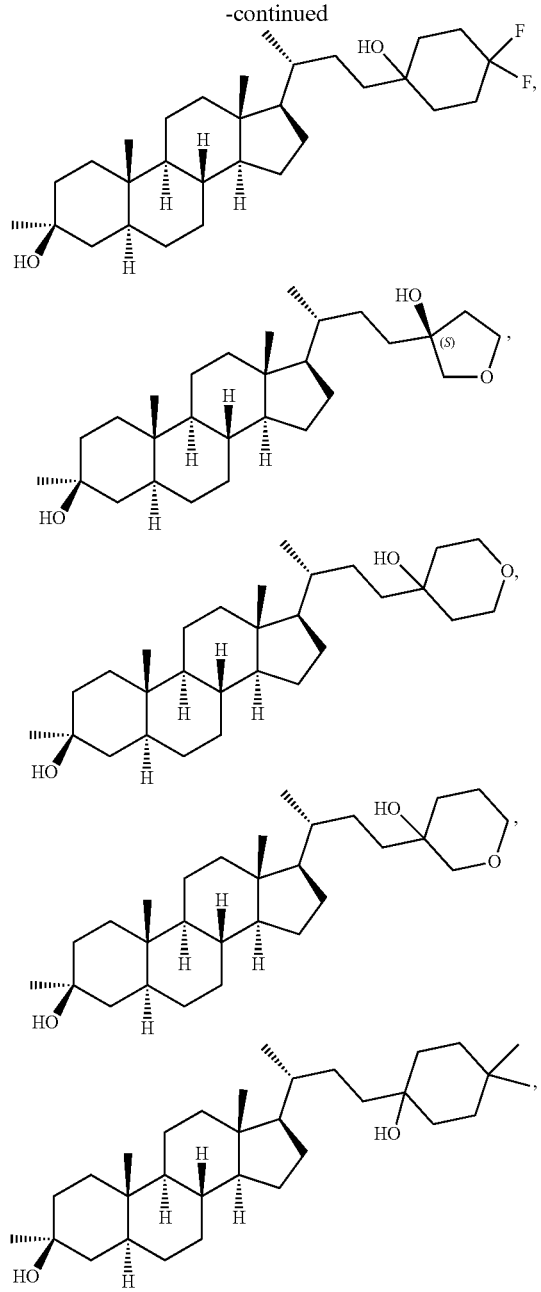
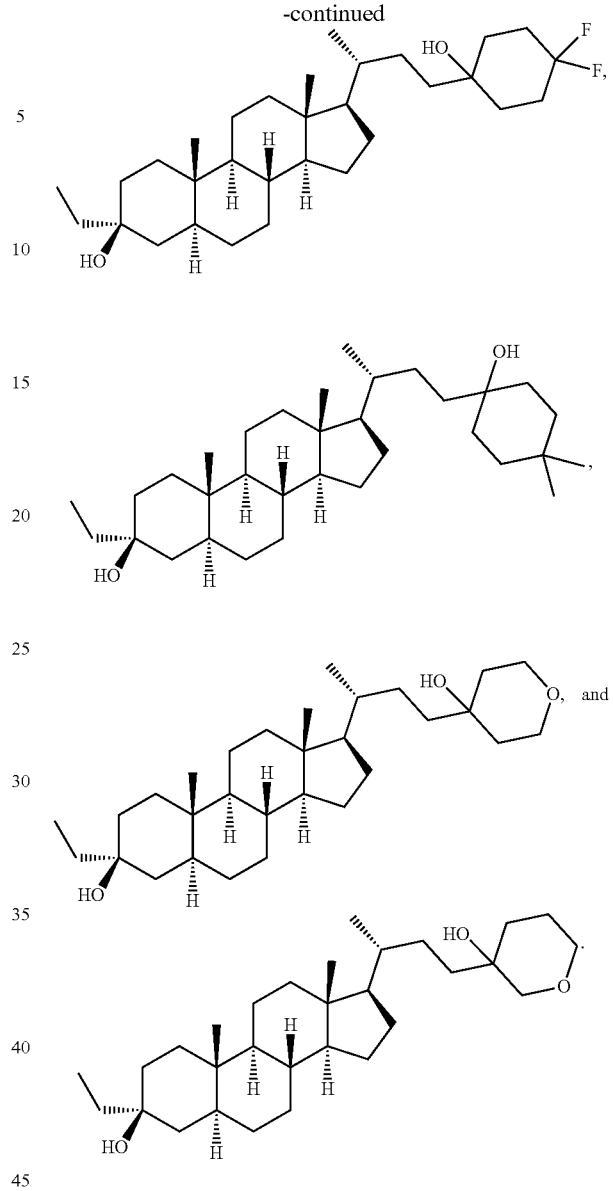
27. A pharmaceutical composition comprising a compound according to claim 1, or a pharmaceutically acceptable salt thereof, and a pharmaceutically acceptable carrier.
* * * * *